United States Patent
Fobare et al.

(10) Patent No.: US 6,395,762 B1
(45) Date of Patent: May 28, 2002

(54) PHENYL AMINO SQUARATE AND THIADIAZOLE DIOXIDE BETA-3 ADRENERGIC RECEPTOR AGONISTS

(75) Inventors: William Floyd Fobare, Lawrenceville, NJ (US); Jill Freymuller, Ambler, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/904,155

(22) Filed: Jul. 12, 2001

Related U.S. Application Data
(60) Provisional application No. 60/218,722, filed on Jul. 17, 2000.

(51) Int. Cl.[7] .................... A01N 43/82; A61K 31/41
(52) U.S. Cl. .................... 514/362; 514/649; 514/652; 548/135; 564/306
(58) Field of Search .................. 564/306; 548/135; 514/362, 652, 649

(56) References Cited

U.S. PATENT DOCUMENTS

| | | | |
|---|---|---|---|
| 5,561,142 A | 10/1996 | Fisher et al. | |
| 5,578,620 A | 11/1996 | Fujita et al. | |
| 5,614,523 A | 3/1997 | Audia et al. | |
| 5,741,789 A | 4/1998 | Hibschman | |
| 5,786,356 A | 7/1998 | Bell et al. | |
| 5,789,402 A | 8/1998 | Audia et al. | |
| 5,840,764 A | * 11/1998 | Quagliato | 514/646 |
| 6,069,176 A | 5/2000 | Tsuchiya et al. | |

FOREIGN PATENT DOCUMENTS

| | | |
|---|---|---|
| EP | 0 449 261 A1 | 10/1991 |
| EP | 0 659 737 A2 | 6/1995 |
| EP | 0 714 883 A1 | 6/1996 |
| EP | 0 764 640 A1 | 3/1997 |
| WO | WO 99/65895 | 12/1999 |
| WO | WO 01/17989 A2 | 3/2001 |
| WO | WO 01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sep. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).
Kiyoto Koguro et al., Synthesis, 1998, 910–914.
Gerard Leclerc et al., J. Med. Chem., 1980, 738–744, 23(7).
D. Mauleon et al., Il Farmaco, 1989. 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. unangst et al., J. Med. Chem., 1994, 322–328, 37.
Sophie Vanwetswinkel et al., J. Anitbiotics, Sep. 1994, 1041–1051, 47(9).
S. Tamada et al., JP 01061468 A2 (English abstract), 1989.

* cited by examiner

*Primary Examiner*—Robert Gerstl
(74) *Attorney, Agent, or Firm*—Steven R. Eck

(57) ABSTRACT

This invention provides compounds of Formula I having the structure

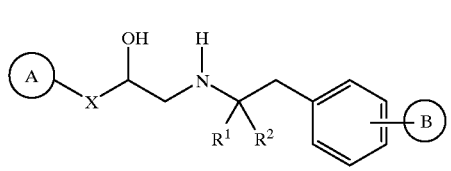

wherein,

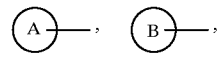

$R^1$, $R^2$, and X are as defined hereinbefore, or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension and frequent urination; and are particularly useful in the treatment or inhibition of type II diabetes.

11 Claims, No Drawings

PHENYL AMINO SQUARATE AND THIADIAZOLE DIOXIDE BETA-3 ADRENERGIC RECEPTOR AGONISTS

This application claims the benefit of U.S. Provisional Application No. 60/218,722, filed Jul. 17, 2000.

BACKGROUND OF THE INVENTION

This invention relates to phenyl-oxo-tetrahydroquinolin-3-yl $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenic inflammation, glaucoma, ocular hypertension, frequent urination; and are particularly useful in the treatment or inhibition of type II diabetes.

The subdivision of $\beta$ adrenergic receptors ($\beta$-AR) into $\beta_1$- and $\beta_2$-AR has led to the development of $\beta_1$- and $\beta_2$-antagonists and/or agonists which have been used in the treatment of cardiovascular disease and asthma. The recent discovery of "atypical" receptors, later called $\beta_3$-AR, has led to the development of $\beta_3$-AR agonists that are potentially useful as antiobesity and antidiabetic agents. For recent reviews on $\beta_3$-AR agonists, see: 1. Strosberg, A. D., *Annu. Rev. Pharmacol. Toxicol.*, 1997, 37, 421; 2. Weber, A. E., *Ann. Rep. Med. Chem.*, 1998, 33, 193; 3. Kordik, C. P. and Reitz, A. B., *J. Med. Chem.*, 1999, 42, 181; 4. Weyer, C., Gautier, J. F., and Danforth, E., *Diabetes and Metabolism*, 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively. Early developments in the $\beta_3$-agonist field are described in European patent 427480, U.S. Pat. Nos. 4,396,627, 4,478,849, 4,999,377, and 5,153,210. These early patents purport to claim compounds with greater selectivity for the $\beta_3$-AR than for the $\beta_1$- and $\beta_2$-AR's. However, clinical trials in humans with such compounds have not been successful to date.

More recently, potent and selective human $\beta_3$ agonists have been described in several patents and published applications: WO 98/32753, WO 97/46556, WO 97/37646, WO 97/15549, WO 97/25311, WO 96/16938, and WO 95/29159; European Patents 659737, 801060, 714883, 764640, and 827746; and U.S. Pat. Nos. 5,561,142, 5,705,515, 5,436,257, and 5,578,620. These compounds were evaluated in a Chinese hamster ovary (CHO) cell model, an assay that predicts the effects expected in humans. These assays utilize cloned human $\beta_3$ receptors, expressed in CHO cells (see refs. Granneman, et al., *Mol. Pharmacol*, 1992, 42, 964; Emorine, et al., *Science*, 1989, 245, 1118; Liggett, *Mol. Pharmacol*, 1992, 42, 634).

$\beta_3$-AR agonists also are useful in controlling urinary incontinence. It has been shown that relaxation of the bladder detrusor is under beta adrenergic control (Li, J. H., Yasay, G. D. and Kau, S. T., "Beta-adrenoceptor subtypes in the detrusor of guinea-pig urinary bladder", *Pharmacology*, 1992, 44, 13–18). Several laboratories have provided recent experimental evidence that activation of the $\beta_3$ receptor subtype by norepinephrine is responsible for relaxation of the urinary bladder in a number of animal species, including humans (Yamazaki Y., et al., "Species differences in the distribution of the $\beta$-AR subtypes in bladder smooth muscle", *Br. J. Pharmacol.*, 1998, 124, 593–599).

Urge urinary incontinence is characterized by abnormal spontaneous bladder contractions that can be unrelated to bladder urine volume. Urge urinary incontinence is often referred to as hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. The neurogenic bladder is associated with an uninhibited micturition reflex, in which an upper motor neuron disease is usually the underlying cause. In either case, the disease is characterized by abnormal spontaneous contractions that result in an unusual sense of urinary urgency and involuntary urine loss. At present, the most common therapy for hyperactive bladder involves the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30 percent.

In the bladder, $\beta_3$-AR agonists activate adenylyl cyclase and generate cAMP through the G-protein coupled $\beta_3$-AR. The resulting phosphorylation of phospholamban/calcium ATPase enhances uptake of calcium into the sarcoplasmic reticulum, thereby decreasing intracellular calcium resulting in an inhibition of bladder smooth muscle contractility.

It is suggested therefore, that activation of the $\beta_3$-AR in the urinary bladder will inhibit abnormal spontaneous bladder contractions and be useful for the treatment of bladder hyperactivity. Note that unlike the antimuscarinics, $\beta_3$-AR agonists would be expected to be active against both neurogenic and myogenic etiologies.

Despite these recent developments there is still no single therapy available for the treatment of type II diabetes (NIDDM), obesity, atherosclerosis, gastrointestinal disorders, neurogenic inflammation, frequent urination and related diseases. A potent and selective $\beta_3$-AR agonist is therefore highly desirable for the potential treatment of these disease states.

DESCRIPTION OF THE INVENTION

This invention provides compounds of Formula I having the structure

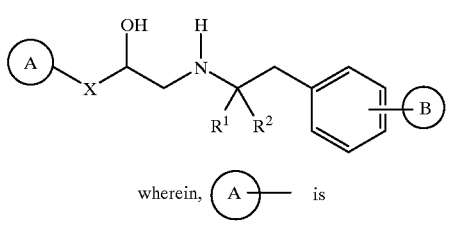

wherein, ─(A)─ is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or (d) a phenyl fused heterocycle having 1–4 heteroatoms selected from O, N, and S, having a second phenyl ring fused to the heterocyclic ring, optionally substituted with 1–2 Y groups;

is

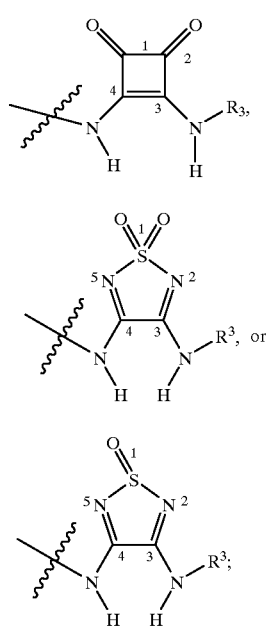

X is —OCH$_2$— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;
R$^1$ and R$^2$ are each, independently, hydrogen, alkyl of 1–6 carbon atoms, or cycloalkyl of 3–8 carbon atoms;
R$^3$ is
  (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;
  (b) cycloalkyl of 3–8 carbon atoms;
  (c) arylalkyl wherein the alkyl moiety contains 1–10 carbon atoms;
  (d) heterocycle or heterocyclealkyl, wherein the alkyl moiety contains 1–6 carbon atoms, and the heterocycle is
    i) a 5–6 membered heterocyclic ring having 1–4 heteroatoms selected from O, N, and S, optionally substituted with 1–2 Y groups;
    ii) a phenyl fused heterocycle having 1–4 heteroatoms selected from O, N, and S, optionally substituted with 1–2 Y groups; or
    iii) a phenyl fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;
Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;
m=0–2;
n=1–2;

or a pharmaceutically acceptable salt thereof, which are selective agonists at human $\beta_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The compounds of the instant invention all contain at least one asymmetric center. Additional asymmetric centers may be present on the molecule depending upon the nature of the various substituents on the molecule. Each such asymmetric center will produce two optical isomers and all such optical isomers, as separated, pure or partially purified optical isomers or racemic mixtures thereof, are included within the scope of the instant invention. Any enantiomer of a compound of the general Formula I may be obtained by stereospecific synthesis using optically pure starting materials of know configuration.

Alkyl and alkenyl include both straight chain as well as branched moieties. Halogen means bromine, chlorine, fluorine, and iodine. Aryl includes monocyclic or bicyclic aromatic carbocyclic groups such as phenyl and naphthyl. Benzyl is the preferred arylalkyl moiety. 3,4-Diaminocyclobut-3-ene-1,2-dione refers to structure of type 2.

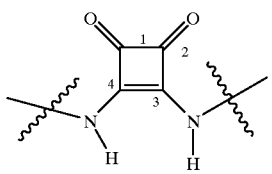

3,4-Diamino-1,1-dioxo-lambda(6)-1,2,5-thiadiazole refers to structure 3.

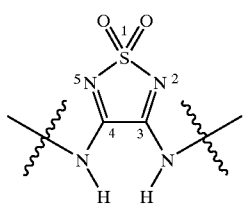

As used herein, a heterocyclic ring is a ring contining 1–4 heteroatoms selected from N, O, and S, indicates a heterocycle which may be saturated, unsaturated, or partially unsaturated. The heterocyclic ring may be attached within structural Formula I by any carbon atom or appropriate heteroatom. It is understood that the heterocyclic ring does not contain heteroatoms in arrangements which would make them inherently unstable. For example, the term heterocyclic ring does not include ring systems containing O—O bonds in the ring backbone. Preferred heterocyclic radicals include pyridinyl, thiophenyl, furanyl, benzothiophenyl, benzofuranyl, benzodioxolyl, quinolinyl, thiadiazolyl, thiazolyl, oxadiazolyl, carbazolyl, pyrrolyl, imidazolyl, benzimidazolyl, benzotriazolyl, 1,2,3,4-tetrahydroquinolyl, 1,2,3,4-tetrahydroisoquinolyl, and pyrazolyl.

Preferred compounds of this invention are the compounds of formula I, wherein

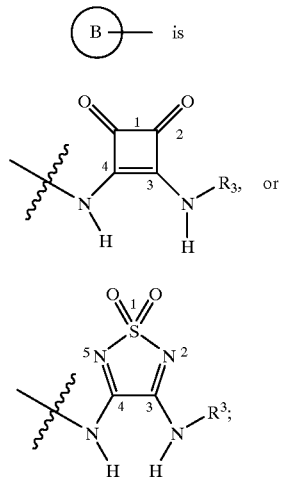

or a pharmaceutically acceptable salt thereof.

More preferred compounds of this invention are the compounds of formula 1, wherein

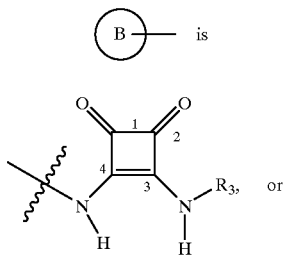

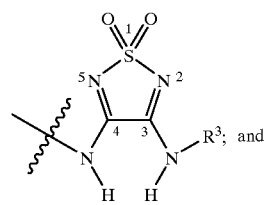

$R^3$ is alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$; or a pharmaceutically acceptable salt thereof.

Specifically preferred compounds of this invention are:
a) 3-Butylamino-4-(4-{2-[(2R)-2-(3-chloro-phenyl)-2-hydroxy-ethylamino]-propyl}-phenylamino)-cyclobut-3-ene-1,2-dione;
b) 3-(4-{2-[(2R)-2-(3-Chloro-phenyl)-2-hydroxy-ethylamino]-propyl}-phenylamino)-4-octylamino-cyclobut-3-ene-1,2-dione;
c) 3-(4-{2-[(2S)-3-(4-Benzyloxy-phenoxy)-2-hydroxy-propylamino]-propyl}-phenylamino)-4-octylamino-cyclobut-3-ene-1,2-dione;
d) 3-(4-{2-[(2S)-2-Hydroxy-3-(4-hydroxy-phenoxy)-propylamino]-propyl}-phenylamino)-4-octylamino-cyclobut-3-ene-1,2-dione;
e) 3-Decylamino-4-(4-{2-[2-hydroxy-phenoxy)-propylamino]-propyl}phenylamino)-cyclobut-3-ene-1,2-dione;
f) 3-(4-{2-[(2S)-3-(9H-Carbazol-4-yloxy)-2-hydroxy-propylamino]-propyl}-phenylamino)-4-octylamino-cyclobut-3-ene-1,2-dione;
g) 3-(4-{[(2S)-3-(9H-Carbazol-4-yloxy)-2-hydroxy-propylamino]-propyl}-phenylamino)-4-decylamino-cyclobut-3-ene-1,2-dione;
h) 3-Decylamino-4-{4-[4-[2[((2S)-2-hydroxy-3-phenoxy-propylamino)-propyl]-phenylamino)-cyclobut-3-ene-1,2-dione;
i) 3-{4-[2-((2S)-2-Hydroxy-3-phenoxy-propylamino)-propyl]-phenylamino}-4-octylamino-cyclobut-3-ene-1,2-dione;
j) (1 R)-1-(3-Chloro-phenyl)-2-{1-methyl-2-[4-(octylamino-1,1-dioxo-1H-1-.lambda(6).-[1,2,5] thiadiazol-3-ylamino)-phenyl]-ethylamino}-ethanol;
k) (1 R)-1-(3-Chloro-phenyl)-2-{2-[3-(4-hexylamino-1,1-dioxo-1H-1-.lambda(6).-[1,2,5]thiadiazol-3-ylamino)-phenyl]-1-methyl-ethylamino}-ethanol;
l) (1 R)-1-(3-Chloro-phenyl)-2-{1-methyl-2-[3-(4-octylamino-1,1-dioxo-1H-1-.lambda(6).-[1,2,5] thiadiazol-3-ylamino)-phenyl]-ethylamino}-ethanol;
m) (2S)-1-(4-Benzyloxy-phenoxy)-3-{1-methyl-2-[4-(4-octylamino-1,1-dioxo-1H-1.lambda(6).-[1,2,5] thiadiazol-3-ylamino)-phenyl]-ethylamino}-propan-2-ol;
n) 4-((2S)-2-Hydroxy-3-{1-methyl-2-[4-(4-octylamino-1,1-dioxo-1H-1-.lambda(6).-[1,2,5]thiadiazol-3-ylamino)-phenyl]-ethylamino}-propoxy)-phenol;
o) (2S)-1-(4-Benzyloxy-phenoxy)-3-{2-[4-(4-decylamino-1,1-dioxo-1H-1-.lambda(6).-[1,2,5] thiadiazol-3-ylamino)-phenyl]-1-methyl-ethylamino}-propan-2-ol;

p) (2S)-1-(4-Benzyloxy-phenoxy)-3-{1,1-dimethyl-2-[4-(4-octylamino-1,1-dioxo-1H-1-.lambda(6).-[1,2,5]thiadiazol-3-ylamino)-phenyl]-ethylamino}-propan-2-ol;

q) (2S)-1-(9H-Carbozol-4-yloxy)-3-{2-[4-(4-decylamino-1,1-dioxo-1H-1-.lambda(6).-[1,2,5]thiadiazol-3-ylamino)-phenyl]-1-methyl-ethylamino}-propan-2-ol;

r) (2S)-1-{2-[4-(4-Decylamino-1, 1-dioxo-1H-1(lambda(6))-[1,2,5]thiadiazol-3-ylamino)-phenyl]-1-methyl-ethylamino}-3-phenoxy-propan-2-ol;

s) (2S)-1-(9H-Carbazol-4-yloxy)-3-{1-methyl-2-[4-(4-octylamino-1,1-dioxo-1H-1(lambda(6))-[1,2,5]thiadiazol-3-ylamino)-phenyl]-ethylamino}-propan-2-ol;

t) (2S)-1-{[1-methyl-2-(4-{[4-(octylamino)-1,1-dioxido-1,2,5-thiadiazol-3-yl]amino}phenyl)ethyl]amino}-3-phenoxypropan-2-ol;

u) 4-((2S)-3-{2-[4-(4-Decylamino-1,1-dioxo-1H-1(lambda(6))-[1,2,5]thiadiazol-3-ylamino)-phenyl]-1-methyl-ethylamino}-2-hydroxy-propoxy)-phenol;

v) N-[2-Benzyloxy-5-((1R)-1-hydroxy-2-{1-methyl-2-[4-(4-octylamino-1,1-dioxo-1H-1(lambda(6))-[1,2,5]thiadiazol-3-ylamino)-phenyl]-ethylamino}-ethyl)-phenyl]-methanesulfonamide;

w) N-[2-Benzyloxy-5-((1R)-2-{2-[4-(4-decylamino-1,1-dioxo-1H-1(lambda(6))-[1,2,5]thiadiazol-3-ylamino)-phenyl]-1-methyl-ethylamino}-1-hydroxy-ethyl)-phenyl]-methanesulfonamide;

x) N-[2-Hydroxy-5-((1R)-1-hydroxy-2-{1-methyl-2-[4-(4-octylamino-1,1-dioxo-1H-1(lambda(6))-[1,2,5]thiadiazol-3-ylamino}-ethyl)-phenyl]-methanesulfonamide;

y) N-[5-((1R)-2-{2-[4-(4-Decylamino-,1,1-dioxo-1H-1(lambda(6))-[1,2,5]thiadiazol-3-ylamino)-phenyl]-1-methyl-ethylamino}-1-hydroxy-ethyl)-2-hydroxy-phenyl]-methanesulfonamide;

z) 4-((2S)-3-{1,1-Dimethyl-2-[4-(4-octylamino-1,1-dioxo-1H-1(lambda(6))-[1,2,5]thiadiazol-3ylamino)-phenyl]-ethylamino}-2-hydroxy-propoxy)-phenol;

aa) (2S)-1-(4-Benzyloxy-phenoxy)-3-(2-{4-[4-(2,2-diphenyl-ethylamino)-1,1-dioxo-1H-1(lambda(6))-[1,2,5]thiadiazol-3-ylamino]-phenyl}-1,1-dimethyl-ethylamino)-propan-2-ol;

bb) 4-[(2S)-3-(2-{4-[4-(2,2-Diphenyl-ethylamino)-1,1-dioxo-1H-1(lambda(6))-[1,2,5]thiadiazol-3-ylamino]-phenyl}-1,1-dimethyl-ethylamino)-2-hydroxy-propoxy]-phenol;

cc) (2S)-1-(4-Benzyloxy-phenoxy)-3-[2-(4-{1,-dioxo-4-[(1-phenyl-cyclopentylmethyl)-amino]-1H-1(lambda(6))-[1,2,5]thiadiazol-3-ylamino}-phenyl)-1-methyl-ethylamino]-propan-2-ol;

dd) 4-{(2S)-3-[2-(4-{1 1-Dioxo-4-[(1-phenyl-cyclopentylmethyl)-amino]-1H-1(lambda(6))-[1,2,5]thiadiazol-3-ylamino}-phenyl)-1-methyl-ethylamino]-2-hydroxy-propoxy}-phenol;

ee) (2S)-1-(4-Benzyloxy-phenoxy)-3-{2-{4-(4-{[1-(4-dimethylamino-phenyl)-cyclopentylmethyl]-amino}-1,1-dioxo-1H-1(lambda(6))-[1,2,5]thiadiazol-3-ylamino)-phenyl]-1,1-dimethyl-ethylamino}-propan-2-ol;

ff) 4-[4-(4-{2-[(2S)-3-(4-Benzyloxy-phenoxy)-2-hydroxy-propylamino]-propyl}-phenylamino)-1,1-dioxo-1H-1(lambda(6))-[1,2,5]thiadiazol-3-ylamino]-butyric acid ethyl ester;

gg) 4-{[(2S)-3-({2-[4-({4-[({1-[4-(dimethylamino)phenyl]cyclopentyl}methyl)amino]-1,1-dioxido-1,2,5-thiadiazol-3-yl}amino)phenyl]-1,1-dimethylethyl}amino)-2-hydroxypropyl]oxy}phenol;

hh) 4-[4-(4-{2-[(2S)-2-Hydroxy-3-(4-hydroxy-phenoxy)-propylamino]-propyl}-phenylamino)-1,1-dioxo-1H-1.lambda(6).-[1,2,5]thiadiazol-3-ylamino]-butyric acid ethyl ester;

ii) 1-[4-(1-{[4-(4-{2-[(2R)-3-(4-Benzyloxy-phenoxy)-2-hydroxy-propylamino]-2-methyl-propyl}-phenylamino)-1,1-dioxo-1H-1.lambda(6).-[1,2,5]thiadiazol-3-ylamino]-methyl}-cyclopentyl)-phenyl]-3-hexyl-urea;

jj) 1-Hexyl-3-[4-(1-{[4-(4-{2-[(2S)-2-hydroxy-3-(4-hydroxy-phenoxy)-propylamino]-2-methyl-propyl}-phenylamino)-1, 1-dioxo-1H-1.lambda(6).-[1,2,5]thiadiazol-3-ylamino]-methyl}-cyclopentyl)-phenyl]-urea;

kk) N-[5-(2-{2-[4-(4-{[1-(4-Dimethylamino-phenyl)-cyclopentylmethyl]-amino}-1,1-dioxo-1H-1 .lambda(6).-[1,2,5]thiadiazol-3-ylamino)-phenyl]-1,1-dimethyl-ethylamino}-1-hydroxy-ethyl)-2-hydroxy-phenyl]-methanesulfonamide;

ll) (2S)-1-(4-Benzyloxy-phenoxy)-3-{2-[4-(4-octylamino-1,1-dioxo-1H-1.lambda(6).-[1,2,5]thiadiazol-3-ylamino)-phenyl]ethylamino}-propan-2-ol;

mm) 4-((2S)-2-Hydroxy-3-{2-[4-(4-octylamino-1,1-dioxo-1H-1.lambda(6).-[1,2,5]thiadiazol-3-ylamino)-phenyl]-ethylamino}-propoxy)-phenol;

nn) (2S)-i-(1,3-Benzodioxol-5-yloxy)-3-{1-methyl-2-[4-(4-octylamino-1,1-dioxo-1H-1.lambda(6) .-[1,2,5]thiadiazol-3-ylamino)-phenyl]-ethylamino}-propan-2-ol;

oo) (S)-4-{2-Hydroxy-3-[2-(4-{4-[2-(4-methoxy-phenyl)-ethylamino]-1,1-dioxo-1H-1.lambda(6) .-[1,2,5]thiadiazol-3-ylamino}-phenyl)-1-methyl-ethylamino]-propoxy}-phenol;

pp) 4-{(2S)-3-[2-(4-{4-[2-(4-Fluoro-phenyl)-ethylamino]-1,1-dioxo-1H-1.lambda(6).-[1,2,5]thiadiazol-3-ylamino}-phenyl-1-methyl-ethylamino]-2-hydroxy-propoxy}-phenol;

qq) 4-{(2S)-3-[1-(4-{4-[2-(4-Fluoro-phenyl)-ethylamino]-1,1-dioxo-1H-1.lambda(6).-[1,2,5]thiadiazol-3-ylamino}-phenyl)-piperidin-4-ylamino]-2-hydroxy-propoxy}-phenol; or a pharmaceutically acceptable salt thereof.

The compounds of this invention were be prepared according to the following schemes from commercially available starting materials or starting materials which can be prepared using literature procedures. These schemes show the preparation of representative compounds of this invention.

In Scheme 1 the 4-nitrophenyl-2-aminopropane hydrochloride 4 is known in the literature (J. Med. Chem. 1977, 21, 56) or readily prepared by methods commonly known to those skilled in the art. Protection of the amino group with di-tert-butyl dicarbonate and a base yields the Boc-protected (Boc =tert-butoxy cabonyl) amine 5. Catalytic hydrogenation in a solvent such as methanol or ethanol gives the aniline 6. Reaction of the aniline 6 with the commercially available 3,4-diethoxy-3-cyclobutene-1,2-dione in a refluxing solvent like ethanol or tert-butanol yields the cyclobutenedione adduct 7. Substitution of the ethoxy group with a suitably functionalized amine ($R^3NH_2$) in refluxing solvent, like ethanol or methanol, results in 8. Deprotection of the amine with trifluoroacetic acid in a halogenated solvent like methylene chloride, then coupling of the amine with an epoxide in a solvent like dimethyl formamide or methanol at 40 to 60 degrees Celsius, results in the product of formula I. If there is a benzyl protecting group on a substituent, as in the case for the A group the amino group with di-tert-butyl dicarbonate and base yields the Boc-protected (Boc=tert-butoxy cabonyl) amine 10. Catalytic hydrogenation with a metal catalyst in a solvent such as ethanol or methanol gives the aniline 11. Aniline 11 is reacted with 3,4-diethoxy-1,1-dioxo-1,2,5-thiadiazole in refluxing alcohol to yield adduct 13 (J. Org. Chem. 1975, 40, 2743). Substitution of the ethoxy group

SCHEME 1

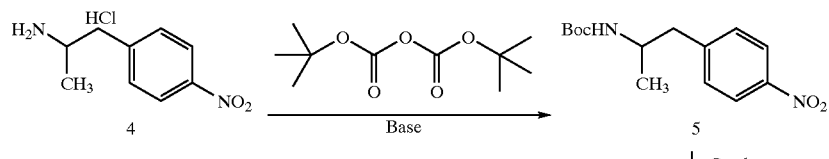

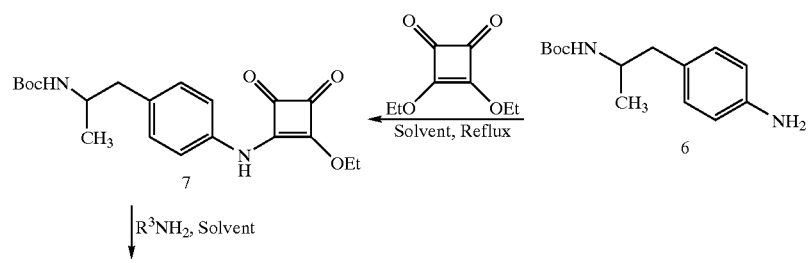

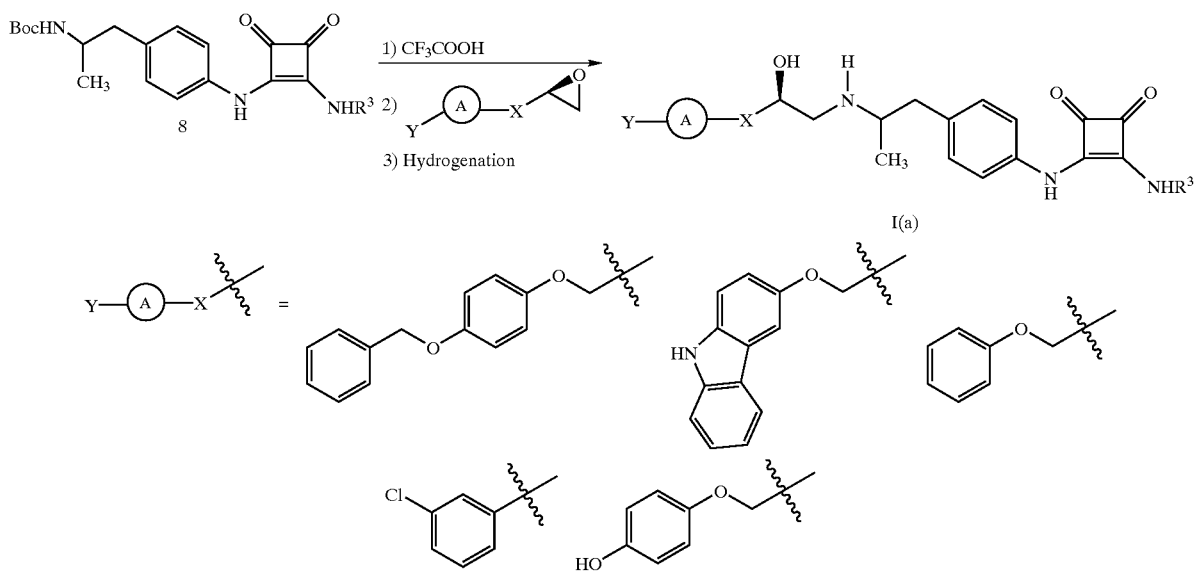

with a 4-benzyloxy-phenol, this can be deprotected by catalytic hydrogenation with a metal catalyst in an organic solvent like methanol or ethanol to yield the corresponding phenol.

In Scheme 2 is described the synthesis of a series of 3-phenyl substituted anilino derivatives. The 3-nitrophenyl-2-aminopropane hydrochloride 9 was prepared in the same manner as for 4-nitrophenyl-2-aminopropane hydrochloride 4, except 3-nitrobenzaldehyde was used instead of 4-nitrobenzaldehyde as the starting material. Protection of with a suitably functionalized amine ($R^3NH_2$) in refluxing alcohol results in 12. Deprotection of the amine with trifluoroacetic acid in a chlorinated hydrocarbon, then coupling of the amine with an epoxide in a solvent like dimethyl formamide or methanol at 40 to 60 degrees Celsius results in the product of formula I. If there is a benzyl protecting group on a substituent, as in the case for the A group with a 4-benzyloxy-phenol, this can be deprotected by catalytic hydrogenation with a metal catalyst in either methanol or ethanol to yield the corresponding phenol.

SCHEME 2

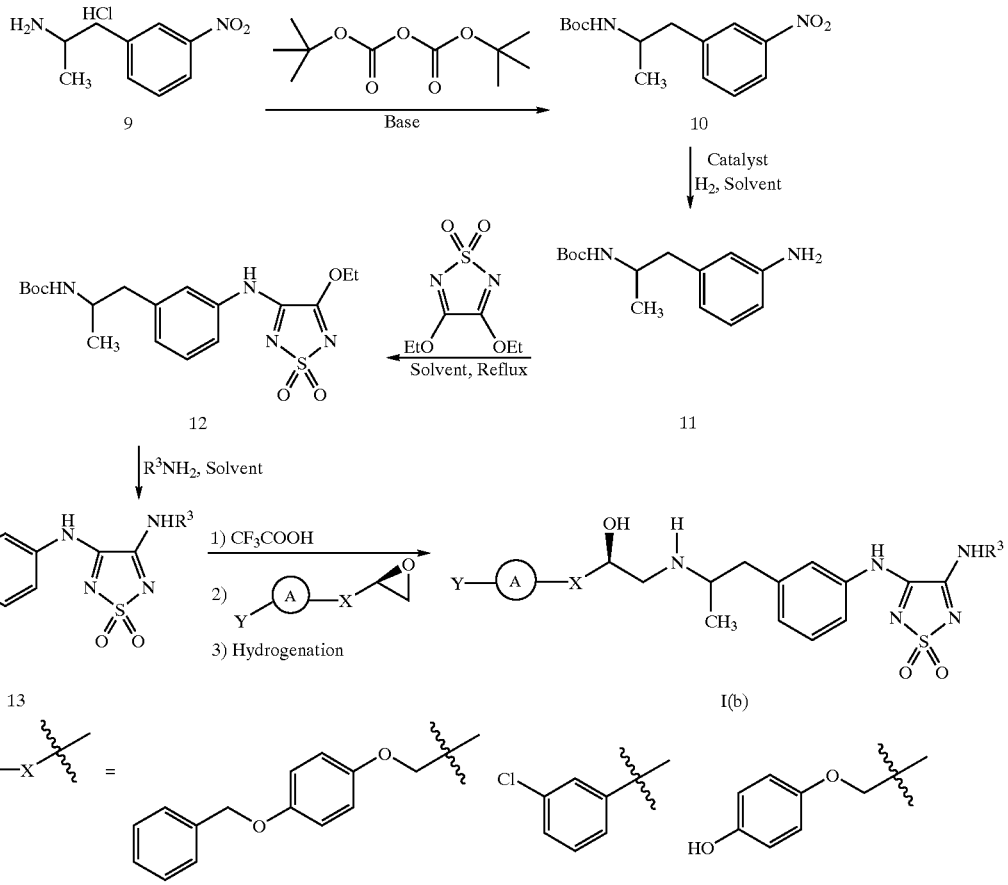

In Scheme 3 is described the synthesis of a series of 4-substituted anilino compounds with B as the 3,4-disubstituted-1,1-dioxo-1,2,5-thiadiazole group. Utilizing the previously mentioned aniline 6 and upon reaction with 3,4-diethoxy-1,1-dioxo-1,2,5-thiadiazole in refluxing solvent such as ethanol gives the adduct 15. Substitution of the ethoxy group with a suitably functionalized amine ($R^3NH_3$) in refluxing solvents like ethanol results in 15. Deprotection of the amine with trifluoroacetic acid in a halogenated solvent, then coupling of the amine with an epoxide in a solvent like dimethyl formamide or methanol at 40 to 60 degrees Celsius results in the product of formula I. If there is a benzyl protecting group on a substituent, as in the case for the A group with a 4-benzyloxy-phenol, this can be deprotected by hydrogenation with 10% palladium on carbon in either methanol or ethanol to yield the corresponding phenol.

The synthesis of the 4-(2-amino-2-methyl-propyl)-aniline analogs (where $R^1$, $R^2$ are methyl) is described in Scheme 4. The 4-(2-amino-2-methyl-propyl)-aniline, 17, is known in the literature and is synthesized by catalytic hydrogenation (10% Pd/C) of the 2-methyl-2-nitropropyl-4-nitroaniline (J. Am. Chem. Soc. 1949, 71, 2290). Protection of the alkylamine of 17 was accomplished with di-tert-butyl dicarbonate in a halogenated solvent to give 18. The aniline was coupled to 3,4-diethoxy-1,1-dioxo-1,2,5-thiadiazole in refluxing

SCHEME 3

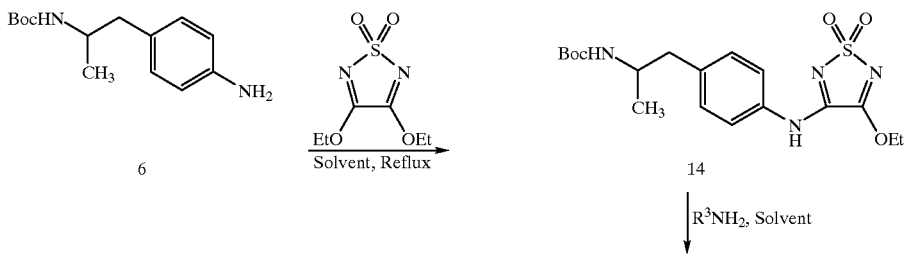

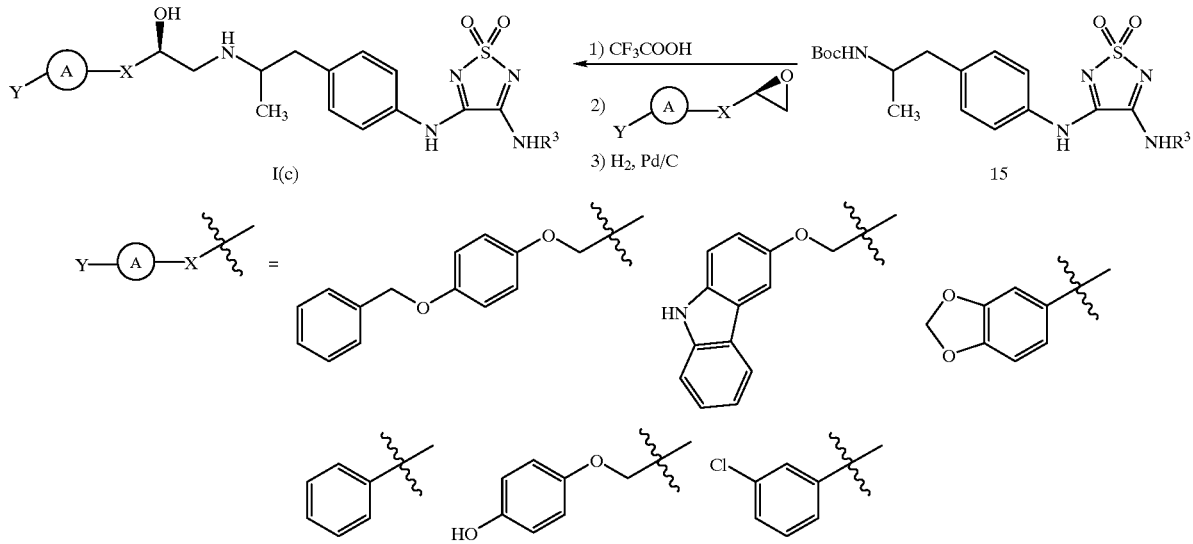

alcohol to yield 19. Substitution of the ethoxy group with a suitably functionalized amine ($R^3NH_2$) in refluxing alcohol results in 20. Deprotection of the amine with trifluoroacetic acid in methylene chloride, then coupling of the amine with an epoxide in a solvent like dimethyl formamide or methanol at 40 to 60 degrees Celsius results in the product of formula I. If there is a benzyl protecting group on a substituent, as in the case for the A group with a 4-benzyloxy-phenol, this can be deprotected by catalytic hydrogenation with a metal catalyst in either methanol or ethanol to yield the corresponding phenol.

In Scheme 5 is the synthesis of analogs of 4-aminophenethylamine. The readily available 4-aminophenethylamine was protected with di-tert-butyl dicarbonate (Boc group) to give 21. The aniline was coupled to 3,4-diethoxy-1,1-dioxo-1,2,5-thiadiazole in refluxing alcohol to yield 22. Substitution of the ethoxy group with a suitably functionalized amine ($R^3NH_2$) in refluxing alcohol results in 23. Deprotection of the amine with trifluoroacetic acid in a halogenated solvent, then coupling of the amine with an epoxide in a solvent like dimethyl formamide or methanol at 40 to 60 degrees Celsius results in the product of formula I. If there is a benzyl protecting group on a substituent, as in the case for the A group with a 4-benzyloxy-phenol, this can be deprotected by hydrogenation with a metal catalyst in a solvent like methanol or ethanol to yield the corresponding phenol.

SCHEME 4

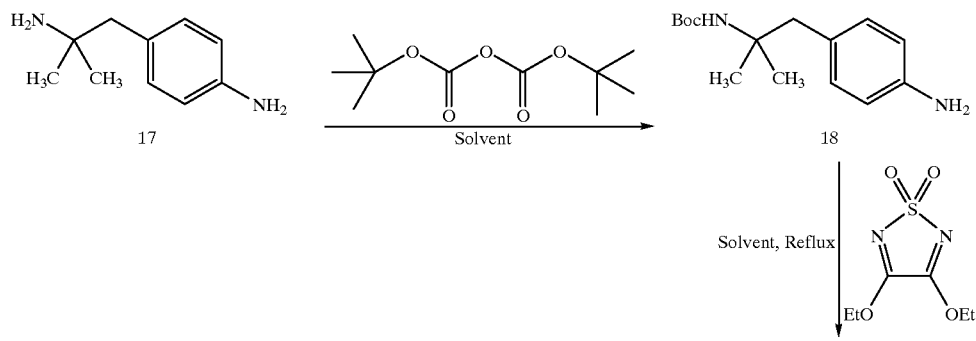

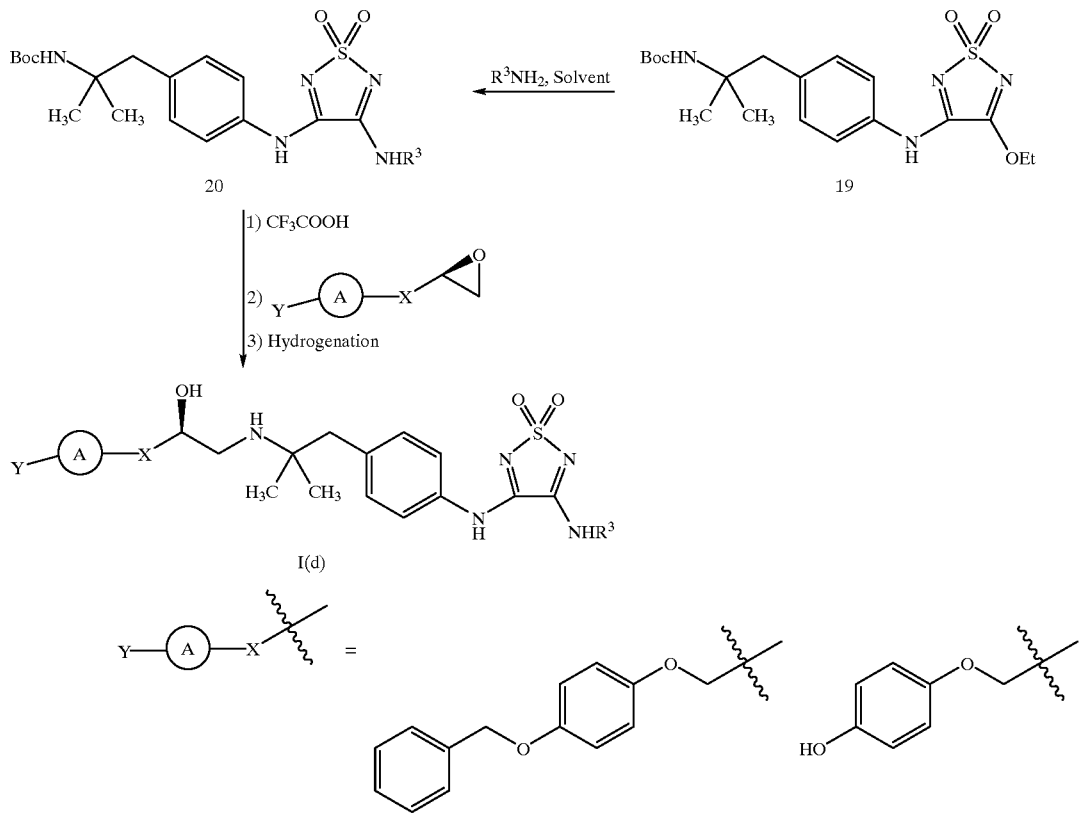

Several examples were synthesized using a coupling reaction between an amine and an alkyl bromide or iodide instead of the previously mentioned epoxide opening. Utilizing protected amines like structures 8, 13, 15, or 20 and treating with trifluoroacetic acid in a halogenated solvent yields the amine, which after isolation was allowed to react with the bromide or iodide in a refluxing solvent like tetrahydrofuran (THF) with a base, like diisopropylethyl amine to yield 24 (Scheme 6 for 15). This can be deprotected with tetrabutylammonium fluoride in a solvent like THF to give the alcohol and hydrogenation with a metal catalyst to yield the phenol 25.

SCHEME 5

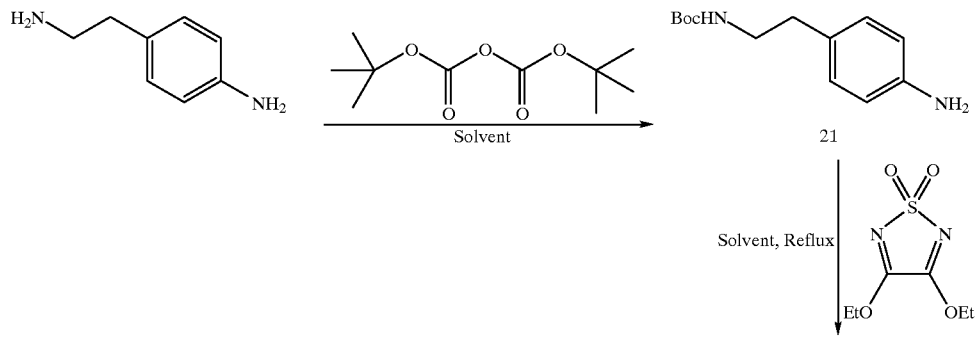

-continued
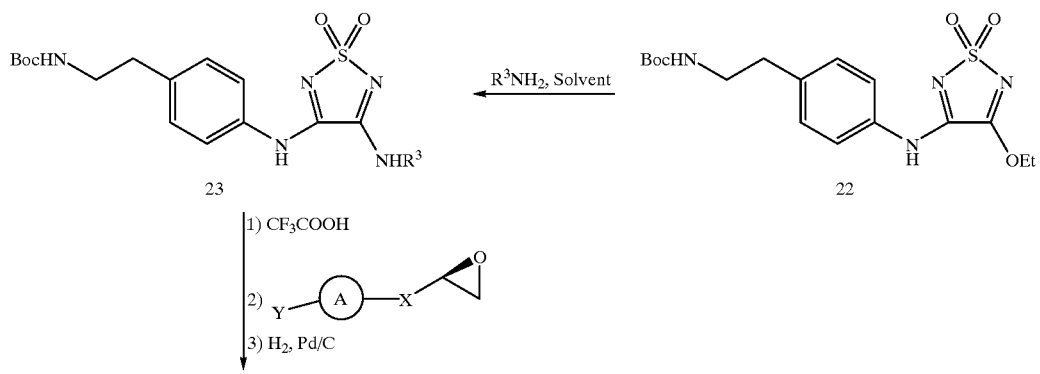
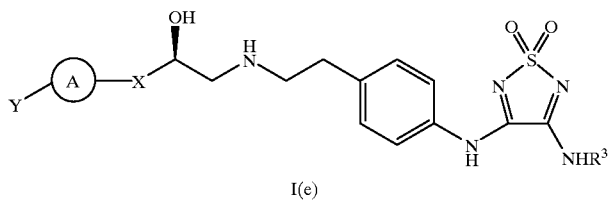
I(e)
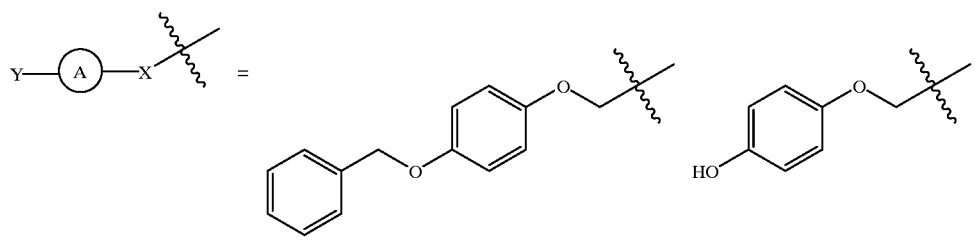
SCHEME 6
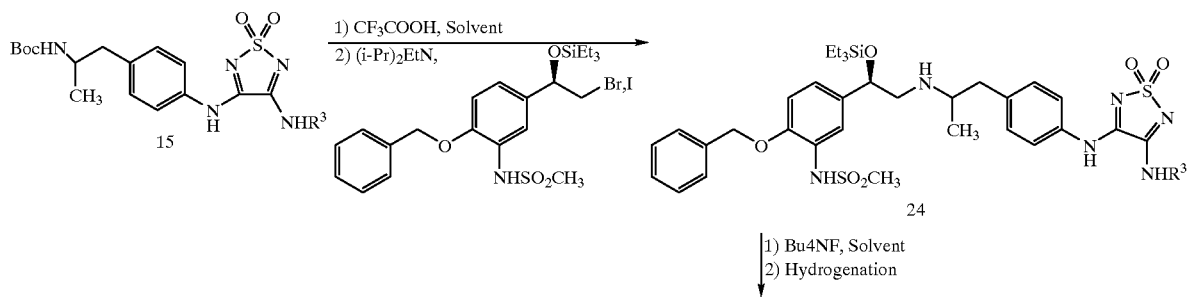

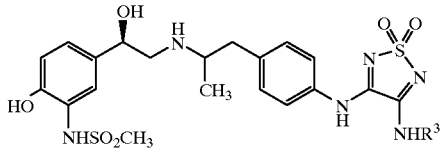

25

Synthesis of the chiral epoxide 26 was accomplished utilizing the published procedure (J. Med. Chem. 1992, 35, 3081).

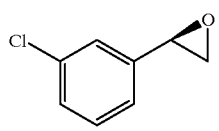

26

Carbazole epoxide 27 was synthesized from 4-hydroxycarbazole (Nucl. Med. Biol. 1992, 19, 563 and J. Med. Chem. 1996, 39, 3260) and (S)-glycidyl nosylate and potassium carbonate in refluxing 2-butanone.

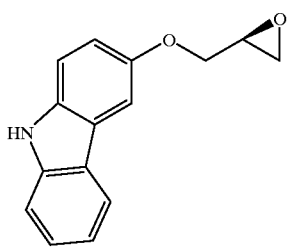

27

The bezyloxy protected phenoxy-epoxide, 28, was synthesized from 4-benzyloxy phenol and (S)-glycidyl nosylate with base in a suitable solvent. The unsubstituted phenyl derivative 29 was synthesized in the same manner except phenol was used.

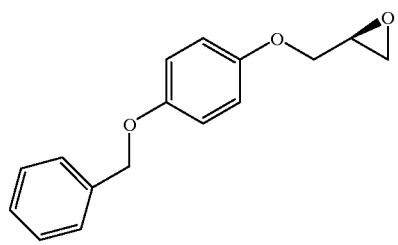

28

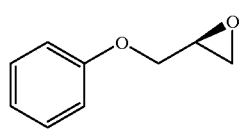

29

The amines ($R^3NH_2$) groups utilized in this invention are either readily available or easily synthesized using methods known to those skilled in the art. The spiro fused phenethylamines were synthesized from the corresponding substituted phenylacetonitriles. 4-Dimethylaminophenylacetonitrile is treated with dimsyl sodium (synthesized from dimethyl sulfoxide (DMSO) and sodium hydride) and then with 1,4-dibromobutane to yield 30 (J. Org. Chem. 1971, 36, 1308). Reduction of the nitrile, 30, with sodium bis(2-methoxyethoxy)aluminum hydride in a refluxing solvent like toluene, yields the corresponding amine 31 (Scheme 7).

SCHEME 7

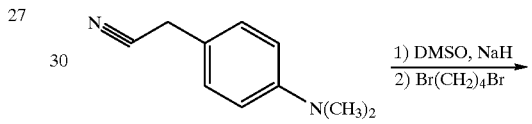

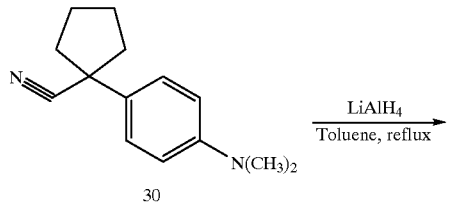

30

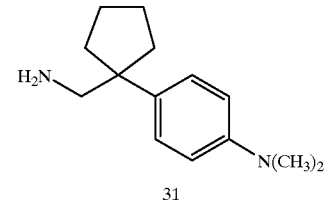

31

The synthesis of amine 34 is described in Scheme 8. 4-Nitrophenylacetonitrile was reacted with dimsyl sodium then 1,4-dibromobutane to yield the spiro-fused compound 32. Reaction with sodium bis(methoxyethoxy) aluminum hydride in a refluxing solvent, then protection as the Boc group gave the nitro compound 33.

SCHEME 8

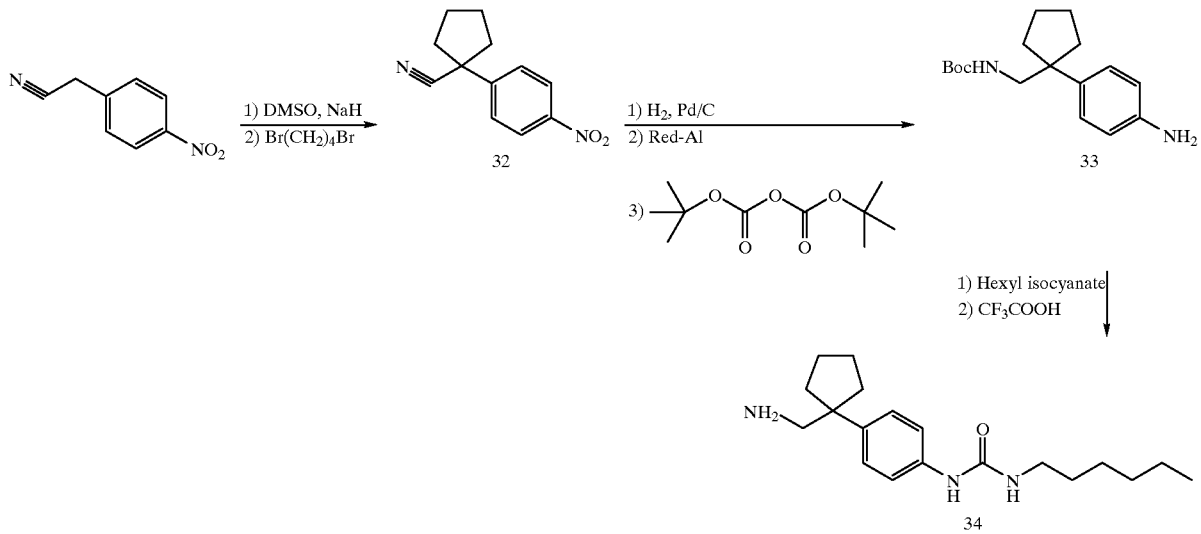

Hydrogenation of the nitro group with a metal catalyst in an alcoholic solvent, reaction with hexyl isocyanate in a halogenated solvent and removal of the Boc protecting group yields the spiro-fused amine 34.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of the compounds of this invention to treat or inhibit disorders related to insulin resistance or hyperglycemia was confirmed with representative compounds of this invention in the following standard pharmacological test procedures, which measured the binding selectivity of the $\beta_1$-, $\beta_2$-, and $\beta_3$-AR. Binding to the receptors was measured in Chinese Hamster ovary (CHO) cells that were transfected with $\beta_1$-, $\beta_2$-, and $\beta_3$-AR's. The following briefly summarizes the procedures used and results obtained.

Transfection of CHO cells with $\beta_1$- and $\beta_2$-AR: CHO cells were transfected with human $\beta_1$- or $\beta_2$-AR as described in Tate, K. M., *Eur. J. Biochem.*, 1991, 196, 357–361.

Cloning of Human $\beta_3$-AR Genomic DNA: cDNA was constructed by ligating four polymerase chain reaction (PCR) products using the following primers: an ATG-Narl fragment, sense primer 5'-CTTCCCTACCGCCCCACGCGCGATC3' and anti-sense primer 5'CTGGCGCCCAACGGCCAGTGGC-CAGTC3' ; a Narl-Accl fragment, 5'TTGGCGCTGATG-GCCACTGGCCGTTTG3' as sense and 5'GCGCGTAGACGAAGAGCATCACGAG3' as anti-sense primer; an Accli—Styl fragment, sense primer 5'CTCGT-GATGCTCTTCGTCTCACGCGC3' and anti-sense primer 5'GTGAAGGTGCCCATGATGAGACCCAAGG3' and a Styl-TAG fragment, with sense primer 5' CCCTGTGCAC-CTTGGGTCTCATCATGG3' and anti-sense primer 5' CCTCTGCCCCGGTTACCTACCC3' . The corresponding primer sequences are described in Mantzoros, C. S., et.al., Diabetes, 1996, 45, 909–914. The four fragments are ligated into a pUC 18 plasmid (Gibco-BRL) and sequenced. Full-length $\beta_3$-AR clones (402 amino acids) containing the last 6 amino acids of h$\beta_3$-AR are prepared with the $\beta_3$-$\beta$ARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin—Streptomycin and Geneticin. On the day of test procedure, growth medium was replaced with preincubation media (Dulbecco's Modified Eagle Media) and incubated for 30 minutes at 37° C. Pre-incubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were assayed over a concentration range of $10^{-9}$ M to $10^{-5}$ M for $\beta_3$-AR transfected cells and $10^{-8}$ to $10^{-4}$ M for $\beta_1$-AR and $\beta_2$-AR transfected cells. Isoproterenol ($10^{-5}$ M) was used as an internal standard for comparison of activity. Cells were incubated at 37° C. on a rocker for 30 min with the $\beta_3$-AR transfected cells and 15 min with $\beta_1$-AR and $\beta_2$-AR transfected cells. Incubation was stopped by the addition of 0.2N HCl and the acid was neutralized with 2.5N NaOH. The plates, containing the cells and neutralized media, were stored at −20° C. until ready to test for cAMP using the SPA test kit (Amersham).

Data Analysis and Results: Data collected from the SPA test procedure were analyzed as percent of the maximal isoproterenol response at $10^{-5}$ M. Activity curves were plotted using the SAS statistical and graphics software. $EC_{50}$ values were generated for each compound and the maximal response (IA) exhibited by each compound was compared to the maximal response of isoprotenol at $10^{-5}$ M from the following formula:

IA=% activity compound

% activity isoproterenol

Shown in Table I are the $\beta_3$-AR $EC_{50}$ and IA values for the representative compounds of this invention that were evaluated in this standard pharmacological test procedure. Compounds of the present invention were active at the $\beta_3$-AR as shown by these results. The compounds of this invention were considerably less active, if at all, at the $\beta_1$- and/or $\beta_2$-AR.

TABLE 1

| Compound No. | EC$_{50}$($\beta_3$, μM) | IA($\beta_3$) |
|---|---|---|
| 1 | 0.115 | 0.16 |
| 2 | 0.198 | 0.42 |
| 3 | 0.038 | 0.86 |
| 4 | 0.068 | 1.10 |
| 4 (step F) | 1.056 | 0.37 |
| 5 | 0.018 | 0.75 |
| 5 (step E) | 1.39 | 0.15 |
| 6 | 0.002 | 1.26 |
| 6 (step B) |  | 0.32 |
| 7 | 0.055 | 0.74 |
| 7 (step E) | 0.682 | 0.56 |
| 8 | 0.01 | 0.91 |
| 8 (step H) | 0.06 | 0.40 |
| 9 | 0.204 | 0.74 |
| 10 | 0.087 | 0.71 |
| 11 |  | 0.29 |
| 12 | 0.011 | 1.45 |
| 14 | 0.021 | 0.81 |
| 15 | 0.086 | 0.97 |
| 16 | 0.233 | 0.47 |
| 17 |  | 0.31 |
| 18 |  | 0.46 |
| 19 |  | 0.36 |
| 20 |  | 0.39 |
| 21 | 0.064 | 0.64 |
| 22 |  | 0.39 |
| 23 | 1.36 | 0.64 |
| 24 | 0.081 | 0.41 |
| 25 | 0.088 | 0.85 |
| 27 | 0.009 | 1.27 |
| 28 | 1.42 | 0.83 |
| 29 | 0.014 | 0.89 |
| 30 | 0.116 | 0.93 |
| 31 | 0.005 | 1.0 |
| 32 | 0.09 | 0.62 |
| 33 | 0.037 | 1.17 |
| 34 | 0.0008 | 1.0 |
| 35 | 0.125 | 0.51 |
| 36 | 0.005 | 0.91 |
| 37 | 0.006 | 0.87 |

Based on these results, representative compounds of this invention have been shown to be selective $\beta_3$-AR agonists. They are therefore useful in treating metabolic disorders related to insulin resistance or hyperglycemia (typically associated with obesity or glucose intolerance), atherosclerosis, gastrointestinal disorders, neurogenic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, and severity of the condition being treated, as well as the various physical factors related to the individual being treated. As used in accordance with this invention, satisfactory results may be obtained when the compounds herein are administered at a daily dosage of 0.1 mg to 1 mg per kilogram of body weight, preferably in divided doses two to six times per day, or in a sustained release form. For most large mammals, the total daily dosage is from 3.5 mg to 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidinone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for administration by syringe include sterile aqueous solutions or dispersions and sterile powders for the extemporaneous preparation of sterile injectable solutions or dispersions. The form must be sufficiently fluid to permit administration by syringe. It must be stable under the conditions of manufacture and storage and must be preserved against the contaminating action of microorganisms. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds herein with a sufficient amount of animal feed to provide from 1 to 1000 ppm of the compound in the feed. Animal feed supplements can be prepared by admixing 75% to 95% by weight of a compound of this invention with 5% to 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. When the supplement is used as a top dressing for the feed, the carrier likewise helps to ensure a uniform distribution of the active compound across the top of the dressed feed.

The preferred medicated swine, cattle, sheep and goat feed generally contain from 0.01 to 400 grams of active ingredient per ton of feed, the optimum amount for these animals usually being 50 to 300 grams per ton of feed. The preferred poultry and domestic pet feed usually contain 0.01 to 400 grams and preferably 10 to 400 grams of active ingredient per ton of feed.

For parenteral administration, the compounds described herein may be prepared in the form of a paste or a pellet and administered as an implant, usually under the skin of the head or ear of the animal in which an increase in lean meat deposition and/or an improvement in lean meat to fat ratio is sought. Parenteral administration involves injection of a sufficient amount of the compounds of the present invention to provide the animal with 0.001 to 100 mg/kg/day of body weight of the active ingredient. The preferred dosage for swine, cattle, sheep and goats is in the range of 0.001 to 50 mg/kg/day of body weight of active ingredient. The preferred dosage for poultry and domestic pets is usually in the range of 0.001 to 35 mg/kg/day of body weight.

Paste formulations can be prepared by dispersing the active compounds in pharmaceutically acceptable oils such as peanut oil, sesame oil, corn oil or the like. Pellets containing an effective amount of the compounds herein can be prepared by admixing these compounds with a diluent such as carbowax, carnuba wax, and the like, and a lubricant, such as magnesium or calcium stearate, can be added to improve the pelletizing process. It is recognized that more than one pellet may be administered to an animal to achieve the necessary dosage that will provide the desired increase in lean meat deposition and/or improvement in lean meat to fat ratio. Moreover, it has been found that implants may also be employed periodically during the animal treatment period in order to maintain the proper drug level in the animal's body. For poultry and swine farmers, the method of this invention results in leaner animals.

The compounds of this invention are also useful in elevating the lean mass to fat ratio in domestic pets. For the pet owner or veterinarian who wishes to increase leanness and trim unwanted fat from pets, the present invention provides the means by which this can be accomplished.

The preparation of representative examples of this invention is described below.

EXAMPLE 1

3-Butylamino-4-(4-{2-[(2R)-2-(3-chloro-phenyl)-2-hydroxy-ethylamino]-propyl}-phenylamino)-cyclobut-3-ene-1,2-dione Step A The 4-nitrophenyl-2-propylamine hydrochloride salt (4) (8.84g, 40.8mmol) was dissolved in 2:1 t-butyl alcohol/water (70 mL) solution. The temperature was reduced to 0 ° C., and potassium carbonate (10.7g, 77.5 mmol) was added followed by di-t-butoxycarbonyl (8.9 g, 40.8 mmol). The reaction was allowed to slowly reach room temperature while maintained under nitrogen atmosphere. After two hours, the reaction was concentrated under reduced pressure and the residue dissolved in ethyl acetate (200 mL), washed with water (200 mL) and dried with anhydrous potassium carbonate. The solution was filtered and concentrated under reduced pressure to afford (11.8 g) of an orange solid. The solid was purified using flash chromatography with a gradient solvent system of 20% ethyl acetate-hexane and increased to 40% ethyl acetate-hexane. 10.6 g (93%) of the purified product was obtained by recrystallization with hexane-ethyl acetate. $^1$HNMR (DMSO-$d_6$, 200 MHz) Rotamer 1: δ 0.9 (d, 3H, C$\underline{H}_3$), 1.2 (s, 9H, C(C$\underline{H}_3$)$_3$), 2.6–3.0 (overlapping m, 2H, C$\underline{H}_2$), 3.7 (m, 1H, C$\underline{H}$), 6.8 (overlapping d, 1H. N$\underline{H}$), 7.5 (t, 2H, Ar$\underline{H}$), 8.2 (d, 2H, Ar$\underline{H}$). Rotamer 2: δ 1.1 (d, 3H, C$\underline{H}_3$), (s, 9H, C(C$\underline{H}_3$)$_3$), 2.6–3.0 (overlapping m, 2H, C$\underline{H}_2$), 3.7 (m, 1H, C$\underline{H}$), 6.8 (overlapping d, 1H, N$\underline{H}$), 7.5 (t, 2H, Ar$\underline{H}$), 8.2 (d, 2H, Ar$\underline{H}$).

Step B

The BOC protected 4-nitrophenyl-2-propylamine 5 (1.9 g, 6.78 mmol) was dissolved in (45 mL) ethanol and added to a Parr flask containing 3% palladium on carbon (0.190g, 10% by wt.). The reaction mixture was treated with $H_2$ at a pressure under 25 psi for 2.5 hours. The solution was filtered over celite and the filtrate concentrated under reduced pressure to afford 1.55 g of a yellow solid. The crude reaction mixture was purified by flash chromatography eluting with 50% ethyl acetate-hexane to yield a yellow solid (6) (1.41 g, 83%). $^1$HNMR (CDCl$_3$, 300 MHz) δ1.2 (d, 3H, C$\underline{H}_3$), 1.3 (s, 9H, C(C$\underline{H}_3$)$_3$, 2.6 (m, 1H, C$\underline{H}$H), 2.8 (m, 1H, C$\underline{H}$H), 4.2 (m, 1H, C$\underline{H}$), 6.6 (d, 2H, Ar$\underline{H}$), 7.0 (d, 2H, Ar$\underline{H}$), 3 exchangeable protons were diffuse.

Step C

The BOC protected aniline compound 6 (0.750 g, 2.99 mmol) was taken up in 1 mL of THF and 3,4-diethoxy-3-cyclobutene-1,2-dione (0.56 g, 3.30 mmol) was added under nitrogen at room temperature. After 24 hours, the solution was concentrated under reduced pressure to afford 1.279 g of an orange solid. The solid was purified by flash chromatography using a gradient solvent system of 20% ethyl acetate-hexane and increasing to 40% ethyl acetate-hexane. A white solid (7) (0.969 g, 88%) was obtained. $^1$HNMR (CDCl$_3$, 300 MHz) δ1.1 (d, 3H, C$\underline{H}_3$), 1.4 (s, 9H, C(CH$_3$)$_3$), 1.5 (t, 3H, CH$_2$C$\underline{H}_3$), 2.6 (m, 1H, C$\underline{H}$H), 2.8 (m,1H, C$\underline{H}$H), 3.8 (broad s, 1H, NC$\underline{H}$) 4.2 (broad s,1H, N$\underline{H}$CH), 4.9 (q, 2H, OC$\underline{H}_2$), 7.2 (d, 2H, Ar$\underline{H}$), 7.3 (d, 2H, Ar$\underline{H}$), 8.2 (broad s, 1H, ArN$\underline{H}$).

Step D

The BOC protected ethoxy squarate compound 7 (580 mg, 1.6 mmol) was dissolved in 10 ml of ethanol and butylamine (125 mg, 1.7 mmol) was added at room temperature. A white solid immediately precipitated and after 4h the solid was filtered. The solid was triturated with hexane and dried on a vacuum pump to afford 550 mg (89%) of a white solid (8 $R^3$=n-butyl). Mp 229–231° C.(dec). IR (KBr): 3350 (br m), 1800 (s), 1570 (s), 1191 (s) cm$^{-1}$. $^1$HNMR (DMSO-d$_6$, 400 MHz) δ0.90 (t, 3H, J=7.5 Hz, CH$_2$CH$_3$), 0.98 (d, 3H, J=6.6 Hz CHCH$_3$), 1.31–1.37 (m, 2H, CH$_2$CH$_2$), 1.33 (s, 9H, C(CH$_3$)$_3$), 1.53 (m, 2H, NCH$_2$CH$_2$), 2.49 (m, 1H, CHH), 2.65 (m, 1H, CHH), 3.56 (m, 2H, NCH$_2$), 3.59 (m, 1H CHCH$_3$), 6.73 (d, 1H, J=8.4 Hz, NHCH), 7.1 (d, 2H, J =8.6 Hz, ArH), 7.32 (d, 2H, J=8.6 Hz, ArH), 7.6 (broad s, 1H, NH$_2$), 9.53 (broad s, 1H, ArNH).

Step E

To a slurry of 8 ($R^3$=n-butyl) (0.33 g, 0.82 mmol) in methylene chloride (6 mL) was added trifluoroacetic acid (1.12 gm, 9.9 mmol) at room temperature under nitrogen. After 5 hours, the reaction was concentrated under reduced pressure and the residue dissolved in methanol. Sodium bicarbonate (12 mL) was added and a white solid precipitated. The aqueous layer was extracted twice with CH$_2$Cl$_2$, then with 50 ml of 4:1 CH$_2$Cl$_2$-methanol. The organic layers were combined, dried (Na$_2$SO$_4$) and the solvents removed at reduced pressure to yield 0.19 gm (77%) of a white solid. This was used without further purification. $^1$HNMR (DMSO-d$_6$, 300 MHz) δ0.85–1.06 (m, 6H, CH$_2$CH$_3$, CHCH$_3$), 1.38 (m, 2H, CH$_2$CH$_2$CH$_3$), 1.60 (m, 2H, NCH$_2$CH$_2$), 2.56 (m, 1H, ArCH$_2$), 3.06 (m, 2H, ArCH$_2$), 3.65 (m, 3H, NCH$_2$, CHCH$_3$), 7.17 (d, 2H, J=8.5 Hz, NArH), 7.35 (d, 2H, J=8.5 Hz, CH$_2$ArH), 7.86 (br s, 1H, ArNH), three exchangeable resonances not distinctly observed via $^1$HNMR.

Step F

To a solution of 0.19 gm (0.63 mmol) of the amine from Example 1, Step E in 2 mL of dimethyl formamide (DMF) was added 0.11 gm (0.73 mmol) of (S)-3-chlorophenyl-oxirane. The reaction mixture was allowed to stir at 80° C. for 24h. The mixture was cooled to room temperature and added to 12 mL of water. The aqueous layer was extracted three times with 100 mL of CH$_2$Cl$_2$. The combined organic layers were washed with 50 mL of water, and the organic layer was dried (anhyd. Na$_2$SO$_4$) and the solvents removed at reduced pressure. The residue was triturated with ethyl acetate-hexanes (1:2) and filtered to yield 0.12 gm (42%) of a white solid. Mp 176–179 ° C. IR (KBr) 3410 (br s), 3190 (s), 1760 (s), 1573 (m) cm$^{-.}$ $^1$HNMR (DMSO-d$^6$, 400 MHz) δ0.92 (m, 6H, CH$_2$CH$_3$, CHCH$_3$), 1.34 (m, 2H, CH$_2$CH$_2$CH$_3$), 1.54 (m, 2H, CH$_2$CH$_2$CH$_3$), 2.43 (m, 1H, ArCH$_2$), 2.6–2.86 (m, 4H, ArCH$_2$, NHCHCH$_3$, NHCH$_2$CH$_2$), 3.58 (q, 2H, J=6.15 Hz, CH(OH)CH$_2$NH), 4.61 (m, 1H, CHOH), 5.47 (br s, 1H, CH(CH(CH$_3$)NH), 7.11 (M, 2H, ArH), 7.25–7.36 (m, 6H, ArH), 7.71 (br s, 1H, CH$_2$NH), 9.66 (br s, 1H, ArNH). MS (EI) m/z: M$^+$, 455.

EXAMPLE 2

(1R)-1-(3-Chloro-phenyl)-2-{1-methyl-2-[3-(4-octylamino-1,1-dioxo-1H-1-.lambda.(6).-[1,2,5] thiadiazol-3-ylamino)-phenyl-]-ethylamino}-ethanol Step A A solution of 3.03g (12.1 mmol) of the BOC-protected aniline 11 was dissolved in 25 mL of ethanol. 2.5g of 3,4-diethoxy-1,1-dioxo-1,2,5-thiadiazole, 12.1 mmol) was added and the reaction was heated to 60° C. and stirred under nitrogen. After stirring at 60° C. for 24 hours, a yellow precipitate formed whereby the solvent was reduced and a yellow solid, compound 12, (4.917 g, 99%) was isolated. $^1$H NMR (DMSO-d$_6$, 300 HMz): δ 1.0 (d, 3H, NCHCH$_3$), 1.3 (s, 9H, (CH$_3$)$_3$), 1.5 (t, 3H, OCCH$_2$CH$_3$), 2.45–2.75 (m, 2H, ArCH$_2$), 3.6 (m, 1H, CHCH$_3$), 4.6 (q, 2H, OCH$_2$), 6.8 (d, 1H, ArNH), 7.2 (d, 2H, ArHCH$_2$), 7.7 (d, 2H, NArH), 10.9 (s, 1H, NHCO).

Step B

Compound 12 (2.0 g, 4.87 mmol) was dissolved in ethanol and octylamine (1.05 ml, 6.33 mmol) was added. The reaction was heated to 50° C. and stirred under nitrogen. A white precipitate immediately formed. The reaction was concentrated under reduced pressure to yield compound 13 ($R^3$ is octyl), (2.45 g, 100%) as a white solid. $^1$H NMR (DMSO-d$_6$, 300 MHz): δ (m, 3H, CH$_2$CHj$_3$), 1.0 (d, 3H, CHCH$_3$), 1.25 (m, 10H, (CH$_2$)$_5$), 1.3 (s, 9H, (CH$_3$)$_3$), 1.6 (m, 2H, NCH$_2$CH$_2$), 2.5–2.75 (m, 2H, CH$_2$Ar), 3.4 (m, 2H, NCH$_2$), 3.6 (m, 1H, CHCH$_3$), 6.8 (d, 1H, ArNH), 7.25 (d, 2H, CH$_2$ArH), 7.6 (d, 2H, NArH), 8.85 (s, 1H, HNCH$_2$), 10.35 (s, 1H. NHCO).

Step C

The BOC protected compound 13 (2.45 g, 4.87 mmol) was dissolved in 20 mL of methylene chloride to form a slurry. Trifluroacetic acid (4.5 mL, 58.4 mmol) was added at room temperature and stirred under nitrogen. After 96 hours, the solvent was removed under reduced pressure and the residue taken up in saturated aqueous sodium carbonate. The resulting solid was filtered to yield (1.7 g, 89%) of a white solid. This was used without further purification. $^1$H NMR (DMSO-d$_6$, 300 MHz): δ0.8 (m, 3H, CH$_2$CH$_3$), 1.1 (d, 3H, CHCH$_3$), 1.25 (s, 10H, (CH$_2$)$_5$), 1.55 (s, 2H, NCH$_2$CH$_2$), 2.4–2.9 (m, 2H, CH$_2$Ar), 3.2 (t, 2H, NCH$_2$), 3.3 (m, 1H, CHCH$_3$), 7.05 (d, 2H, CH$_2$ArH), 7.45 (d, 2H, NArH), 4 exchangeable resonances not distinctly observed via $^1$H NMR.

Step D

The amine from Step C (0.575 g, 146 mmol) was dissolved in (1 mL) N,N-dimethylformamide 0.24 mL of (S)-3-chlorophenyl-oxirane (1.90 mmol) was added. The reaction was warmed to 70° C. under nitrogen. After 24 hours, the reaction was poured into water (100 mL) and extracted with ethyl acetate (2x100 mL). The combined organic layers were washed with water (200 mL), dried (Na$_2$SO$_4$), filtered and concentrated at reduced pressure to yield an amber oil. Flash chromatography using a gradient solvent system of 2%–10% methanol-methylene chloride yielded the titled compound (0.181 g, 23%) as a yellow solid. Mp 90–96° C. IR(KBr): 3400 (m), 2875 (s), 1625 (s), 1200 (s) cm$^{-1}$. $^1$HNMR (DMSO-d$_6$, 400 MHz): δ0.9 (t, J=6.7 Hz, 3H, CH$_2$CH$_3$), 1.1 (d, J=6.6 Hz, 3H, CHCH$_3$), 1.3 (s, 10H, (CH$_2$)$_5$), 1.6 (s, 2H, NCH$_2$CH$_2$), 2.6–3.0 (overlapping m, 2H, CH$_2$Ar), 3.0 (overlapping m, 2H, HCH$_2$N), 3.2 (m, 1H. CHCH$_3$), 3.4 (m, 2H, NCH$_2$CH$_2$), 4.8 (m, 1H, OH), 6.9 (s, 1H, CHOH), 7.2–7 (overlapping m, 8H, ArH), Three exchangeable resonances not distinctly observed via $^1$HNMR. HRMS (FAB) Calcualted mass: 548.24532 mmu measured mass: 548.25961 mmu. Analysis calc. for C$_{27}$H$_{39}$N$_5$O$_3$SCl: C, 59.16; H, 6.99; N, 12.78; Found: C, 58.36; H, 6.94; N, 11.92.

EXAMPLE 3

(1R)-1-(3-Chloro-phenyl)-2-{1-methyl-2-[4-(octylamino-1,1-dioxo-1H-1-.lambda.(6).-1,2,5] thiadiazol-3-ylamino)-phenyl]-ethylamino}-ethanol Step A In 15 mL of ethanol was added 0.52 gm (2.08 mmol) of the aniline 6 from Step B, Example 1, and 0.47 gm (2.28 mmol) of 3,4-diethoxy-1,1-dioxo-1,2,5-thiadiazole. The reaction mixture was allowed to stir at 70° C. for 24h. The mixture was cooled to 0° C. and 3 mL of hexanes was added. The white precipitate was filtered and dried under vacuum to yield 0.71 gm (84%) of 14. $^1$HNMR (CDCl$_3$, 300 MHz) δ 1.02 (d, 3H, J=6.65 Hz, CHC$\underline{H}_3$), 1.34 (s, 9H, C(C$\underline{H}_3$)$_3$), 1.50 (t, 3H, J=7.1 Hz, OCH$_2$C$\underline{H}_3$), 2.65 (m, 2H, ArC$\underline{H}_2$), 3.21 (s, 2H, C(O)N$\underline{H}$, ArN$\underline{H}$), 3.75 (m, 1H, C$\underline{H}$CH$_3$), 4.60 (q, 2H, J=7.1 Hz, OC$\underline{H}_2$CH$_3$), 7.16 (d, 2H, J=8.51 Hz, Ar$\underline{H}$), 7.62 (d, 2H, J=8.51 Hz, Ar$\underline{H}$), 7.62 (d, 2H, J=8.51 Hz, Ar$\underline{H}$).

Step B

In 8 mL of ethanol was dissolved 0.35 gm (0.85 mmol) of compound 14 from Example 3, Step A, and 0.143 gm (1.105 mmol) of octylamine. The reaction mixture was stirred at 60° C. for 24h. The solvent was removed under reduced pressure and the residue was triturated with 4 mL of 3:1 hexanes-ethyl acetate to yield 0.35 gm (84%) of a white solid (15 R =n-octyl), which was used without further purification.

Step C

To a mixture of 0.35 gm (0.71 mmol) of 15 from Example 3, Step B, in 6 mL of CH$_2$Cl$_2$ was added 0.97 gm (8.5 mmol) of trifluoroacetic acid (TFA). The mixture turned into a homogeneous solution and was stirred at room temperature for an additional 6h. The solvents were removed at reduced pressure and the residue was re-dissolved in 5 mL of methanol. 3 mL of saturated NaHCO$_3$ was added. The solvents were removed under reduced pressure and the residue was triturated with 3 mL of water. The solid isolated was dried and used without further purification or characterization.

Step D

To a mixture of the product from Step C, Example 3, (0.22 gm, 0.58 mmol) in 1 mL of DMF was added 0.098 gm (0.63 mmol) of the (S)-3-chlorophenyl-oxirane. The mixture was allowed to stir at 70° C. for 24h. The solution was cooled and the solvent removed under reduced pressure. Chromatography of the residue on silica gel using a solvent gradient of 2%–7% methanol-chloroform yielded 0.110 gm (36%) of a light yellow solid. Mp 89–92 ° C. IR (KBr) 3360 (br m), 3921 (s), 1645 (s), 1599 (s), 1158 (m). $^1$HNMR (DMSO-d$^6$, 400 MHz) 6 0.85 (t, 3H, J=6.59 Hz, CH$_2$C$\underline{H}_3$), 1.02 (d, 3H, J=6.15 Hz, CHC$\underline{H}_3$), 1.25 (br s, 10H, NCH$_2$CH$_2$(C$\underline{H}_2$)$_3$CH$_3$), 1.60 (m, 2H, NCH$_2$C$\underline{H}_2$), 2.55 (m, 1H, ArC$\underline{H}_2$), 2.8–3.4 (br m, 6H, ArC$\underline{H}_2$, NHC$\underline{H}_2$, C$\underline{H}$CH$_3$, C(OH)C$\underline{H}_2$NH), 4.74 (m, 1H, C$\underline{H}$OH), 7.13 (m, 2H, Ar$\underline{H}$), 7.33 (m, 3H, Ar$\underline{H}$), 7.43 (s, 1H, Ar$\underline{H}$), 7.57 (d, 2H, J=7.7 Hz, Ar$\underline{H}$), four exchangeable resonances not distinctly observed via $^1$HNMR.

EXAMPLE 4

4-((2S)-3-{1,1-Dimethyl-2-[4-(4-octylamino-1,1-dioxo-1H-1(lambda(6))-1,2,5]thiadiazol-3ylamino-phenyl[-ethylamino}-2-hydroxy-propoxy)-phenol Step A A mixture of 2.0 gm (8.9 mmol) of 2,4'-dinitro-2-methyl-propylbenzene and 200 mg of a 10% palladium on carbon in 30 mL of ethanol was hydrogenated at 50 psi and room temperature for 48 h. The reaction mixture was filtered through celite and the celite was washed with 200 mL of ethanol. The solvents were removed at reduced pressure and the residue added to 15 mL of ethyl acetate containing 2.3 equivalents of HCl. The precipitate was filtered and washed with 2 mL of ethyl acetate. This solid was then dissolved in 30 mL of 1 M NaOH and extracted with 300 mL of CH$_2$Cl$_2$. The organic layer was dried (anhyd. Na$_2$SO$_4$) and the solvent removed under reduced pressure to yield 1.12 gm (77%) of an oil. This was used without further purification. $^1$HNMR (CDCl$_3$, 300 MHz) δ 1.49 (s, 6H, C(C$\underline{H}_3$)$_2$), 2.53 (s, 2H, ArC$\underline{H}_2$), 3.58 (br s, 2H, exchangeables), 6.62 (d, 2H, J=7.6 Hz, Ar$\underline{H}$), 6.96 (d, 2H, J=7.6 Hz, Ar$\underline{H}$), two exchangeable resonances not distinctly observed via $^1$HNMR.

Step B

To a solution of 1.49 gm (6.8 mmol) of di-t-butyl carbonate in 100 mL of CH$_2$Cl$_2$ at 0° C. was added 1.12 gm (6.8 mmol) of 2,4'-diamino-2-methylpropylbenzene in 10 mL of CH$_2$Cl$_2$. The reaction mixture was allowed to stir at 0° C. for 3 h and then at room temperature for 18 h. The solvents were removed at reduced pressure and the residue chromatographed on silica gel using a solvent gradient of 5:1 to 4:1 hexanes-ethyl acetate to yield 1.3 gm (73%) of an off white solid. $^1$HNMR (CDCl$_3$, 300 MHz) δ1.25 (s, 6H, NHC(C$\underline{H}_3$)$_2$), 1.46 (s, 9H, C(C$\underline{H}_3$)$_3$), 2.83 (s, 2H, ArC$\underline{H}_2$), 3.6 (br s, 2H, N$\underline{H}_2$), 4.29 (br s, 1H, N$\underline{H}$), 6.62 (d, 2H, J=7.2 Hz, Ar$\underline{H}$), 6.95 (d, 2H, J=7.2 Hz).

Step C

To a solution 1.3 gm (4.9 mmol) of the aniline from Example 4, Step B, in 25 mL of ethanol was added 1.01 gm (4.9 mmol) of 3,4-diethoxy-1,1-dioxo-1,2,5-thiadiazole. The reaction mixture was allowed to stir at 70° C. for 24h. The solvents were removed at reduced pressure and the residue was recrystallized from hot ethyl acetate-hexanes to yield 1.79 gm (85%) of a white solid. $^1$HNMR (CDCL$_3$, 300 MHz) δ 1.26 (s, 6H, C(C$\underline{H}_3$)$_2$, 1.47 (s, 9H, OC(C$\underline{H}_3$)$_3$, 1.58 (t, 3H, J=7.1 Hz, OCH$_2$C$\underline{H}_3$), 3.02 (s, 2H, ArC$\underline{H}_2$), 4.24 (br s, 1H, N$\underline{H}$C(O)), 4.7 (q, 2H, J=7.1 Hz, OC$\underline{H}_2$CH$_3$), 7.22 (d, 2H, J=8.4 Hz, Ar$\underline{H}$), 7.58 (br s,1H. ArN$\underline{H}$), 7.6 (d, 2H, J =8.4 Hz, Ar$\underline{H}$).

Step D

To a solution of 0.6 gm (1.41 mmol) of the ethoxy substituted compound from Example 4, Step C, in 15 mL of ethanol was added 0.18 gm (1.41 mmol) of octyl amine. The reaction mixture was allowed to stir at 70° C. for 24h. The solvents were removed at reduced pressure and the residue was triturated with isopropyl ether to yield 0.51 gm (72%) of a white solid. $^1$HNMR (CDCl$_3$, 300 MHz) δ0.84 (t, 3H, J=4.2 Hz, CH$_2$C$\underline{H}_3$), 1.35 (br s, 16H, C(C$\underline{H}_3$)$_2$, NCH$_2$CH$_2$(C$\underline{H}_2$)$_5$CH$_3$), 1.71 (br s, 2H, NHCH 2 C$\underline{H}_2$), 2.95–3.05 (m, 2H, ArC$\underline{H}_2$), 3.42 (br s, 2H, NHC$\underline{H}_2$CH$_2$), 7.03 (d, 2H, J=8.2 Hz, Ar$\underline{H}$), 8.58 (br s,1H, OC(O)N$\underline{H}$), 10.03 (br s,1H, N$\underline{H}$CH$_2$).

Step E

To a solution of 0.51 gm (1.0 mmol) of the Boc-protected amine from Example 4, Step D, in 12 mL of CH$_2$Cl$_2$ was added 1.37 gm (12 mmol) of trifluoroacetic acid. This was allowed to stir at room temperature for 18h. The solvents were removed under reduced pressure and the residue was dissolved in 3 mL of methanol. Saturated NaHCO$_3$ (3–4 mL) was added dropwise and the solvents removed at reduced pressure. 4 mL of H$_2$O was added and the aqueous solution extracted twice with CHCl$_3$. The combined organic layers were dried (Na$_2$SO$_4$) and the solvents removed at reduced pressure. The solid (0.40 gm) was used as is without further characterization or purification.

(2S)-1-(4-Benzyloxy-phenoxy)-3-{1,1-dimethyl-2-[4-(4-octylamino-1,1-dioxo-1H-1-.lambda(6).-1,2,5]thiadiazol-3-ylamino)-phenyl]-ethylamino}-propan-2-ol Step F To a solution of 0.4 gm (0.98 mmol) of the amine from Example 4, Step E, in 5 mL of DMF was added 0.25 gm (0.98 mmol) of (2S)-2-(4-benzyloxy-phenoxymethyl)-oxirane (28). The reaction mixture was heated to 70° C. for 48h. The reaction mixture was cooled to room temperature and the solvents were removed at reduced pressure. Chromatography on silica gel using a gradient of 8%–10% methanol-methylene chloride as a solute yielded 0.39 gm (60%) of a light yellow solid. Mp 105–107° C. IR (KBr) 3390 (br d), 2930 (d), 1642 (s), 1503 (s), 1235 (s), 1153 (d) $cm^{-1}$. $^1$HNMR (DMSO-$d^6$, 400 MHz) δ 0.86 (t, 3H, J=7.03 Hz, $CH_2C\underline{H}_3$),1.16 (br s, 6H, C($C\underline{H}_3$)$_2$), 1.27 (br d, 10H, $NCH_2CH_2(C\underline{H}_2)_5CH_3$), 1.60 (m, 2H, $NCH_2C\underline{H}_2$), 2.78 (br s, 2H, $OC\underline{H}_2C(OH)$), 2.89–3.10 (br m, 2H, $C(OH)C\underline{H}_2NH$), 3.18–3.34 (br s, 2H, $ArC\underline{H}_2C(CH_3)_2$), 3.92 (m, 2H, $NC\underline{H}_2CH_2$), 3.99 (br s, 1H, $OCH_2C\underline{H}(OH)$), 5.04 (s, 2H, $ArC\underline{H}_2OAr$), 6.87–6.96 (m, 4H $Ar\underline{H}$), 7.15 (br s, 2H, $Ar\underline{H}$), 7.30–7.44 (m, 5H, $Ar\underline{H}$), 7.55 (d, 2H, J=7.5 Hz, $Ar\underline{H}$), four exchangeable resonances not distinctly observed via $^1$HNMR.

Step G

To a solution of 0.36 gm (0.53 mmol) of the benzyl protected from Example 4, Step F, in 11 mL of ethanol was added 0.036 gm of 10% palladium on carbon. This was stirred at room temperature under hydrogen at ambient pressure for 48h. The reaction mixture was filtered through celite which was washed with methanol. The organic solvents were removed under reduced pressure and the residue was chromatographed on silica gel using a gradient of 8%–10% methanol-methylene chloride as an eluent to yield an oil (0.3 gm). The oil was dissolved in methanol and gaseous HCl was added. The solvents were removed under reduced pressure and the residue crystallized from isopropanol-hexanes to yield a tan solid. Mp 229.5–231.3° C. IR (KBr) 3400 (br s), 2910 (m), 1649 (m), 1142 (m). $^1$HNMR (DMSO-$d^6$, 400 MHz) δ 6 0.84 (t, 3H, J=6.6 Hz, $CH_2C\underline{H}_3$), 1.21 (br s, 6H, C($C\underline{H}_3$)$_2$), 1.25–1.61 (br m, 10H, $N(CH_2)_2(C\underline{H}_2)_5CH_3$), 1.64 (m, 2H, $NCH_2C\underline{H}_2$), 2.98 (br s, 2H, $ArC\underline{H}_2C(CH_3)_2$), 3.02–3.27 (m, 2H, $OC\underline{H}_2CH(OH)$), 3.36 (m, 2H, $NC\underline{H}_2CH_2$), 3.90 (m, 2H, $CH(OH)C\underline{H}_2NH$), 4.10 (m, 1H, $CHO\underline{H}$), 5.82 (d, 1H, J=4.8 Hz, $CHO\underline{H}$), 6.68 (m, 2H, $Ar\underline{H}$), 6.79 (m, 2H, $Ar\underline{H}$), 7.30 (d, 2H, J=8.57 Hz, $Ar\underline{H}$), 7.86 (d, 2H, J=8.57 Hz, $Ar\underline{H}$), 8.46 (m, 1H, $CH_2N\underline{H}$), 8.58 (m, 1H, $\underline{H}Cl$ salt), 8.95 (s, 1H, $ArO\underline{H}$), 10.06 (t, 1H, J=4.6 Hz, $CH_2CH_2N\underline{H}$), 11.56 (s, 1H, $ArN\underline{H}$). Analysis calc. for $C_{29}H_{44}ClN_5O_5S$: C, 57.08; H, 7.27; N, 11.48.

Found: C, 56.78; H, 7.34; N, 11.36.

EXAMPLE 5

4-((2S)-2-Hydroxy-3-{2-[4-(4-octylamino-1,1-dioxo-1H-1.lambda(6).-[1,2,5]thiadiazol-3-ylamino)-phenyl]-ethylamino}-propoxy)-phenol Step A To a solution of 10.0 gm (73.4 mmol) of commercially available 2-(4-aminophenyl)ethylamine in 370 mL of methylene chloride at 0° C. was added 16.0 gm (73.4 mmol) of di-tert-butyl dicarbonate. The reaction mixture was allowed to slowly warm to room temperature while stirring under $N_2$. After 24 hours, the reaction was concentrated under reduced pressure and purified via flash chromatography using an isocratic solvent system of 9.5:3:2 methylene chloride:methanol:hexane respectively, to yield 9.0 gm (52%) of the product. $^1$HNMR (DMSO-$d_6$, 300 MHz) δ 1.4 (s, 9H, C($C\underline{H}_3$)3), 2.5 (m, 2H, $NC\underline{H}_2$), 3.05 (m, 2H, $ArC\underline{H}_2$), 4.9 (s, 2H, $N\underline{H}_2$), 6.5 (d, 2H, J=8.9 Hz, $Ar\underline{H}$), 6.8 (overlapping m, 2H, $Ar\underline{H}$), 6.8 (overlapping m, 1H. $N\underline{H}$).

Step B

The 1.15 gm (4.85 mmol) of the BOC protected phenethyl amine from Example 5, Step A, was combined with 1.0 gm (1.45 mmol) of 3,4-diethoxy-1,1-dioxo-1,2,5-thiadiazole in 10 mL of ethanol at 70° C. The reaction stirred under $N_2$ and after 0.5 hour, a precipitate formed. The solvent was removed at reduced pressure to yield 1.9 gm (99%) of a yellow solid. $^1$HNMR (DMSO-$d_6$, 300 MHz) δ 1.4 (s, 9H, C($C\underline{H}_3$)$_3$), 1.5 (t, 3H, $OCH_2C\underline{H}_3$), 2.7 (t, 2H, $NC\underline{H}_2$), 3.1 (q, 2H, $ArC\underline{H}_2$), 4.6 (q, 2H, $OC\underline{H}_2$), 6.9 (m, 1H, $N\underline{H}$), 7.3 (d, 2H, $Ar\underline{H}$), 7.75 (d, 2H, J=8.9 Hz, $Ar\underline{H}$), 11.0 (broad s, 1H, $N\underline{H}$). MS (LC) m/z: $M^-$, 395.

Step C

To 1.4 gm (3.5 mmol) of the BOC protected thiodiazole dioxide from Example 5, Step B was combined with 0.59 gm (4.6 mmol) of octylamine in 7.3 mL of ethanol. The temperature was increased to 50° C. and stirred under Nitrogen. The reaction mixture was stirred for 4 h a white precipitate formed and the solvent was removed at reduced pressure to yield 1.69 cm (100%) of a white solid. $^1$HNMR (DMSO-$d_6$, 300 MHz) δ0.9 (m, 3H, $CH_2C\underline{H}_3$), 1.3 (m, 10H, ($C\underline{H}_2$)$_5$), 1.4 (s, 9H, $C\underline{H}_3$)$_3$), 1.6 (m, 2H, $NCH_2C\underline{H}_2$), 2.7 (t, 2H, $NC\underline{H}_2CH_2Ar$), 3.2 (q, 2H, $C\underline{H}_2Ar$), 3.4 (m, 2H, $NC\underline{H}_2(CH_2)_6$), 6.9 (m, 1H. $N\underline{H}$), 7.3 (d, 2H, J=8.9 Hz, $Ar\underline{H}$), 7.7 (d, 2H, J=8.9 Hz, $Ar\underline{H}$), 8.9 (broad s, 1H, $N\underline{H}$), 10.4 (broad s, 1H, $N\underline{H}$).

Step D

To 1.69 gm (3.52 mmol) of the coupled octylamine thiadiazole dioxide from Example 5, Step E in 8.2 mL of methylene chloride at room temperature, was added 4.82 gm (42.2 mmol) of trifluoroacetic acid. A precipitate quickly formed after 1 hour and the solvent was removed at reduced pressure. The residue was taken up in 5 mL of methanol and 18 ml of sodium bicarbonate was added. A solid precipitated and the solvents were removed at reduced pressure. 15 mL of $H_2O$ was added a solid precipitated, which was filtered and dried to yield 1.21 gm (91%) of a white solid. $^1$HNMR (DMSO-$d_6$, 300MHz) δ 0.9 (m, 3H, $CH_2C\underline{H}_3$), 1.3 (m, 10H, ($C\underline{H}_2$)$_5$), 1.6 (m, 2H, $NCH_2 C\underline{H}_2$), 2.8 (t, 2H, $NC\underline{H}_2CH_2Ar$), 3.0 (t, 2H, $NCH_2C\underline{H}_2Ar$), 3.4 (m, 2H, $NC\underline{H}_2(CH_2)_6$), 7.3 (d, 2H, J=8.9 Hz, $Ar\underline{H}$), 7.7 (d, 2H, J=8.9 Hz, $Ar\underline{H}$), 7.8 (broad s, 2H, $N\underline{H}_2$). Two exchangeable resonances not distinctly observable via $^1$HNMR.

Step E (2S)-1-(4-Benzyloxy-phenoxy)-3-{2-[4-(4-octylamino-1,1-dioxo-1H-1.lambda(6).-[1,2,5]thiadiazol-3-ylamino)-phenyl]ethylamino}-propan-2-ol To 1.20 gm (3.16 mmol) of the amine from Scheme 5, Step D was added 0.81 gm (3.16 mmol) of the (2S)-2-(4-benzyloxy-phenoxymethyl)-oxirane (28) in 15.8 mL of dimethylformamide at 75° C. under $N_2$. After 6 days, the solvent was removed under reduced pressure and the crude mixture was purified via flash chromatography. A gradient solvent system of 2%–10% methanol/methylene chloride was used as an eluent to yield 0.48 gm (24%) of a yellow solid. IR (KBr): 3350 (s), 2875 (m), 1650 (s), 1600 (s), 1525 (s), 1250 (m), 1125 (s). $^1$HNMR (DMSO-d$_6$, 400MHz) δ0.9 (m, 3H, CH$_2$CH$_3$), 1.3 (m, 10H, (CH$_2$)$_5$), 1.6 (m, 2H, NCH$_2$CH$_2$), 2.8 (overlapping m, 2H, NCH$_2$CH$_2$Ar), 2.8 (overlapping m, 2H, CHCH$_2$N), 3.0 (m, 2H, NCH$_2$CH$_2$Ar), 3.3 (m, 2H, NCH$_2$(CH$_2$)$_6$), 3.85 (d, 2H, J=5.49 Hz, ArOCH$_2$), 4.0 (broad m, 1H, CHOH), 5.0 (s, 2H, ArCH$_2$O), 6.8–7.0 (q, 4H, ArH), 7.2 (d, 2H, J=8.13 Hz, ArH), 7.3–7.4 (overlapping m, 5H, ArH), 7.6 (d, 2H, J=8.13 Hz, ArH). Four exchangeable resonances are not distinctly observed via $^1$HNMR. MS (ESI) m/z: 636 (M$^+$). Analysis calc. for C$_{34}$H$_{45}$N$_5$O$_5$S .0.5 H$_2$O: C, 63.33; H, 7.19; N, 10.86 Found: C, 63.18; H, 6.86; N, 10.82.

Step F

To a solution of 0.39 gm (0.61 mmol) of the benzyl protected product from Example 5, Step E in 5 mL of ethanol containing 0.037 mL of acetic acid was added to 0.078 gm of Pd/C catalyst and the reaction mixture was placed under a 1 atm hydrogen atmosphere at room temperature. The reaction stirred for 2 days and was filtered through celite and concentrated under reduced pressure. The solid was then triturated with diethyl ether to yield (0.29g, 88%) yellow solid. Mp 98° C. (dec) IR (KBr): 3400 (broad s), 2900 (s), 1650 (s), 1600 (s), 1550 (s), 1500 (s), 1450 (m), 1300 (s), 1225 (s),1150 (s), 925 (m), 825 (m), 650 (m). $^1$HNMR (DMSO-d$_6$, 400MHz) δ 0.9 (m, 3H, CH$_2$CH$_3$), 1.25 (m, 10H, (CH$_2$)5), 1.6 (m, 2H, NCH$_2$CH$_2$), 2.8 (overlapping m, 2H, NCH$_2$CH$_2$Ar), 2.8 (overlapping m, 2H, CHCH$_2$N), 3.0 (m, 2H, NCH$_2$CH$_2$Ar), 3.3 (m, 2H, NCH$_2$(CH$_2$)$_6$), 3.81 (d, 2H, J=5.49 Hz, ArOCH$_2$), 4.0 (broad m, 1H, CHOH), 5.0 (s, 2H, ArCH$_2$O), 6.8–7.0 (m, 4H, ArH), 7.16 (d, 2H, J=8.35 Hz, ArH), 7.54 (d, 2H, J=8.35 Hz, ArH). Five exchangeable resonances are not distinctly observed via $^1$HNMR. MS: (APCl) m/z: 544 (M$^-$). Analysis calc. for C$_{27}$H$_{39}$N$_5$O$_5$S.0.5 H$_2$O: C, 56.75; H, 7.06; N, 11.41 Found: C, 56.83; H, 7.27; N, 11.44.

EXAMPLE 6

N-[2-Hydroxy-5-((1R)-1-hydroxy-2-{1-methyl-2-[4-(4-octylamino-1,1-dioxo-1H-1(lambda(6))-[1,2,5] thiadiazol-3-ylamino}-ethyl)-phenyl]-methanesulfonamide Step A The amine synthesized in Example 3, Step C (0.575g, 1.46 mmol) was dissolved in THF (1 mL). N-[2-Benzyloxy-5-((1R)-2-iodo-1-triethylsilanyloxy-ethyl)-phenyl]-methanesulfonamide (0.786 g, 1.4 mmol) was added followed by N,N-diisopropylethylamine (0.244 mL, 1.4 mmol) and the reaction was heated to 100° C. under nitrogen. After 36 hours, reaction was cooled to room temperature added to methylene chloride (150 mL), washed with water (150 mL) and dried (Na$_2$SO$_4$). The solvents were removed under reduced pressure and the crude solid was purified using flash chromatography with a gradient solvent system of 5%–10% methanol-methylene chloride to yield 0.494 gm of a yellow solid (43%). $^1$HNMR (DMSO-d$_6$, 300 MHz): δ 0.4 (m, 6H, Si(CH$_2$CH$_3$)$_3$), 0.7–0.9 (overlapping m, 9H, Si(CH$_2$CH$_3$)$_3$), 0.7–0.9 (overlapping m, 3H, (CH$_2$CH$_3$), 0.95 (m, 3H, CHCH$_3$), 1.3 (s, 10H, (CH$_2$)5), 1.6 (m, 2H, NCH$_2$CH$_2$), 2.4–3.0 (broad overlapping m, 2H, ArCH$_2$), 2.4–3.0 (broad overlapping m, 1H, CHCH$_3$), 2.9 (overlapping s, 3H, SO$_2$CH$_3$), 3.3 (overlapping s, 2H, NCH$_2$CO), 3.3 (overlapping m, 2H, NCH$_2$CH$_2$), 4.7 ( br s, 1H, HCOSiEt$_3$), 5.2 (s, 2H, OCH$_2$), 7.1–7.25 (overlapping m, 4H, ArH), 7.25–7.45 (overlapping m, 5H, ArH), 7.5–7.7 (overlapping m, 4H, ArH), 8.9 (Broad s, 1H, NH) two exchangeable resonances not distinctly observed via $^1$HNMR. LCMS m/z 825 (M$^-$).

Step B

N-[2-Benzyloxy-5-((1R)-1-hydroxy-2-{1-methyl-2-[4-(4-octylamino-1,1-dioxo-1H-1(lambda(6))-[1,2,5] thiadiazol-3-ylamino)-phenyl]-ethylamino}-ethyl)-phenyl]-methanesulfonamide 490 mg (0.59 mmol) of the compound from Example 6, Step A was dissolved in tetrahydrofuran (6.5 mL) under nitrogen and 1.35 mL (1.36 mmol) of tetrabutylammonium fluoride (1M) in tetrahydrofuran was added. After 3 hours, the reaction was quenched with water (2 mL) at 0° C. 90 mL of water was added and was then extracted with ethyl acetate (100 mL) which was dried (MgSO$_4$) and the solvent removed at reduced pressure. The crude yellow foam was purified by flash chromatography with a gradient solvent system of 5%–10% methanol-methylene chloride to yield 0.30 gm (72%) of a yellow solid. Mp 101–106° C. IR (KBr): 3375 (broad m), 2900 (s), 1625 (s), 1310 (m), 1150 (s) cm$^{-1}$. $^1$HNMR (DMSO-d$_6$, 400 MHz): δ0.85 (m, 3H, CH$_2$CH$_3$), 1.05 (m, 3H, CHCH$_3$), 1.3 (m, 10H, (CH$_2$)$_5$), 1.6 (m, 2H, NCH$_2$CH$_2$), 2.5–2.9 (m, 2H, CH$_2$Ar), 2.9 (s, 3H, SO$_2$CH$_3$), 3.0 (m, 2H, NCH$_2$CH$_2$), 3.1–3.5 (broad m, 2H, OHCHCH$_2$), 3.1–3.5 (overlapping broad m, 1H, NCH), 4.8 (s, 1H, HCO), 5.2 (s, 2H, OCH$_2$), 5.9 (broad s, 1H, OH), 7.1–7.3 (overlapping m, 4H, ArH), 7.3 (m, 2H, ArH), 7.4 (t, 2H, ArH), 7.55 (d, 2H, ArH), 7.6 (m, 2H, ArH), 9.0 (broad s, 2H, NH) two exchangeable protons are not distinguishable. MS (ESI) m/z 713 (M$^+$). Analysis calc. for C$_{35}$H$_{48}$N$_6$O$_6$S$_2$.1 H$_2$O: C, 57.51; H, 6.89; N, 11.50 Found: C, 57.33; H, 6.51; N, 11.46.

Step C 224 mg, (0.31 mmol) of the compound from Example 6, Step C was dissolved in ethanol (6 mL) and 10% palladium on carbon (10% by weight, 22 mg) was added and the reaction stirred at room temperature under hydrogen at room pressure. After 3 hours, the reaction was filtered through celite, which was washed with ethanol and the filtrate was concentrated at reduced pressure to yield a yellow solid. The product was purified by flash chromatography using a solvent system of 10% methanol-methylene chloride to yield 157 mg (80%) of a yellow solid. Mp 120° C. (dec). IR (KBr): 3300 (broad s), 2950 (s), 1675 (s), 1300 (s), 1150 (s) cm$^{-1}$. $^1$HNMR (DMSO-d$_6$, 400 MHz): δ0.8 (m, 3H, CH$_2$CH$_3$), 1.0 (d, 3H, CHCH$_3$), 1.25 (m, 10H, (CH$_2$)$_5$), 1.6 (m, 2H, NCH$_2$CH$_2$), 2.45–2.9 (m, 2H, ArCH$_2$), 2.9 (overlapping m, 1H, CHCH$_3$), 2.9 (overlapping s, 3H, SO$_2$CH$_3$), 3.3 (overlapping m, 2H, NCH$_2$CH$_2$), 3.3 (overlapping m, 2H, OHCHCH$_2$NH), 4.7 (m, 1H, OHCH), 6.85 (d, 1H, ArH), 7.05 (m, 1H, ArH), 7.14(m, 2H, ArH), 7.2 (m, 1H. ArH), 7.6 (d, 2H, ArH), six exchangeable resonances were not distinctly observed. MS (ESI) m/z 623 (M$^+$). Analysis Calc for: C$_{28}$H$_{42}$N$_6$O$_6$S$_2$.1H$_2$O: C, 52.48; H, 6.92; N, 13.11; Found: C, 52.71; H, 6.74; N, 12.79.

EXAMPLE 7

4-{[(2S)-3-({2-[4-({4-[({1-[4-(dimethylamino) phenyl]cyclopentyl}methyl)amino]1,1-dioxido-1,25-thiadiazol-3-yl}amino)phenyl]-1 1-dimethylethyl}amino)-2-hydroxypropyl]oxy}phenol Step A To a slurry of 3.7 gm (92.4 mmol) of 60% NaH in 30 mL of DMSO and 5 mL of THF at 35° C, was added 6.17 gm (38.5 mmol) of 4-dimethylaminophenyl acetonitrile and 5.6 mL (46.2 mmol) of 1,4-dibromobutane in 10 mL of THF over a 1 h period. The temperature was allowed to rise to 50° C. and then to 70° C. for 1 h. The reaction mixture was cooled to 0° C. and quenched with 7 mL of water. The reaction mixture was added to 100 mL of water and extracted three times with EtOAc (75 mL). The combined organic layers were washed with water (75 mL), dried ($Na_2SO_4$) and the solvent removed at reduced pressure. The residue was purified by column chromatography on silica gel using 83:17 hexanes-ethyl acetate as an eluent. The oil isolated was crystallized from hexanes to yield 5.92 gm (68%) of the spiro fused compound which was used without further purification or characterization.

Step B

To a slurry of 1.21 gm (30.4 mmol) of lithium aluminum hydride in 20 mL of ether at 0° C. was added a solution of 5.9 gm (27.6 mmol) of the nitrile from Example 6, Step A in 20 mL of ether over a 15 min period. The reaction mixture stirred at 0° C. for 1 h and the mixture was then refluxed for 1 h. The reaction mixture was cooled to 0° C. and quenched with 1.2 mL of water, 1.2 mL of 15% NaOH then 3.6 mL of water. The mixture was diluted with 100 mL of ether, filtered and the solvent removed at reduced pressure to yield 5.79 gm (96%), after recrystallization from EtOAc/hexanes, of a white solid. $^1$HNMR ($CDCl_3$, 300 MHz) δ 1.34 (br s, 2H, N$\underline{H}_2$), 1.68 (m, 4H, $CH_2C\underline{H}_2C\underline{H}_2CH_2$), 1.85 (m, 4H, C$\underline{H}_2CH_2CH_2C\underline{H}_2$), 2.72 (br s, 2H, CC$\underline{H}_2NH_2$), 2.95 (s, 6H, N(C$\underline{H}_3$)$_2$), 6.73 (d, 2H, J=9.0 Hz, Ar$\underline{H}$), 7.18 (d, 2H, J=9.0 Hz, Ar$\underline{H}$).

Step C

To 1.1 gm (2.6 mmol) of the ethoxy substituted thiadiazole-dioxide from Example 4, Step C in 20 mL of ethanol was added 0.57 gm (2.6 mmol) of the amine from Example 6, Step B. The reaction mixture was heated to 70° C. for 18 h. The reaction was cooled to room temperature and half of the solvent was removed at reduced pressure. 3 mL of hexanes was added and the solid was filtered to yield 1.3 gm (84%) of a white solid which was used without further characterization or purification.

Step D

To a solution of 0.6 gm (1.0 mmol) of the Boc-protected amine from Example 6, Step C in 10 mL of $CH_2Cl_2$ was added 1.0 mL (13.1 mmol) of trifluoroacetic acid. The reaction mixture stirred at room temperature for 18h. The solvents were removed at reduced pressure and the residue dissolved in 3 mL of methanol. 4 mL of saturated $NaHCO_3$ was added. The solvents were removed at reduced pressure and 4 mL of $H_2O$ was added and the solid was filtered and used without further purification or characterization.

Step E (2S)-1-(4-Benzyloxy-phenoxy)-3-{2-{4-(4-{[1-(4-dimethylamino-phenyl)-cyclopentylmethyl]-amino}-1,1-dioxo-1H-1(lambda(6))-[1,2,5]thiadiazol-3-ylamino)-phenyl]-1,1-dimethyl-ethylamino}-propan-2-ol To a solution of 0.38 gm (0.76 mmol) of the amine from Example 6, Step D in 5 mL of DMF was added 0.2 gm (0.79 mmol) of (2S)-2-(4-benzyloxy-phenoxymethyl)-oxirane (28). The reaction mixture was allowed to stir at 70° C. for 54 h. The reaction mixture was cooled to room temperature and the solvents removed at reduced pressure. Column chromatography of the residue on silica gel using a gradient of 8–10% methanol-methylene chloride yielded 0.25 gm (44%) of a yellow solid. Mp 116.2–118.8° C. IR (KBr): 3400 (br m), 1640 (m), 1505 (s), 1225 (m) cm$^{-1}$. $^1$HNMR (DMSO-$d_6$, 400 MHz): δ1.12 (br s, 6H, C(C$\underline{H}_3$)$_2$), 1.60–1.94 (m, 8H, C(C$\underline{H}_2$C$\underline{H}_2$C$\underline{H}_2$C$\underline{H}_2$)), 2.82 (br s, 2H, C(CH$_3$)$_2$C$\underline{H}_2$Ar), 2.86 (s, 6H, N(C$\underline{H}_3$)2), 3.4 (br s, 2H, OC$\underline{H}_2$CH(OH)), 3.91 (br s, 2H, CH(OH)C$\underline{H}_2$NH), 4.02 (br s, 1H, CH$_2$C$\underline{H}$(OH)CH$_2$), 5.02 (s, 2H, ArC$\underline{H}_2$O), 6.71 (d, 2H, J=8.57 Hz, Ar$\underline{H}$), 6.87 (d, 2H, J=6.81 Hz, Ar$\underline{H}$), 6.94 (d, 2h, J=6.81 Hz, Ar$\underline{H}$), 7.04–7.15 (m, 2H, Ar$\underline{H}$), 7.17 (d, 2H, J=8.57 Hz, Ar$\underline{H}$), 7.35 (m, 2H, Ar$\underline{H}$), 7.42 (m, 5H, Ar$\underline{H}$), four exchangeable resonances were not distinctly observed. Analysis Calc for: $C_{42}H_{52}N_6O_5S.1.0$ $H_2O$: C, 65.43; H, 7.06; N, 10.90; Found: C, 65.61; H, 6.92; N, 10.68.

Step F

To 0.019 gm of 10% Pd/C in 2 mL of ethanol was added 0.19 gm (0.24 mmol) of the benzyl protected compound from Example 6, Step E. This was allowed to stir at under hydrogen at 1 atm, for 48 h. The reaction was flushed with nitrogen and filtered through celite which was washed with 100 mL of methanol. The solvents were removed under reduced pressure and the residue was chromatographed on silica gel using a gradient of 6–10% methanol-methylene chloride to yield an oil. The oil was added to methylene chloride and 2.5 equivalents of HCl in ether was added. The solvents were removed at reduced pressure to yield 0.12 gm of a tan solid as the dihydrochloride salt. Mp 264.2–266.0° C. (dec). IR (KBr): 3410 (br m), 1649(m), 1508(s), 1158(m) cm$^{-1}$. $^1$HNMR (DMSO-$d_6$, $D_2O$, 400 MHz): δ1.17 (s, 6H, C(C$\underline{H}_3$)$_2$), 1.61–2.09 (m, 8H, C(C$\underline{H}_2$)$_4$), 2.93 (br s, 2H, NHC$\underline{H}_2$C(CH$_2$)$_4$), 3.00 (s, 6H, N(C$\underline{H}_3$)$_2$), 3.01–3.18 (d, 2H, C(CH$_3$)$_2$C$\underline{H}_2$Ar), 3.57 (m, 2H, OC$\underline{H}_2$CH(OH)), 3.88 (m, 2H, CH(OH)C$\underline{H}_2$NH), 4.06 (m, 1H, C$\underline{H}$OH), 6.66 (d, 2H, J=9.00 Hz, Ar$\underline{H}$), 6.76 (d, 2H, J=9.00 Hz, Ar$\underline{H}$), 7.24 (d, 2H, J=8.57 Hz, Ar$\underline{H}$), 7.30 (d, 2H, J=8.78 Hz, Ar$\underline{H}$), 7.37 (d, 2H, J=8.78 Hz, Ar$\underline{H}$), 7.66 (d, 2H, J=8.57 Hz, Ar$\underline{H}$).

EXAMPLE 8

1-Hexyl-3-[4-(1-{[4-(4-{2-[(2S)-2-hydroxy-3-(4-hydroxy-phenoxy)-propylamino]-2-methyl-propyl}-phenylamino)-1,1-dioxo-1H-1.lambda(6).-{1,2,5] thiadiazol-3-ylamino]-methyl}-cyclopentyl)-phenyl]-urea

Step A

In a Parr hydrogenation flask was placed 0.2 gm of 10% palladium on carbon and 50 mL of EtOH. To the reaction mixture was added 2.0 gm (8.76 mmOl) of 2-(4-nitrophenyl)-2-cyclopentylacetonitrile (32) in 50 mL of EtOH. The reaction mixture was hydrogenated at room temperature at 50 psi for 18h. The mixture was filtered through celite and the solvent removed at reduced pressure. Chromatography of the residue on silica gel with 3:1 hexanes-ethyl acetate as the eluent, yielded 1.25 gm (77%) of a light yellow oil which was used without further purification. $^1$HNMR ($CDCl_3$, 300 MHz) δ1.82–2.08 (m, 6H, C$\underline{HH}CH_2CH_2C\underline{HH}$), 2.38–2.49 (m, 2H, CH$\underline{H}$CH$_2$CH$_2$CH$\underline{H}$), 3.6–3.83 (br s, 2H, N$\underline{H}_2$), 6.68 (d, 2H, J=11.5 Hz, Ar$\underline{H}$), 7.21 (d, 2H, J=11.5 Hz, Ar$\underline{H}$).

Step B

To a solution of 1.24 (6.65 mmol) of 2-(4-aminophenyl)-2-cyclopentylacetonitrile Step A, Scheme 8 in 70 mL of toluene was added 7.8 mL (26.6 mmol) of Red-Al over a 10 min period. The solution was allowed to stir at room temperature for 24h. This was carefully quenched with water and the pH raised to 12 with 1 N NaOH. This was extracted 3 times with ethyl acetate and the organic layers were combined, dried ($Na_2SO_4$) and the solvent was removed at reduced pressure to yield a yellow oil. This was used without further purification or characterization.

Step C

To a solution of 1.26 gm (6.65 mmol) of the amine from Step B, Scheme 8, in 70 mL of $CH_2Cl_2$ was added 1.45 gm (6.65 mmol) di-tertbutyl dicarbonate. The reaction mixture was allowed to stir at room temperature for 18h. The solvent was removed at reduced pressure and chromatography of the residue on silica gel with 3:1 hexanes-ethyl acetate as an eluent yielded 1.47 gm (76%) of a white solid. $^1$HNMR ($CDCl_3$, 300 MHz) δ 1.42 (s, 9H, C(C$\underline{H}_3$)$_3$), 1.64–1.95 (m, 8H, C$\underline{H}_2$C$\underline{H}_2$C$\underline{H}_2$C$\underline{H}_2$), 3.13–3.4 (brs, 1H, N$\underline{H}$), 3.22 (d, 2H, J=5.25 Hz, NHC$\underline{H}_2$), 4.05–4.28 (br s, 2H, N$\underline{H}_2$), 6.68 (d, 2H, J=8.25 Hz, Ar$\underline{H}$), 7.08 (d, 2H, J=8.25 Hz).

Step D

To a solution of 0.7 gm (2.4 mmol) of the aniline from Step C, Scheme 8 in 15 mL of $CH_2Cl_2$ was added 0.35 mL (2.4 mmol) of hexyl isocyanate. The solution stirred at room temperature for 72h. The solution was poured into 150 mL of $CH_2Cl_2$ and washed three times with water. The organic layer was dried ($MgSO_4$) and the solvents were removed at reduced pressure. Column chromatography of the residue on silica gel with 3:1 hexanes-ethyl acetate as an eluent yielded a 0.8 gm (76%) of an oil. $^1$HNMR ($CDCl_3$, 300 MHz) δ 0.89 (t, 3H, J=7.4 Hz, $CH_2C\underline{H}_3$), 1.34 (m, 6H, C$\underline{H}_2$C$\underline{H}_2$C$\underline{H}_2$C$\underline{H}_3$), 1.39 (s, 9H, C(C$\underline{H}_3$)$_3$), 1.52–1.62 (m, 2H, NHCH$_2$C$\underline{H}_2$CH$_2$), 1.65–1.98 (m, 10 H, C(C$\underline{H}_2$)$_4$, 3.21 (m, 2H, NHC$\underline{H}_2$), 3.22 (d, 2H, J=5.25 Hz, BocNHC$\underline{H}_2$), 4.27 (br s, 1H, enolizable H), 6.38 (br s, 1H, enolizable H), 7.22 (s, 4H, Ar$\underline{H}$), one exchangeable resonance was not distinctly observed.

Step E

To a solution of 0.81 gm (1.94 mmol) of the protected amine from Step D, Scheme 8 in 7 mL of $CH_2Cl_2$ at room temperature was added 1.94 mL (25.2 mmol) of trifluoroacetic acid. The solution was allowed to stir at room temperature for 18h. The solvents were removed at reduced pressure and the residue dissolved in 4 mL of MeOH. 3 mL of saturated $NaHCO_3$ was added and the solvents were removed at reduced pressure. 3 mL of water was added and the solid was filtered. This was used without further purification or characterization.

Step F

To a solution of the 0.62 gm (1.95 mmol) amine from Step E, Scheme 8 in 8 mL of EtOH was added 0.82 gm (1.95 mmol) of the Boc-protected amine 19 from Scheme 4. The solution was allowed to stir at 70° C. for 24h. The solvents were removed at reduced pressure and 10 mL of a 1:1 ethyl acetate-hexanes was added. An off-white solid (1.02 gm) was filtered and used without further purification or characterization.

Step G

To a solution of 1.02 gm (1.46 mmol) of the solid from Step F, Scheme 8 in 10 mL of $CH_2Cl_2$ was added 1.5 mL (19.0 mmol) of trifluoroacetic acid. The solution was allowed to stir at room temperature for 18h. The solvents were removed at reduced pressure and 30 mL of MeOH was added along with 4 mL of saturated $NaHCO_3$. The solvents were removed at reduced pressure and 4 mL of water was added. An off-white solid (0.86 gm) was filtered and used without further purification or characterization.

Step H

1-[4-(1-{[4-(4-{2-[(2R)-3-(4-Benzyloxy-phenoxy)-2-hydroxy-propylamino]-2-methyl-propyl}-phenylamino)-1 1-dioxo-1H-1.lambda(6).-[1,2,5] thiadiazol-3-ylamino]-methyl}-cyclopentyl)-phenyl]-3-hexyl-urea To a solution of 0.86 gm (1.44 mmol) of the amine from Step G, Scheme 8 in 6 mL of DMF was added 0.37 gm (1.44 mmol) of (2S)-2-(4-benzyloxy-phenoxymethyl)-oxirane (28). The reaction mixture was allowed to stir at 70° C. for 60h. The sovents were removed at reduced pressure. Column chromatography of the residue on silica gel using a 4%–8% MeOH—$CH_2Cl_2$ gradient as an eluent yielded 0.65 gm (53 %) of a light yellow solid. Mp 129–135° C. IR (KBr): 3450 (br s), 1642 (s), 1597 (s), 1502 (s), 1153 (m) cm$^{-1}$. Analysis Calc for: $C_{47}H_{61}N_7O_6S \cdot 1.75 H_2O$: C, 63.88; H, 7.36; N, 11.10; Found: C, 63.76; H, 7.01; N, 10.96.

Step I

To a solution of 0.53 gm (0.62 mmol) of the benzyl protected phenol in Step H, Scheme 8 in 3 mL of MeOH and 3 mL of acetic acid was added 0.53 gm of 10% Pd/C. The flask was flushed with hydrogen and then hydrogenated at room pressure for 72h. The reaction mixture was filtered through celite and the celite was washed with MeOH/$CH_2Cl_2$. The solvents were removed at reduced pressure. The residue was dissolved in MeOH (10 mL) and 4 mL of saturated $NaHCO_3$ was added and the solvents were removed at reduced pressure. The residue was added to 8 mL of water and extracted with 40 mL of $CH_2Cl_2$, 40 mL of $CHCl_3$, then 40 mL of 1:1 MeOH/$CH_2Cl_2$. The solvent was removed at reduced pressure to yield a solid. Mp 154.5–158.5° C. IR (KBr): 3450 (br s), 1643 (m), 1597 (m), 1508 (m), and 1153 (m) cm$^{-1}$. $^1$HNMR (DMSO-$d_6$, $D_2O$, 400 MHz): δ0.81 (t, 3H, J=6.15 Hz, $CH_2C\underline{H}_3$), 1.11 (s, 6H, C(C$\underline{H}_3$)$_2$), 1.21 (br s, 6H, C$\underline{H}_2$C$\underline{H}_2$C$\underline{H}_2$CH$_3$), 1.35 (m, 2H, NCH$_2$C$\underline{H}_2$CH$_2$), 1.58–1.89 (m, 8H, C(C$\underline{H}_2$C$\underline{H}_2$C$\underline{H}_2$C$\underline{H}_2$)), 2.80 (s, 2H, C(CH$_3$)$_2$C$\underline{H}_2$Ar), 2.94 (t, 1H, J=9.2 Hz, NHC$\underline{H}$HC), 3.06 (t, 2H, J=6.5 Hz, NHC$\underline{H}_2$CH$_2$), 3.09 (t, 1H, J=9.2 Hz, NHCH$\underline{H}$C), 3.42 (s, 2H, CH(OH)C$\underline{H}_2$NH), 3.95 (s, 2H, OC$\underline{H}_2$CH(OH)), 4.00 (br s, 1H, C$\underline{H}$OH), 6.65 (d, 2H, J=8.5 Hz, Ar$\underline{H}$), 6.74 (d, 2H, J=8.5 Hz, Ar$\underline{H}$), 7.09 (d, 2H, J=8.13 Hz, Ar$\underline{H}$), 7.18 (d, 2H, J=8.35 Hz, Ar$\underline{H}$), 7.28 (d, 2H, J=8.13 Hz, Ar$\underline{H}$), 7.38 (d, 2H, J=8.35 Hz, Ar$\underline{H}$), seven exchangeable resonances were not distinctly observed. Analysis Calc for: $C_{40}H_{55}N_7O_6S \cdot 1.0 H_2O$: C, 61.59; H, 7.37; N, 12.57; Found: C, 61.87; H, 7.35; N, 12.32.

EXAMPLE 9

(1R)-1-(3-Chloro-phenyl)-2-{2-[3-(4-hexylamino-1,1-dioxo-1H-1-.lambda(6) .-[1,2,5]thiadiazol-3-ylamino)-phenyl]-1-methyl-ethylamino}-ethanol This compound was synthesized in the same manner as in Scheme 2, except that hexyl amine was used instead of octyl amine. Mp 90–96° C. IR (KBr): 3300 (broad m), 2900 (m), 1625 (s), 1300(m), 1150 (s) cm$^{-1}$. $^1$HNMR (CDCl$_3$, 400 MHz): δ 0.9 (m, 3H, $CH_2C\underline{H}_3$). 1.2 (m, 3H, CHC$\underline{H}_3$), 1.3

(overlapping s, 6H, (CH$_2$)$_3$), 1.7 (m, 2H, NCH$_2$CH$_2$), 2.4 (broad s, 1H. CHCH$_3$), 2.6–3.1 (overlapping m, 2H, ArCH$_2$), 2.6–3.1 (overlapping m, 2H, OHCHCH$_2$), 3.4 (s, 2H, NCH$_2$CH$_2$), 5.0 (broad s, 1H, OH), 6.9 (m, 2H, ArH), 7.1–7.3 (overlapping m, 4H, ArH), 7.4 (m, 2H, ArH). Four exchangeable resonances not distinctly observable via $^1$HNMR. HRMS (FAB) Calc. 520.21492 mmu, observed 520.22114 mmu.

EXAMPLE 10

3-(4-{2-[(2R)-2-(3-Chloro-phenyl)-2-hydroxy-ethylamino]-propyl}-phenylamino)-4-octylamino-cyclobut-3-ene-1 2-dione This compound was synthesized in the same manner as in Scheme 1, except that octyl amine was used instead of butyl amine. Mp 173–175° C. IR (KBr): 2900 (m), 1660 (s), 1578 (m), 1460(m) cm$^{-1}$. $^1$HNMR (DMSO-d$_6$, D$_2$O, 400 MHz): δ 0.85 (t, 3H, J=6.59 Hz, CH$_2$CH$_3$), 0.93 (d, 3H, J=6.16 Hz, CHCH$_3$), 1.25 (br m, 10H, CH$_2$(CH$_2$)$_5$CH$_3$), 1.55 (m, 2H, NCH$_2$CH$_2$), 2.45 (m, 1H, CH$_2$NHCH), 2.6–2.9 (m, 4H, NHCH$_2$CH$_2$, ArCH$_2$CH), 3.28 (br m, 1H, CHOH), 3.58 (m, 2H, CH(OH)CH$_2$NH), 4.61 (br m, 1H, CHOH), 5.47 (br s, 1H. NHCHCH$_3$), 7.11 (m, 2H, ArH), 7.26–7.37 (m, 6H, ArH), 7.75 (br s, 1H, CH$_2$CH$_2$NH), 9.69 (br s, 1H, ArNH). HRMS (FAB) Calc. 512.26800 mmu, observed 520.27345 mmu.

EXAMPLE 11

(2S)-1-(4-Benzyloxy-phenoxy)-3-{1-methyl-2-[4-(4-octylamino-1,1-dioxo-1H-1.lambda(6).-[1,2,5]thiadiazol-3-ylamino)-phenyl]-ethylamino}-propan-2-ol This compound was synthesized in the same manner as in Scheme 3, except that (2S)-2-(4-benzyloxy-phenoxymethyl)-oxirane (28) was used instead of (S)-3-chlorophenyl-oxirane. Mp 162–165° C. IR (KBr): 3370 (s), 1651 (m), 1598 (m), 1503 (s), 1120 (m) cm$^{-1}$. $^1$HNMR (DMSO-d$_6$, D$_2$O, 400 MHz): δ 0.82 (t, 3H, J=6.60 Hz, CH$_2$CH$_3$), 1.05 (t, 3H, J=3.6 Hz, CHCH$_3$), 1.22–1.57 (br s, 10H, CH$_2$(CH$_2$)$_5$CH$_3$), 1.56 (m, 2H, NCH$_2$CH$_2$), 2.52 (m, 1H, ArCHHCH), 2.9–3.1 (m, 3H, ArHHCH, NHCH$_2$CH$_2$), 3.27 (t, 2H, J=7.03 Hz, CHOHCH$_2$), 3.55 (m, 1H, NHCHCH$_3$), 3.83 (t, 2H, J=4.83 Hz, OCH$_2$CHOH), 4.05 (br m, 1H, CHOH), 5.00 (s, 2H, ArCH$_2$O), 6.84 (m, 2H, ArH), 6.91 (d, 2H, J=9.2 Hz, ArH), 7.18 (d, 2H, J=7.45 Hz, ArH), 7.29–7.41 (m, 5H, ArH), 7.54 (d, 2H, J=8.35 Hz, ArH). Four exchangeable resonances not distinctly observable via $^1$HNMR. Analysis Calc for: C$_{35}$H$_{47}$N$_5$O$_5$S.1.5 H$_2$O: C, 62.10; H, 7.45; N, 10.35;

Found: C, 61.94; H, 7.34; N, 9.58.

EXAMPLE 12

4-((2S)-2-Hydroxy-3-{1-methyl-2-[4-(4-octylamino-1,1-dioxo-1H-1-.lambda(6).-[1,2,5]thiadiazol-3-ylamino)-phenyl]-1-ethylamino}-propoxy)-phenol This compound was synthesized in the same manner as in Scheme 3, except that (2S)-2-(4-benzyloxy-phenoxymethyl)-oxirane (28) was used instead of (S)-3-chlorophenyl-oxirane and catalytic hydrogenation was used to deprotect the phenol. Mp 203.5–206.0° C. IR (KBr): 3420 (br s), 2920 (s), 1641 (m), 1505 (s), 1148 (m) cm$^{-1}$. $^1$HNMR (DMSO-d$_6$, 400 MHz): δ 0.85 (t, 3H, J=6.6 Hz, CH$_2$CH$_3$), 1.03 (d, 3H, J=6.15 Hz, CHCH$_3$), 1.19–1.32 (br m, 10H, CH$_2$(CH$_2$)$_5$CH$_3$), 1.57 (m, 2H, NCH$_2$CH$_2$), 2.53 (m, 1H, ArCHHCHNH), 2.87–3.06 (m, 3H, ArCHHCHNH, NHC$_2$CH$_2$), 3.22 (br m, 1H, NHCHCH$_3$), 3.30 (m, 2H, CH(OH)CH$_2$NH), 3.83 (t, 2H, J=3.5 Hz, ArOCH$_2$CH), 4.00 (br s,1H, CHOH), 6.72 (d, 2H, J=8.81 Hz, ArH), 6.75 (d, 2H, J=8.81 Hz, ArH), 7.16 (d, 2H, J=7.48 Hz, ArH), 7.54 (d, 2H, J=7.48 Hz, ArH). Five exchangeable resonances not distinctly observable via $^1$HNMR. Analysis Calc for: C$_{28}$H$_{41}$N$_5$O$_5$S 0.5 H$_2$O: C, 59.13; H, 7.44; N, 12.32; Found: C, 59.40; H, 7.35; N, 12.11.

EXAMPLE 13

3-(4-{2-[(2S)-3-(4-Benzyloxy-phenoxy)-2-hydroxy-propylamino]-propyl}-phenylamino)-4-octylamino-cyclobut-3-ene-1,2-dione This compound was synthesized in the same manner as in Scheme 1, except that (2S)-2-(4-benzyloxy-phenoxymethyl)-oxirane (28) was used instead of (S)-3-chlorophenyl-oxirane. $^1$HNMR (DMSO-d$_6$, 400MHz) δ 0.8 (m, 3H, CH$_2$CH$_3$), 0.9 (d, 3H, CHCH$_3$), 1.2 (m, 10H, (CH$_2$)$_5$), 1.5 (m, 2H, NCH$_2$CH$_2$), 2.5 (m, 1H, CHCH$_3$), 2.8 (overlapping m, 2H, CHCH$_2$Ar), 2.8 (overlapping m,2H, CHCH$_2$NH), 3.6 (d, 2H, NHCH$_2$), 3.8 (overlapping m, 3H, OCH$_2$CHOH), 5.0 (s, 2H, ArCH$_2$O), 5.2 (broad s, 1H, NHCH), 6.8 (d, 2H, ArH), 6.9 (d, 2H, ArH), 7.1 (d, 2H, ArH), 7.4. (m, 7H, ArH), 7.9 (s, 1H, NHAr), 9.8 (s, 1H, NHCH$_2$), one exchangeable resonance is not distinctly observed via $^1$HNMR. LC/MS m/z: 614 (M$^+$), 612 (M$^-$).

EXAMPLE 14

3-(4-{2-[(2S)-2-Hydroxy-3-(4-hydroxy-phenoxy)-propylamino]-propyl}-phenylamino)-4-octylamino-cyclobut-3-ene-1,2-dione This compound was synthesized in the same manner as in Scheme 1, except that (2S)-2-(4-benzyloxy-phenoxymethyl)-oxirane (28) was used instead of (S)-3-chlorophenyl-oxirane and octyl amine was used instead of butyl amine. Mp 122–127° C. IR(KBr): 3400 (s), 3290 (s), 2900 (s), 1650 (m), 1575 (m), 1450 (s), 1225 (m) cm$^{-1}$. $^1$HNMR (DMSO-d$_6$, 400 MHz) δ 0.8 (m, 3H, CH$_2$CH$_3$), 1.0 (d, 3H, CHCH$_3$), 1.3 (m, 10H, (CH$_2$)$_5$), 1.5 (m, 2H, NCH$_2$CH$_2$), 2.5 (m, 1H, CHCH$_3$), 2.9 (overlap m, 2H, CHCH$_2$Ar), 2.9 (overlap m, 2H, CHC$_2$NH), 3.6 (d, 2H, NHCH$_2$), 3.8 (m, 2H, OCH$_2$CH), 4.0 (s, 1H, CHOH), 5.2 (broad s, 1H, NHCH), 6.6 (d, 2H, ArH), 6.7 (d, 2H, ArH), 7.2 (d, 2H, ArH), 7.4. (m, 7H, ArH), 8.1 (s, 1H, NHAr), 8.8 (s, 1H, ArOH),10.1 (s, 1H, NHCH$_2$), one exchangeable resonance is not distinctly observed via $^1$HNMR. MS (EI) m/z: 523 (M$^+$).

EXAMPLE 15

3-Decylamino-4-(4-{2-[2-hydroxy-phenoxy)-propylamino]-propyl}phenylamino)-cyclobut-3-ene-1,2-dione This compound was synthesized in the same manner as in Scheme 1, except that (2S)-2-(4-benzyloxy-phenoxymethyl)-oxirane (28) was used instead of (S)-3-chlorophenyl-oxirane, decyl amine was used instead of butyl amine and catalytic hydrogenation was used to debenzylate the phenol. Mp. 130–132° C. IR (KBr): 3250 (br m), 1560 (m), 1425 (s) cm$^{-1}$. $^1$HNMR (DMSO-d$_6$, 400 MHz) δ 0.8 (m, 3H, CH$_2$CH$_3$), 1.0 (d, 3H, CHCH$_3$), 1.2 (overlapping m, 14H, (CH$_2$)$_7$), 1.5 (m, 2H, NCH$_2$CH$_2$), 2.7–3.0 (overlapping m, 2H, ArCH$_2$), 3.1 (broad s, 1H, CHCH$_2$), 3.6 (d, 2H, NCH$_2$), 3.8 (s, 2H, OCH$_2$CH), 3.9 (s, 2H, OCH$_2$CH), 4.8 (broad s,1H, OH), 5.1–5.5 (broad s, 1H, CHOH), 6.7 (d, 2H, OHArH), 6.8 (d, 2H, COArH), 7.2 (d, 2H, ArH), 7.4 (d, 2H,CH$_2$ArH), 8.0 (s, 1H, NHCH$_2$CH$_2$), 9.0 (s, 1H, ArNH), 10.0 (s, 1H, OH), one exchangeable resonance not distinctly observed via $^1$HNMR. LCMS m/z (rel. intensity): 552 (M$^+$), 550 (M$^−$).

Analysis calc. for C$_{32}$H$_{45}$N$_3$O$_5$.1.85 H$_2$O: C, 65.69; H, 8.39; N,7.18

Found: C, 65.48; H, 7.80; N, 7.19.

EXAMPLE 16

3-(4-{2-[(2S)-3-(9H-Carbazol-4-yloxy)-2-hydroxy-propylamino]-propyl}-phenylamino)-4-octylamino-cyclobut-3-ene-1,2-dione This compound was synthesized in the same manner as in Scheme 1, except that carbazole epoxide (27) was used instead of (S)-3-chlorophenyl-oxirane, octyl amine was used instead of butyl amine. Mp 125–131° C. IR (KBr): 3250 (br m), 1560 (s), 1440 (s), cm$^{-1}$. $^1$HNMR (DMSO-d6, 400 MHz): δ 0.8 (m, 3H, CH$_2$CH$_3$), 0.9 (d, 3H, CHCH$_3$), 1.25 (m, 10H, (CH$_2$)$_5$), 1.5 (m, 2H, NCH$_2$), 2.45 (overlapping m, 1H, CH$_3$), 2.8 (m, 2H, CHCH$_2$N), 3.0 (m, 2H, ArCH$_2$), 3.6 (d, 2H, NHCH$_2$), 4.2(overlapping m,1H, OHCH), 5.2 (broad s,1H. CHOH), 6.65 (m, 1H, OArH), 7.05 (m, 2H, CH$_2$ArH), 7.15 (m, 2H, ArH), 7.2–7.4 (overlapping m, 2H, NArH), 7.2–7.4 (overlapping m, 2H, ArH), 7.4 (d, 1H, ArH), 7.76 (s, 1H, ArNH), 8.2 (d, 1H, ArH), 9.7 (S, 1H, NH(CH$_2$)$_8$), 11.6 (s, 1H, ArNHAr), MS (ESI) m/e (rel. intensity): 597 (M+). Analysis Calc'd: C$_{36}$H$_{44}$N$_4$O$_4$ .1.85 H$_2$O: C, 70.33; H, 7.54; N, 9.11. Found: C, 70.46; H, 7.44; N, 9.15.

EXAMPLE 17

3-(4-{[(2S)-3-(9H-Carbazol-4-yloxy)-2-hydroxy-propylamino]-propyl}-phenylamino)-4-decylamino-cyclobut-3-ene-1,2-dione This compound was synthesized in the same manner as in Scheme 1, except that carbazole epoxide (27) was used instead of (S)-3-chlorophenyl-oxirane and decyl amine was used instead of butyl amine. Mp 225° C. IR.(KBr): 3250 (br m), 2900 (m), 1600 (s), 1450 (s) cm$^{-1}$. $^1$HNMR (DMSO-d$_6$, 400 MHz): δ 0.8 (m, 3H, CH$_2$CH$_3$), 0.9 (d, 3H, CHCH$_3$), 1.25 (m, 10H, (CH$_2$)$_7$), 1.5 (m, 2H, NCH$_2$), 2.45 (overlapping m, 1H, CH$_3$), 2.8 (m, 2H, CHCH$_2$N), 3.0 (m, 2H, ArCH$_2$), 3.6 (d, 2H, NHCH$_2$), 4.2 (overlapping m, 1H, OHCH), 5.2 (broad s, 1H, CHOH), 6.65 (m, 1H, OArH), 7.05 (m, 2H, CH$_2$ArH), 7.15 (m, 2H, ArH), 7.2–7.4 (overlapping m, 2H, NArH), 7.2–7.4(overlapping m, 2H, ArH), 7.4 (d, 1H, ArH), 7.76 (s, 1H, ArNH), 8.2 (d, 1H, ArH), 9.7 (s, 1H, NH(CH$_2$)$_8$), 11.6 (s, 1H, ArNHAr), MS (ESI) m/z 625 (M$^+$). Analysis Calc'd: C$_{38}$H$_{50}$N$_4$O$_4$: C, 70.51; H, 7.86; N, 8.65 Found: C, 70.45; H, 7.77; N, 8.80.

EXAMPLE 18

(2S)-1-(4-Benzyloxy-phenoxy)-3-{2-[4-(4-decylamino-1,1-dioxo-1H-1-. lambda(6).-[1,2,5] thiadiazol-3-ylamino)-phenyl]-1-methyl-ethylamino}-propan-2-ol This compound was synthesized in the same manner as in Scheme 3, except that (2S)-2-(4-benzyloxy-phenoxymethyl)-oxirane (28) was used instead of (S)-3-chlorophenyl-oxirane and decyl amine was used instead of octyl amine. Mp 168–172° C. IR (KBr): 3440 (br s), 2915 (m), 1651 (m), 1599 (m), 1507 (s), 1127 (m) cm$^{-1}$. $^1$HNMR (DMSO-d$_6$, 400 MHz): δ 0.85 (t, 3H, J =7.03 Hz, CH$_2$CH$_3$), 1.03 (d, 3H, J=5.72 Hz, CHCH$_3$), 1.57–1.62 (br s, 14H, NCH$_2$CH$_2$(CH$_2$)$_7$CH$_3$), 1.61 (br s, 2H, NCH$_2$CH$_2$), 2.55 (m, 1H, CH(CH$_3$)CHHAr), 2.85 (m, 1H, CH(CH$_3$)CHHAr), 3.02 (m, 2H, NHCH$_2$CH$_2$), 3.24 (br m, 1H, NHCH(CH$_3$)), 3.34 (m, 2H, CHOHCH$_2$N), 3.87 (m, 2H, OCH$_2$CHOH), 4.01 (br s, 1H, CHOH), 5.03 (s, 2H, ArOCH$_2$Ar), 6.87 (d, 2H, J=7.7 Hz, ArH), 6.94 (d, 2H, J=7.7 Hz, ArH), 7.17 (d, 2H, J=7.0 Hz, ArH), 7.30–7.44 (m, 5H, ArH), 7.56 (d, 2H, J=8.12 Hz,ArH), four exchangeable resonance not distinctly observed via $^1$HNMR. Analysis Calc'd: C$_{37}$H$_{51}$N$_5$O$_5$.0.5 H$_2$O: C, 64.69; H, 7.63; N, 10.20.

Found: C, 65.07; H, 7.92; N, 9.82.

EXAMPLE 19

(2S)-1-(9H-Carbozol-4-yloxy)-3-{2-[4-(4-decylamino-1,1-dioxo-1H-1-.lambda(6).-[1,2,5] thiadiazol-3-ylamino)-phenyl]-1-methyl-ethylamino}-propan-2-ol This compound was synthesized in the same manner as in Scheme 3, except that carbazole epoxide (27) was used instead of (S)-3-chlorophenyl-oxirane and decyl amine was used instead of octyl amine. Mp 135–140° C. IR(KBr): 3400 (br m), 2900 (s), 1625(s), 1650(s) 1125(s) cm$^{-1}$. $^1$HNMR (DMSO-d$_6$, 400 MHz):δ 0.9 (m, 3H, CH$_2$CH$_3$), 1.1 (d, 3H, CHCH$_3$), 1.3 (m, 10H, (CH$_2$)$_7$), 1.6 (m, 2H, NCH$_2$CH$_2$), 2.5–3.2 (m, 2H, ArCH$_2$), 3.6 (overlapping m, 2H, NC H$_2$CH$_2$), 3.6 (overlapping m, 2H, OHCHCH$_2$N), 4.2 (overlapping m, 2H, OCH$_2$CH), 4.2 overlapping m, 1H, OH), 6.7 (d, 1H, ArH), 7.1–7.3 (m, 4H, ArH), 7.4 (q, 2H, Ar H), 7.5 (d, 1H, ArH), 7.6 (d, 2H, ArH), 8.3 (d, 1H, ArH), 11.3 (broad s, 1H, NH). Four exchangeable resonances not distinctly observed via $^1$HNMR. MS (ESI) m/e 661 (M+). Analysis calc. for C$_{36}$H$_{48}$N$_6$O$_4$S.1.0 H$_2$O: C, 63.60; H, 7.56; N, 12.36; Found: C, 63.69; H, 7.30; N, 12.28.

EXAMPLE 20

(2S)-1-{2-[4-(4-Decylamino-1,1-dioxo-1H-1(lambda (6))-[1,2,5]thiadiazol-3-ylamino)-phenyl]-1-methyl-ethylamino}-3-phenoxy-propan-2-ol This compound was synthesized in the same manner as in Scheme 3, except that (S)-phenoxymethyloxirane was used instead of (S)-3-chlorophenyl-oxirane and decyl amine was used instead of octyl amine. Mp 153–137° C. IR(KBr): 3350 (s), 2900 (s), 1650 (s), 1600 (s), 1275 (m), 1125 (s) cm$^{-1}$. $^1$HNMR (DMSO-d$_6$, 400 MHz): δ 0.9 (m, 3H, CH$_2$CH$_3$), 1.05 (d, 3H, CHCH$_3$), 1.2 (s, 10H, (CH$_2$)$_7$), 1.55 (s, 2H, NCH$_2$CH$_2$), 2.6 (m, 1H, CHCH$_3$), 2.8–3.3 (overlapping m, 2H, CHCH$_2$Ar), 2.8–3.3 (overlapping m, 2H, CHCH$_2$NH), 2.8–3.3 (overlapping m, 2H, NCH$_2$CH$_2$), 3.9 (m, 2H, ArOCH$_2$), 4.1 (m, 1H, OHCH), 6.9 (m, 3H, ArH), 7.2 (m, 2H, Ar H), 7.3 (m, 2H, ArH), 7.6 (d, 2H, ArH). Four exchangeable resonances not distinctly observed via $^1$HNMR. MS (ESI) m/z 572 (M$^+$). Analysis calc. for C$_{30}$H$_{45}$N$_5$O$_4$S.0.75 H$_2$O: C, 61.56; H, 8.01; N, 11.96; Found: C, 61.41; H, 7.65; N, 11.84.

EXAMPLE 21

(2S)-1-(9H-Carbazol-4-yloxy)-3-{1-methyl-2-[4-(4-octylamino-1,1-dioxo-1H-1(lambda(6))-[1,2,5] thiadiazol-3-ylamino)-phenyl]-ethylamino}-propan-2-ol This compound was synthesized in the same manner as in Scheme 3, except that carbazole epoxide (27) was used instead of (S)-3-chlorophenyl-oxirane. Mp 121–124° C. IR(KBr): 3350 (br m), 2900 (s), 1625(s), 1125(s) cm$^{-1}$. $^1$HNMR (DMSO-d$_6$, 400 MHz): δ 0.9 (m, 3H, CH$_2$CH$_3$), 1.1 (d, 3H, CHCH$_3$), 1.3 (m, 10H, (CH$_2$)$_5$), 1.6 (m, 2H, NCH$_2$CH$_2$), 2.5–3.2 (m, 2H, ArCH$_2$), 3.6 (overlapping m, 2H, NCH$_2$CH$_2$), 3.6 (overlapping m, 2H, OHCHCH$_2$N), 4.2 (overlapping m, 2H, OCH$_2$CH), 4.2 overlapping m, 1H, OH), 6.7 (d, 1H, ArH), 7.1–7.3 (m, 4H, ArH), 7.4 (q, 2H, ArH), 7.5 (d, 1H, ArH), 7.6 (d, 2H, ArH), 8.3 (d, 1H, ArH), 11.3 (broad S, 1H, NH). Four exchangeable resonances not distinctly observed via $^1$HNMR. MS (ESI) m/e 633 (M+). Analysis calc. for C$_{34}$H$_{44}$N$_6$O$_4$S.0.75 H$_2$O: C, 63.18; H, 7.10; N, 13.00; Found: C, 63.19; H, 6.84; N, 13.06.

EXAMPLE 22

This compound was synthesized in the same manner as in Scheme 3, except that (S)-phenoxymethyloxirane was used instead of (S)-3-chlorophenyl-oxirane. Mp 77–82° C. IR(KBr): 3300 (m), 2950 (s), 1625 (s), 1600 (s), 1500 (m), 1250 (m), 1125 (s) cm$^{-1}$. $^1$HNMR (DMSO-d$_6$, 400 MHz): δ 0.9 (m, 3H, CH$_2$CH$_3$), 1.05 (d, 3H, CHCH$_3$), 1.2 (s, 10H, (CH$_2$)$_5$), 1.55 (s, 2H, NCH$_2$CH$_2$), 2.6 (m, 1H, CHCH$_3$), 2.8–3.3 (overlapping m, 2H, CHCH$_2$Ar), 2.8–3.3 (overlapping m, 2H, CHCH$_2$NH), 2.8–3.3 (overlapping m, 2H, NCH$_2$CH$_2$), 3.9 (m, 2H, ArOCH$_2$), 4.1 (m, 1H, OHCH), 6.9 (m, 3H, ArH), 7.2 (m, 2H, ArH), 7.3 (m, 2H, ArH), 7.6 (d, 2H, ArH). Four exchangeable resonances not distinctly observed via $^1$HNMR. MS (ESI) m/z 544 (M$^+$). Analysis calc. for C$_{28}$H$_{41}$N$_5$O$_4$S.1.0 H$_2$O: C, 59.87; H, 7.72; N, 12.47; Found: C, 60.09; H, 7.44; N, 12.50.

EXAMPLE 23

3-Decylamino-4-{4-[4-[2[((2S)-2-hydroxy-3-phenoxy-propylamino)-propyl]-phenylamino)-cyclobut-3-ene-1,2-dione This compound was synthesized in the same manner as in Scheme 1, except that (S)-phenoxymethyloxirane was used instead of (S)-3-chlorophenyl-oxirane and decyl amine was used instead of butyl amine. Mp 144–155° C. IR (KBr): 3450 (m), 3200 (m), 2900 (m),1650 (s), 1450 (s), 1250 (m),750 (m) cm$^{-1}$. $^1$HNMR (DMSO-d6, 400MHz) δ 0.8 (m, 3H, CH$_2$CH$_3$), 0.9 (d, 3H, CHCH$_3$), 1.2 (m, 10H, (CH$_2$)$_7$), 1.6 (m, 2H, NCH$_2$CH$_2$), 2.5 (m, 1H. CHCH$_3$), 2.6–2.9 (overlapping m, 2H, CHCH$_2$Ar), 2.6–2.9 (overlapping m, 2H, CHCH$_2$NH), 3.6 (d, 2H, NHCH$_2$), 3.9 (overlapping m, 3H, OCH$_2$CHOH), 5.1 (broad s, 1H, NHCH), 6.9 (m, 3H, ArH), 7.15 (d, 2H, ArH), 7.3 (t, 2H, ArH), 7.4 (d, 2H, ArH), 7.8 (broad s, 1H, NHAr), 9.8 (s, 1H, NHCH$_2$), one exchangeable resonance is not distinctly observed via $^1$HNMR. MS (ESI) m/z: 536 (M$^+$).

Analysis calc. for C$_{32}$H$_{45}$N$_3$O$_4$.1.25 H$_2$O: C, 68.85; H, 8.57; N, 7.52; Found: C, 68.71; H, 8.31; N, 7.57.

EXAMPLE 24

3-{4-[2-((2S)-2-Hydroxy-3-phenoxy-propylamino)-propyl]-phenylamino}-4-octylamino-cyclobut-3-ene-1,2-dione This compound was synthesized in the same manner as in Scheme 1, except that (S)-phenoxymethyloxirane was used instead of (S)-3-chlorophenyl-oxirane and octyl amine was used instead of butyl amine. Mp 146–155° C. IR (KBr): 3400 (m), 2900 (m), 1625 (s), 1450 (s), 1225 (m),750 (m) cm$^{-1}$. $^1$HNMR (DMSO-d6, 400MHz) δ 0.8 (m, 3H, CH$_2$CH$_3$), 0.9 (d, 3H, CHCH$_3$), 1.2 (m, 10H, (CH$_2$)$_5$), 1.6 (m, 2H, NCH$_2$CH$_2$), 2.5 (m, 1H, CHCH$_3$),2.6–2.9 (overlapping m, 2H, CHCH$_2$Ar), 2.6–2.9 (overlapping m, 2H, CHCH$_2$NH), 3.6 (d, 2H, NHCH$_2$), 3.9 (overlapping m, 3H, OCH$_2$CHOH), 5.1 (br s, 1H, NHCH), 6.9 (m, 3H, ArH), 7.15 (d, 2H, ArH), 7.3 (t, 2H, ArH), 7.4 (d, 2H, ArH), 7.8 (br s, 1H. NHAr), 9.8 (s, 1H. NHCH$_2$), one exchangeable resonance is not distinctly observed via $^1$HNMR. MS (ESI) m/z: 508 (M$^+$). Analysis calc. for C$_{30}$H$_{41}$N$_3$O$_4$.0.75 H$_2$O: C, 69.13; H, 8.22; N, 8.06; Found: C, 69.07; H, 7.94; N, 8.35.

EXAMPLE 25

4-((2S)-3-{2-[4-(4-Decylamino-1,1-dioxo-1H-1 (lambda(6))-[1,2,5]thiadiazol-3-ylamino)-phenyl]-1-methyl-ethylamino}-2-hydroxy-propoxy)-phenol This compound was synthesized in the same manner as in Scheme 3, except that (2S)-2-(4-benzyloxy-phenoxymethyl)-oxirane (28) was used instead of (S)-3-chlorophenyl-oxirane, decyl amine was used instead of octyl amine and catalytic hydrogenation was used to deprotect the phenol. Isolated as HCl salt. Mp 146–155° C. IR (KBr): 3380 (br s), 2920 (m), 1698 (m), 1602 (m), 1510 (m), 1120 (m). $^1$HNMR (DMSO-d6, 400MHz) δ 0.85 (t, 3H, J=7.03 Hz, CH$_2$CH$_3$), 1.12 (m, 3H, CHCH$_3$), 1.2–1.38 (br m, 14H, CH$_2$(CH$_2$)$_7$CH$_3$), 1.65 (m, 2H, NCH$_2$CH$_2$), 2.67 (q, 1H, J=10.3 Hz, NHCHCH$_3$), 3.06 (br s, 1H, ArCHHCHCH$_3$), 3.24 (m, 2H, NHCH$_2$CH$_2$), 3.38 (m, 2H, CHOHCH$_2$NH), 3.49 (br s, 1H, ArCHHCHCH$_3$), 3.88 (m, 2H, OCH$_2$CHOH), 4.16 (m, 1H. CHOH), 5,86 (d,1H, J=4.8 Hz, NH), 6.68 (d, 2H, J=9.0 Hz, ArH), 6.79 (d, 2H, J=9.0 Hz, ArH), 7.33 (dd, 2H, J=3.3, 8.6 Hz, ArH), 7.87 (d, 2H, J=7.7 Hz, ArH), 8.64 (br s, 2H, NHHCl), 8.97 (s, 1H, ArOH), 10.04 (br s, 1H, CH$_2$NH), 11.53 (br s, 1H, ArNH). Analysis calc. for C$_{30}$H$_{45}$N$_5$O$_5$S.1.0 HCl.0.5 H$_2$O: C, 56.90; H, 7.48; N, 11.06; Found: C, 57.07; H, 7.30; N, 10.96.

EXAMPLE 26

N-[2-Benzyloxy-5-((1R)-2-{2-[4-(4-decylamino- 11 -dioxo-1H-1(lambda(6))-[1,2,5]thiadiazol-3-ylamino)-phenyl]-1-methyl-ethylamino}-1-hydroxy-ethyl)-phenyl]-methanesulfonamide This compound was synthesized in the same manner as in Scheme 6, except that decyl amine was used instead of octyl amine and the debenzylation step was not performed. Mp 92–97° C. IR (KBr): 3350 (br m), 2950 (s), 1625 (s), 1310 (m), 1150 (s) cm$^{-1}$. $^1$HNMR (DMSO-d$_6$, 400 MHz): δ 0.8 (m, 3H, CH$_2$CH$_3$), 1.0 (d, 3H, CHCH$_3$), 1.3 (m, 14H, (CH$_2$)$_7$), 1.6 (m, 2H, NCH$_2$CH$_2$), 2.5–2.9 (overlapping m, 2H, ArCH$_2$), 2.9 (s, 3H, SO$_2$CH$_3$), 3.0 (s, 1H, CHCH$_3$), 3.3 (overlapping m, 2H, NCH$_2$CH$_2$), 3.3 (overlapping m, 2H, OCHCH$_2$N), 4.7 (m, 1H, OCH), 5.2 (s, 2H, OCH$_2$), 7.1–7.2 (m, 4H, ArH), 7.3 (m, 2H, ArH), 7.4 (m, 2H, ArH), 7.5 (d, 2H, ArH), 7.6 (s, 2H, ArH). Five exchangeable resonances not distinctly observed via $^1$HNMR. MS (ESI) 739 (M$^-$).

Analysis calc. for C$_{37}$H$_{52}$N$_6$O$_6$S$_2$.0.5 H$_2$O: C, 58.55; H, 7.17; N, 11.07. Found: C, 58.17; H, 7.08; N, 10.89.

EXAMPLE 27

N-[5-((1R)-2-{2-[4-(4-Decylamino-1,1-dioxo-1H-1(lambda(6))-[1 2,5]thiadiazol-3-ylamino)-phenyl]-1-methyl-ethylamino}-1-hydroxy-ethyl)-2-hydroxy-phenyl]-methanesulfonamide This compound was synthesized in the same manner as in Scheme 6, except that decyl amine was used instead of octyl amine. Mp 120° C. (dec). IR (KBr): 3300 (br m), 2900 (m), 1625 (m), 1300 (m), 1150 (s) cm$^{-1}$. $^1$HNMR (DMSO-d$_6$, 400 MHz): δ 0.9 (m, 3H, CH$_2$CH$_3$), 1.1 (m, 3H, CHCH$_3$), 1.3 (m, 14H, (CH$_2$)$_7$), 1.6 (m, 2H, NCH$_2$CH$_2$), 2.5–2.9 (overlapping m, 2H, ArCH$_2$), 2.9 (s, 3H, SO$_2$CH$_3$), 3.0 (s, 1H, CHCH$_3$), 3.3 (overlapping m, 2H, NCH$_2$CH$_2$), 3.3 (overlapping m, 2H, OCHCH$_2$N), 4.7 (m, 1H, OCH), 6.9 (d, 1H, ArH), 7.1 (d, 1H, ArH), 7.2 (overlapping m, 2H, ArH), 7.3 (overlapping m, 2H, ArH), 7.7 (m, 3H, ArH). Four exchangeable resonances not distinctly observed via $^1$HNMR. MS (ESI) 651 (M$^+$). Analysis calc. for C$_{30}$H$_{46}$N$_6$O$_6$S$_2$·1.0 H$_2$O: C, 53.87; H, 7.23; N, 12.56. Found: C, 53.84; H, 7.05; N, 12.16.

EXAMPLE 28

2S)-1-(4-Benzyloxy-phenoxy)-3-(2-{4-[4-(2,2-diphenyl-ethylamino)-1,1-dioxo-1H-1(lambda(6))-[1,2,5]thiadiazol-3-ylamino]-phenyl}-1,1-dimethyl-ethylamino)-propan-2-ol This compound was synthesized in the same manner as in Scheme 4, except that 2,2-diphenethyl amine was used instead of octyl amine. Mp 222.5–224.5° C. (dec). IR (KBr): 3420 (m), 1647 (m), 1599 (m), 1505 (s), 1122 (m). $^1$HNMR (DMSO-d$_6$, DCl, D$_2$O, 400 MHz): δ 1.17 (s, 6H, C(CH$_3$)2), 2.98 (m, 1H, ArCHH), 2.99 (m, 2H, NHCH$_2$CHArAr), 3.18 (m, 1H, ArCHH), 3.91 (d, 2H, J=5.27 Hz, CHOHCH$_2$NH), 4.01 (d, 2H, J=9.9 Hz, OCH$_2$CHOH), 4.18 (m,1H. CHOH), 4.56 (t, 2H, J=7.9 Hz, CHArAr), 4.99 (s, 2H, ArCH$_2$O), 6.87 (m, 4H, ArH), 6.89 (m, 2H, ArH), 7.22–7.39 (m, 15H, ArH), 7.83 (D, 2H, J=8.8 Hz, ArH). Analysis calc. for C$_{42}$H$_{45}$N$_5$O$_5$S: C, 68.92; H, 6.20; N, 9.57. Found: C, 68.59; H, 6.17; N, 9.48.

EXAMPLE 29

4-[(2S)-3-(2-{4-[4-(2,2-Diphenyl-ethylamino)-1,1-dioxo-1H-1(lambda(6))-[1,2,5]thiadiazol-3-ylamino]-phenyl}-1,1-dimethyl-ethylamino)-2-hydroxy-propoxy]l-phenol This compound was synthesized in the same manner as in Scheme 4, except that 2,2-diphenethyl amine was used instead of octyl amine. Mp 241–243° C. (dec). IR (KBr): 3380 (s), 1643 (m), 1608 (m), 1507 (s), 1139 (s). $^1$HNMR (DMSO-d$_6$, 400 MHz): δ 1.11 br s, 6H, C(CH$_3$)$_2$), 2.78 (br s, 2H, NHCH$_2$CH), 2.95 (br m, 1H, C(CH$_3$)$_2$CHHAr), 3.29 (br s, 1H, C(CH$_3$)$_2$CHHAr), 3.32 (br s, 2H, CHOHCH$_2$NH), 3.87 (d, 2H, J=5.05 Hz, OCH$_2$CHOH), 4.02 (br s, 1H, CHOH), 4.50 (t, 1H, J=7.46 Hz, CHArAr), 6.67 (m, 2H, ArH), 6.76 (dd, 2H, J=2.20, 6.71 Hz, ArH), 7.08 (br s, 2H, ArH), 7.19 (m, 2H, ArH), 7.28–7.40 (m, 8H, ArH), 7.44 (br s, 2H, ArH). Five exchangeable resonances not distinctly observed via $^1$HNMR. Analysis calc. for C$_{34}$H$_{37}$N$_5$O$_5$S: C, 65.05; H, 5.94; N, 11.16. Found: C, 65.12; H, 6.11; N, 10.74.

EXAMPLE 30

(2S)-1-(4-Benzyloxy-phenoxy)-3-[2-(4-{1,-dioxo-4-[(1-phenyl-cyclopentylmethyl)-amino]-1H-1(lambda(6))-[1,2,5]thiadiazol-3-ylamino}-phenyl)-1-methyl-ethylamino]-propan-2-ol This compound was synthesized in the same manner as in Scheme 3, except that (2S)-2-(4-benzyloxy-phenoxymethyl)-oxirane (28) was used instead of (S)-3-chlorophenyl-oxirane, 1-aminomethyl-1-phenyl cyclopentane was used instead of octyl amine. Mp 103–105° C. IR (KBr): 3440 (br s), 2940 (m), 1641 (m), 1600 (m), 1503 (s), 1130 (m). $^1$HNMR (DMSO-d$_6$, D$_2$O, 400 MHz): δ 1.04 (m, 3H, CHCH$_3$), 1.59 (br m, 2H, C(CH$_2$CH$_2$CH$_2$CH$_2$)), 1.72 (br m, 2H, C(CH$_2$CH$_2$CH$_2$CH$_2$)), 1.82 (br m, 2H, C(CH$_2$CH$_2$CH$_2$CH$_2$)), 1.95 (br m, 2H, C(CH$_2$CH$_2$CH$_2$CH$_2$)), 2.55 (m, 1H, ArCHHCCH$_3$), 2.88 (br m, 1H, NHCHHC(CH$_2$)$_4$), 2.96 (m, 1H, NHCHCH$_3$), 3.05 (m, 1H, ArCHHCCH$_3$), 3.28 (br m, 1H, NHCHHC(CH$_2$)$_4$), 3.45 (br s, 2H, CHOHCH$_2$NH), 3.81 (m, OCH$_2$CHOH), 4.01 (m, 1H, CHOH), 4.97 (s, 2H, ArCH$_2$OAr), 6.84 (m, 2H, ArH), 6.88 (m, 2H, ArH), 7.10 (d, 2H, J=8.82 Hz, ArH), 7.20 (m, 1H, ArH), 7.25–7.39 (m, 11H, ArH). Four exchangeable resonances not distinctly observed via $^1$HNMR. Analysis calc. for C$_{39}$H$_{45}$N$_5$O$_5$S·1.0 H$_2$O: C, 65.61; H, 6.64; N, 9.81. Found: C, 65.39; H, 6.44; N, 9.45.

EXAMPLE 31

4-{(2S)-3-[2-(4-{1,1-Dioxo-4-[(1-phenyl-cyclopentylmethyl)-amino]-1H-1(lambda(6))-[1,2,5]thiadiazol-3-ylamino}-phenyl)-1-methyl-ethylamino]-2-hydroxy-propoxy}-phenol This compound was synthesized in the same manner as in Scheme 3, except that (2S)-2-(4-benzyloxy-phenoxymethyl)-oxirane (28) was used instead of (S)-3-chlorophenyl-oxirane, 1-aminomethyl-1-phenyl cyclopentane was used instead of octyl amine. Isolated as HCl salt. Mp 162–165° C. IR (KBr): 3460 (br s), 2935 (m), 1643 (m), 1599 (m), 1505 (s), 1123 (s). $^1$HNMR (DMSO-d$_6$, 400 MHz): δ 1.13 (m, 3H, CHCH$_3$), 1.59 (br m, 2H, C(CH$_2$CH$_2$CH$_2$)), 1.75 (m, 2H, C(CH$_2$CH$_2$CH$_2$CH$_2$)), 1.90 (m, 2H, C(CH$_2$CH$_2$CH$_2$CH$_2$)), 2.14 (m, 2H, C(CH$_2$CH$_2$CH$_2$CH$_2$)), 2.65 (q, 1H, J=10.76 Hz, NHCHCH$_3$), 3.05 (m, 1H, ArCHHCHCH$_3$), 3.22 (br m, 1H, NHCH$_2$C(CH$_2$)$_4$)), 3.46 (br m,1H, ArCHHCHCH$_3$), 3.62 (d, 2H, J=5.72 Hz, CHOHCH$_2$NH), 3.87 (m, 2H, OCH$_2$CHOH), 4.14 (br s,1H. CHOH), 5.84 (d,1H, J=4.91 Hz, CHOH), 6.68 (d, 2H, J=6.8 Hz, ArH), 6.77 (d, 2H, J=6.8 Hz, ArH), 7.16 (m, 1H, ArH), 7.17–7.24 (m, 3H, ArH), 7.37 (d, 2H, J=7.25 Hz, ArH), 7.80 (d, 2H, J=7.25 Hz, ArH), 8.62 (br m, 1H, NHHCl), 8.75 (br m, 1H, NHHCl), 8.96 (s, 1H, ArOH), 9.50 (br s, 1H, CH$_2$NHhet), 11.64 (br s, 1H, ArNHhet). Analysis calc. for C$_{32}$H$_{39}$N$_5$O$_5$S·1.0 HCl·1.50 H$_2$O: C, 57.43; H, 6.48; N, 10.47. Found: C, 57.67; H, 6.30; N, 9.86.

EXAMPLE 32

4-[4-(4-{2-[(2S)-3-(4-benzyloxy-phenoxy)-2-hydroxy-propylamino]-propyl}-phenylamino)-1,1-Dioxo-1H-1(lambda(6))-[1,2,5]thiadiazol-3-ylamino]-butyric acid ethyl ester This compound was synthesized in the same manner as in Scheme 3, except that (2S)-2-(4-benzyloxy-phenoxymethyl)-oxirane (28) was used instead of (S)-3-chlorophenyl-oxirane and 4-aminobutyric acid ethyl ester was used instead of octyl amine. Mp 100.3–102.5° C. IR (KBr): 3340 (m), 1647 (m), 1598 (m), 1503 (m), 1153 (m). $^1$HNMR (DMSO-d$_6$, D$_2$O, 400 MHz): δ 1.07 (t, 3H, J=5.5 Hz, CHCH$_3$), 1.12 (t, 3H, J=7.25 Hz, OCH$_2$CH$_3$) 1.81 (m, 2H, NCH$_2$CH$_2$), 2.33 (t, 2H, J=7.51 Hz, CH$_2$CH$_2$C(O)), 2.62 (m, 1H, CCH$_3$CHHAr), 2.91–3.11 (m, 3H, CHCH$_3$, NHCH$_2$CH$_2$), 3.31 (m, 3H, CCH$_3$CHHAr, CHOHCH$_2$NH), 3.84 )t, 2H, J=4.41 Hz, OCH$_2$CHOH), 3.97–4.05 (m, 3H, CHOH, OCH$_2$CH$_3$), 4.97 (s, 2H, ArCH$_2$O), 6.82 (m, 2H, ArH), 6.86 (m, 2H, ArH), 7.19 (d, 2H, J=7.47 Hz, ArH), 4.32 (M,1H. ArH), 7.35 (m, 4H, ArH), 7.50 (d, 2H, J=7.91 Hz, ArH). Four exchangeable resonances not distinctly observed via $^1$HNMR.

EXAMPLE 33

4-{4-(4-{2-[(2S)-2-Hydroxy-3-(4-hydroxy-phenoxy)-propylamino]-propyl}-phenylamino)-1,1-dioxo-1H-1.lambda(6).-[1,2,5]thiadiazol-3-ylamino]-butyric acid ethyl ester This compound was synthesized in the same manner as in Scheme 3, except that (2S)-2-(4-benzyloxyphenoxymethyl)-oxirane (28) was used instead of (S)-3-chlorophenyl-oxirane, 4-aminobutyric acid ethyl ester was used instead of octyl amine and catalytic hydrogenation was used to deprotect the phenol. Mp 135–139° C. IR (KBr): 3250 (br m), 1647 (m), 1596 (m), 1505 (m), 1159 (m). $^1$HNMR (DMSO-d$_6$, D$_2$O, 400 MHz): δ 1.05 (m, 3H, CHCH$_3$), 1.13 (t, 3H, J=7.25 Hz, OCH$_2$CH$_3$), 1.83 (m, 2H, NHCH$_2$CH$_2$CH$_2$), 2.33 (t, 2H, J=7.47 Hz, CH$_2$CH$_2$C(O)), 2.58 (m, 1H, CHCH$_3$CHHAr), 2.87–3.10 (m, 3H, CHCH$_3$, NHCH$_2$CH$_2$), 3.22–3.31 (m, 3H, CHCH$_3$CHHAr, CHOHCH$_2$NH), 3.82 (m, 2H, OCH$_2$CHOH), 4.02 (m, 3H, OCH$_2$CH$_3$, CHOH), 6.65 (d, 2H, J=8.79 Hz, ArH), 6.74 (d, 2H, J=8.79 Hz, ArH), 7.15 (d, 2H, J=8.13 Hz, ArH), 7.48 (d, 2H, J=8.13 Hz, ArH). Five exchangeable resonances not distinctly observed via $^1$HNMR.

EXAMPLE 34

N-[5-(2-{2-[4-(4-{[1-(4-dimethylamino-phenyl)-cyclopentylmethyl]-amino}-1,1-dioxo-1H-1.lambda(6).-[1,2,5]thiadiazol-3-ylamino)-phenyl]-1,1-dimethyl-ethylamino}-1-hydroxy-ethyl)-2-hydroxy-phenyl]-methanesulfonamide This compound was synthesized in the same manner as in Scheme 6, except that Boc-protected amine 20, where R$^3$ was 1-aminomethyl-1-(4'-dimethylamino)phenyl cyclopentane, was utilized instead of octylamine. Mp 192–195° C. IR (KBr): 3420 (br m), 1648 (m), 1598 (m), 1516 (m), 1155 (m). $^1$HNMR (DMSO-d$_6$, D$_2$O, 400 MHz): δ 1.11 (s, 6H, C(CH$_3$)$_2$), 1.58 (m, 2H, ArC(CH$_2$CH$_2$CH$_2$)), 1.71 ((m, 2H, ArC(CH$_2$CH$_2$CH$_2$CH$_2$)), 1.81 (m, 2H, ArC(CH$_2$CH$_2$CH$_2$CH$_2$)), 1.86 (m, 2H, ArC(CH$_2$CH$_2$CH$_2$CH$_2$)), 2.81 (br s, 2H, hetNHCH$_2$), 2.83 (s, 6H, N(CH$_3$)$_2$), 2.90–3.03 (m, 2H, ArCH$_2$C(CH$_3$)$_2$), 2.92 (s, 3H, NHSO$_2$CH$_3$), 3.41 (br s, 2H, CHOHCH$_2$N), 4.66 (m, 1H, CHOH), 6.69 (d, 2H, J=8.57 Hz, ArH), 6.88 (d, 1H, J=8.45 Hz, ArH), 7.08 (d, 3H, J=8.35 Hz, ArH), 7.16 (d, 2H, J=8.57 Hz, ArH), 7.24 (s, 1H, ArH), 7.41 (d, 2H, J=8.18 Hz, ArH).). Six exchangeable resonances not distinctly observed via $^1$HNMR.

EXAMPLE 35

(2S)-1-(1,3-Benzodioxol-5-yloxy)-3-{1-methyl-2-[4-(4-octylamino-1,1-dioxo-1H-1.lambda(6).-[1,2,5]thiadiazol-3-ylamino)-phenyl]-ethylamino}-propan-2-ol This compound was synthesized in the same manner as in Scheme 3, except that 1-(3,4-methylenedioxyphenoxy)-2,3-(S)-epoxypropane was used instead of (S)-3-chlorophenyl-oxirane, 1-aminomethyl-1-phenyl cyclopentane was used instead of octyl amine. Mp 81–86° C. IR (KBr): 3300 (broad m), 2900 (s), 1625 (s), 1500 (s), 1300 (m), 1150 (s) cm$^{-1}$. $^1$HNMR (DMSO-d$_6$, 400 MHz): δ 0.8 (m, 3H, CH$_2$CH$_3$), 1.05 (d, 3H, CHCH$_3$), 1.3 (m, 10H, (CH$_2$)$_5$), 1.6 (m, 2H, NCH$_2$CH$_2$), 2.5–2.9 (overlapping m, 2H, ArCH$_2$), 2.9 (overlapping m, 1H, CHCH$_3$), 3.2 (overlapping m, 2H, NCH$_2$CH$_2$), 3.3 (overlapping m, 2H, OHCHCH$_2$), 3.8 (m, 2H, ArOCH$_2$), 4.0 (s, 1H, OHCH), 5.95 (s, 2H, OCH$_2$O), 6.4 (d, 1H, ArH), 6.6 (m, 1H, ArH), 7.2 (d, 2H, ArH), 7.5 (d, 2H, ArH). Four exchangeable resonances not distinctly observable via $^1$HNMR. MS (APCl) m/z 588 (M$^+$) Analysis Calc. for C$_{29}$H$_{41}$N$_5$O$_6$S.1.0 H$_2$O: C, 57.50; H, 7.16; N, 11.56. Found: C, 57.82; H, 6.85; N, 11.93.

EXAMPLE 36

(S)-4-{2-hydroxy-3-[2-(4-{4-[2-(4methoxy-phenyl)-ethylamino]-1 1-dioxo-1H-1.lambda(6).-[1,2,5]thiadiazol-3-ylamino}-phenyl)-1-methyl-ethylamino]-propoxy}-phenol This compound was synthesized in the same manner as in Scheme 3, except that (2S)-2-(4-benzyloxy-phenoxymethyl)-oxirane (28) was used instead of (S)-3-chlorophenyl-oxirane, 4-methoxypenethyl amine was utilized instead of octyl amine and catalytic hydrogenation was used to deprotect the phenol. Mp 95–100° C. IR(KBr): 3300 (broad m), 1625 (m), 1525 (s), 1250 (m), 1150 (m) cm$^{-1}$. $^1$HNMR (DMSO-d$_6$, 400 MHz): δ 1.5 (d, 3H, CHCH$_3$), 2.4–2.9 (overlapping m, 2H, CHCH$_2$Ar),2.85 (t, 2H, NCH$_2$CH$_2$), 3.1 (overlapping m, 1H, CHCH$_3$), 3.3 (overlapping m, 2H, OCHCH$_2$N), 3.5 (m, 2H, NCH$_2$CH$_2$), 3.7 (s, 3H, OCH$_3$), 3.85 (d, 2H, OCH$_2$), 4.05 (m, 1H, OCH), 6.7 (t, 2H, ArH), 6.75 (t, 2H, ArH), 6.85 (t, 2H, ArH), 7.2 (d, 4H, ArH), 7.6 (m, 2H, ArH). Five exchangeable resonances aren't distinctly observable via $^1$HNMR. MS (APCl) m/z 582 (M$^+$).

Analysis calc. for C$_{29}$H$_3$N$_5$O$_6$S.1.50 H$_2$O: C, 57.22; H, 6.29; N, 11.51, Found: C, 57.17; H, 6.04; N, 10.96.

EXAMPLE 37

4-{(2S)-3-[2-(4-{4-[2-(4-Fluoro-phenyl)-ethylamino]-1 1-dioxo-1H-1.lambda(6).-[1,2,5]thiadiazol-3-ylamino}-phenyl-1-methyl-ethylamino]-2-hydroxy-propoxy}-phenol This compound was synthesized in the same manner as in Scheme 3, except that (2S)-2-(4-benzyloxy-phenoxymethyl)-oxirane (28) was used instead of (S)-3-chlorophenyl-oxirane, 4-fluorophenethyl amine was utilized instead of octyl amine and catalytic hydrogenation was used to deprotect the phenol. Mp 126–131° C. IR (KBr): 3000 (broad w), 1650 (m), 1600 (m), 1525 (s), 1250 (m), 1150 (m) cm$^{-1}$. $^1$HNMR (DMSO-d6, 400 MHz): d 1.0 (d, 3H, CHCH$_3$), 2.4–3.0 (overlapping m, 2H, CHCH$_2$Ar), 2.8 (m, 2H, NCH$_2$CH$_2$), 3.1 (m, 1H, CHCH$_3$), 3.3 (overlapping m, 2H, OCHCH$_2$N), 3.45 (m, 2H, NCH$_2$CH$_2$), 3.8 (m, 2H, OCH$_2$), 3.9 (s, 1H, OCH), 6.65 (d, 2H, ArH), 6.7 (d, 2H, ArH), 7.1 (m, 4H, ArH), 7.3 (m, 2H, ArH), 7.5 (d, 2H, ArH). MS (APCl) m/z 570 (M$^+$).

What is claimed is:

1. A compound of formula I having the structure

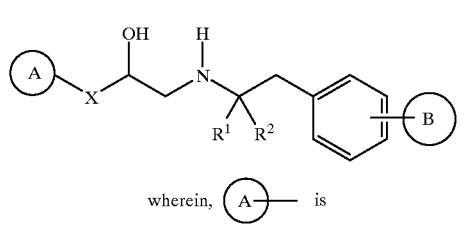

wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

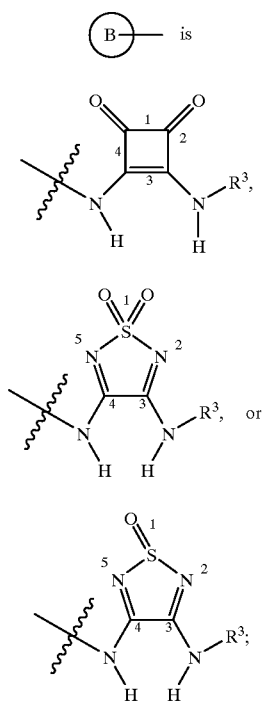

X is —OCH$_2$— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;
R$^1$ and R$^2$ are each, independently, hydrogen, alkyl of 1–6 carbon atoms, or cycloalkyl of 3–8 carbon atoms;
R$^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;

(b) cycloalkyl of 3–8 carbon atoms;

(c) arylalkyl wherein the alkyl moiety contains 1–10 carbon atoms;

(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;
Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;
m=0–2;
n=1–2;

or a pharmaceutically acceptable salt thereof.

2. The compound according to claim 1, wherein

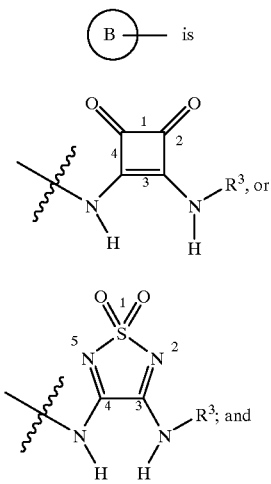

or a pharmaceutically acceptable salt thereof.

3. The compound according to claim 1, wherein

R$^3$ is alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;

or a pharmaceutically acceptable salt thereof.

4. The compound of claim 1, which is
a) 3-Butylamino-4-(4-{2-[(2R)-2-(3-chloro-phenyl)-2-hydroxy-ethylamino]-propyl}-phenylamino)-cyclobut-3-ene-1,2-dione;
b) 3-(4-{2-[(2R)-2-(3-chloro-phenyl)-2-hydroxy-ethylamino]-propyl}-phenylamino)-4-octylamino-cyclobut-3-ene-1,2-dione;
c) 3-(4-{2-[(2S)-3-(4-Benzyloxy-phenoxy)-2-hydroxy-propylamino]-propyl}-phenylamino)-4-octylamino-cyclobut-3-ene-1,2-dione;
d) 3-(4-{2-[(2S)-2-hydroxy-3-(4-hydroxy-phenoxy)-propylamino]-propyl}-phenylamino)-4-octylamino-cyclobut-3-ene-1,2-dione;

e) 3-decylamino-4-(4-{2-[2-hydroxy-phenoxy)-propylamino]-propyl}phenylamino)-cyclobut-3-ene-1,2-dione;

f) 3-(4-{2-[(2S)-3-(9H-carbazol-4-yloxy)-2-hydroxy-propylamino]-propyl}-phenylamino)-4-octylamino-cyclobut-3-ene-1,2-dione;

g) 3-(4-{[(2S)-3-(9H-carbazol-4-yloxy)-2-hydroxy-propylamino]-propyl}-phenylamino)-4-decylamino-cyclobut-3-ene-1,2-dione;

h) 3-decylamino-4-{4-[4-[2[((2S)-2-hydroxy-3-phenoxy-propylamino)-propyl]-phenylamino)-cyclobut-3-ene-1,2-dione;

i) 3-{4-[2-((2S)-2-hydroxy-3-phenoxy-propylamino)-propyl]-phenylamino}-4-octylamino-cyclobut-3-ene-1,2-dione;

j) (1R)-1-(3-chloro-phenyl)-2-{1-methyl-2-[4-(octylamino-1,1-dioxo-1H-1-.lambda(6).-[1,2,5]thiadiazol-3-ylamino)-phenyl]-ethylamino}-ethanol;

k) (1R)-1-(3-chloro-phenyl)-2-{2-[3-(4-hexylamino-1,1-dioxo-1H-1-.lambda(6).-[1,2,5]thiadiazol-3-ylamino)-phenyl]-1-methyl-ethylamino}-ethanol;

l) (1R)-1-(3-chloro-phenyl)-2-{1-methyl-2-[3-(4-octylamino-1,1-dioxo-1H-1-.lambda(6).-[1,2,5]thiadiazol-3-ylamino)-phenyl]-ethylamino}-ethanol;

m) (2S)-1-(4-Benzyloxy-phenoxy)-3-{1-methyl-2-[4-(4-octylamino- 1, 1-dioxo-1H-1.lambda(6).-[1,2,5]thiadiazol-3-ylamino)-phenyl]-ethylamino}-propan-2-ol;

n) 4-((2S)-2-hydroxy-3{1-methyl-2-[4-(4-octylamino-1,1-dioxo-1H-1-.lambda(6).-[1,2,5]thiadiazol-3-ylamino)-phenyl]-ethylamino}-propoxy)-phenol;

o) (2S)-1-(4-Benzyloxy-phenoxy)-3-{2-[4-(4-decylamino-1,1-dioxo-1H-1-.lambda(6).-[1,2,5]thiadiazol-3-ylamino)-phenyl]-1-methyl-ethylamino}-propan-2-ol;

p) (2S)-1-(4-Benzyloxy-phenoxy)-3-{1,1-dimethyl-2-[4-(4-octylamino-1,1-dioxo-1H-1-.lambda(6).-[1,2,5]thiadiazol-3-ylamino)-phenyl]-ethylamino}-propan-2-ol;

q) (2S)-1-(9H-carbozol-4-yloxy)-3-{2-[4-(4-decylamino-1,1-dioxo-1H-1-.lambda(6).-[1,2,5]thiadiazol-3-ylamino)-phenyl]-1-methyl-ethylamino}-propan-2-ol;

r) (2S)-1-{2-[4-(4-decylamino-1,1-dioxo-1H-1(lambda(6))-[1,2,5]thiadiazol-3-ylamino)-phenyl]-1-methyl-ethylamino}-3-phenoxy-propan-2-ol;

s) (2S)-1-(9H-carbazol-4-yloxy)-3-{1-methyl-2-[4-(4-octylamino-1,1-dioxo-1H-1(lambda(6))-[1,2,5]thiadiazol-3-ylamino)-phenyl]-ethylamino}-propan-2-ol;

t) (2S)-1-{[1-methyl-2-(4-{[4-(octylamino)-1,1-dioxido-1,2,5-thiadiazol-3-yl]amino}phenyl)ethyl]amino}-3-phenoxypropan-2-ol;

u) 4-((2S)-3-{2-[4-(4-decylamino-1,1-dioxo-1H-1(lambda(6))-[1,2,5]thiadiazol-3-ylamino)-phenyl]-1-methyl-ethylamino}-2-hydroxy-propoxy)-phenol;

v) N-[2-Benzyloxy-5-((1R)-1-hydroxy-2-{1-methyl-2-[4-(4-octylamino-1,1-dioxo-1H-1(lambda(6))-[1,2,5]thiadiazol-3-ylamino)-phenyl]-ethylamino}-ethyl)-phenyl]-methanesulfonamide;

w) N-[2-Benzyloxy-5-((1R)-2-{2-[4-(4-decylamino-1,1-dioxo-1H-1(lambda(6))-[1,2,5]thiadiazol-3-ylamino)-phenyl]-1-methyl-ethylamino}-1-hydroxy-ethyl)-phenyl]-methanesulfonamide;

x) N-[2-hydroxy-5-((1R)-1-hydroxy-2-{1-methyl-2-[4-(4-octylamino-1,1-dioxo-1H-1 (lambda(6))-[1,2,5]thiadiazol-3-ylamino}-ethyl)-phenyl]-methanesulfonamide;

y) N-[5-((1R)-2-{2-[4-(4-decylamino-1,1-dioxo-1H-1(lambda(6))-[1,2,5]thiadiazol-3-ylamino)-phenyl]-1-methyl-ethylamino}-1-hydroxy-ethyl)-2-hydroxy-phenyl]-methanesulfonamide;

z) 4-((2S)-3-{1,1-dimethyl-2-[4-(4-octylamino-1,1-dioxo-1H-1(lambda(6))-[1,2,5]thiadiazol-3ylamino)-phenyl]-ethylamino}-2-hydroxy-propoxy)-phenol;

aa) (2S)-1-(4-Benzyloxy-phenoxy)-3-(2-{4-[4-(2,2-diphenyl-ethylamino)-1,1-dioxo-1H-1(lambda(6))-[1,2,5]thiadiazol-3-ylamino]-phenyl)-1, 1-dimethyl-ethylamino)-propan-2-ol;

bb) 4-[(2S)-3-(2-{4-[4-(2,2-diphenyl-ethylamino)-1,1-dioxo-1H-1(lambda(6))-[1,2,5]thiadiazol-3-ylamino]-phenyl}-1,1-dimethyl-ethylamino)-2-hydroxy-propoxy]-phenol;

cc) (2S)-1-(4-Benzyloxy-phenoxy)-3-[2-(4-{1 ,-dioxo-4-[(1-phenyl-cyclopentylmethyl)-amino]-1H-1(lambda(6))-[1,2,5]thiadiazol-3-ylamino}-phenyl)-1-methyl-ethylamino]-propan-2-ol;

dd) 4-{(2S)-3-[2-(4-{1,1-dioxo-4-[(1-phenyl-cyclopentylmethyl)-amino]-1H-1(lambda(6))-[1,2,5]thiadiazol-3-ylamino}-phenyl)-1-methyl-ethylamino]-2-hydroxy-propoxy}-phenol;

ee) (2S)-1-(4-Benzyloxy-phenoxy)-3-{2-{4-(4-{[1-(4-dimethylamino-phenyl)-cyclopentylmethyl]-amino}-1,1-dioxo-1H-1(lambda(6))-[1,2,5]thiadiazol-3-ylamino)-phenyl]-1,1-dimethyl-ethylamino}-propan-2-ol;

ff) 4-[4-(4-{2-[(2S)-3-(4-Benzyloxy-phenoxy)-2-hydroxy-propylamino]-propyl}-phenylamino)-1,1-dioxo-1H-1(lambda(6))-[1,2,5]thiadiazol-3-ylamino]-butyric acid ethyl ester;

gg) 4-{[(2S)-3-({2-[4-({4-[(1-[4-(dimethylamino)phenyl]cyclopentyl}methyl)amino]-1,1-dioxido-1,2,5-thiadiazol-3-yl}amino)phenyl]-1,1-dimethylethyl}amino)-2-hydroxypropyl]oxy}phenol;

hh) 4-[4-(4-{2-[(2S)-2-hydroxy-3-(4-hydroxy-phenoxy)-propylamino]-propyl}-phenylamino)-1,1-dioxo-1H-1.lambda(6).-[1,2,5]thiadiazol-3-ylamino]-butyric acid ethyl ester;

ii) 1-[4-(1-{[4-(4-{2-[(2R)-3-(4-Benzyloxy-phenoxy)-2-hydroxy-propylamino]-2-methyl-propyl}-phenylamino)-1,1-dioxo-1H-1.lambda(6).-[1,2,5]thiadiazol-3-ylamino]-methyl}cyclopentyl)-phenyl]-3-hexyl-urea;

jj) 1-hexyl-3-[4-( 1-{[4-(4-{2-[(2S)-2-hydroxy-3-(4-hydroxy-phenoxy)-propylamino]-2-methyl-propyl}-phenylamino)-1, 1-dioxo-1H-1.lambda(6).-[1,2,5]thiadiazol-3-ylamino]-methyl}-cyclopentyl)-phenyl]-urea;

kk) N-[5-(2-{2-[4-(4-{[1-(4-dimethylamino-phenyl)-cyclopentylmethyl]-amino}-1,1-dioxo-1H-1.lambda(6).-[1,2,5]thiadiazol-3-ylamino)-phenyl]-1,1-dimethyl-ethylamino}-1-hydroxy-ethyl)-2-hydroxy-phenyl]-methanesulfonamide;

ll) (2S)-1-(4-Benzyloxy-phenoxy)-3-{2-[4-(4-octylamino-1,1-dioxo-1H-1.lambda(6).-[1,2,5]thiadiazol-3-ylamino)-phenyl]ethylamino}-propan-2-ol;

mm) 4-((2S)-2-hydroxy-3-{2-[4-(4-octylamino-1,1-dioxo-1H-1.lambda(6).-[1,2,5]thiadiazol-3-ylamino)-phenyl]-ethylamino}-propoxy)-phenol;

nn) (2S)-1-(1,3-Benzodioxol-5-yloxy)-3-{1-methyl-2-[4-(4-octylamino-1,1 dioxo-1H-1.lambda(6).-[1,2,5]thiadiazol-3-ylamino)-phenyl]-ethylamino}-propan-2-ol;

oo) (S)-4-{2-hydroxy-3-[2-(4-{4-[2-(4-methoxy-phenyl)-ethylamino]-1,1-dioxo-1H-1.lambda(6).-[1,2,5]thiadiazol-3-ylamino}-phenyl)-1-methyl-ethylamino]-propoxy}-phenol;

pp) 4-{(2S)-3-[2-(4-{4-[2-(4-Fluoro-phenyl)-ethylamino]-1,1-dioxo-1H-1.lambda(6).-[1,2,5]thiadiazol-3-ylamino}-phenyl-1-methyl-ethylamino]-2-hydroxy-propoxy}-phenol;

qq) 4-{(2S)-3-[1-(4-{4-[2-(4-Fluoro-phenyl)-ethylamino]-1 1-dioxo-1H-1.lambda(6).-[1,2,5]thiadiazol-3-ylamino}-phenyl)-piperidin-4-ylamino]-2-hydroxy-propoxy}-phenol;

or a pharmaceutically acceptable salt thereof.

5. A method of treating metabolic disorders mediated by insulin resistance or hyperglycemia in a mammal in need thereof which comprises providing to said mammal, an effective amount of a compound of formula I having the structure

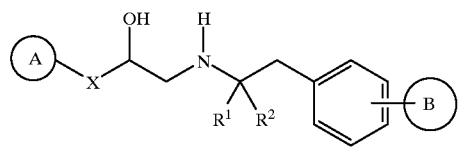

wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

(B)— is

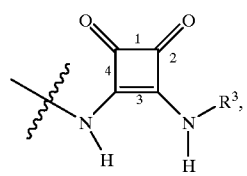

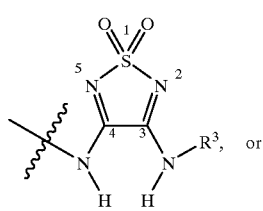 or

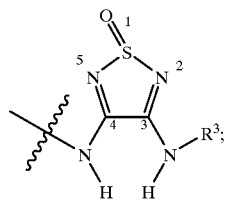

X is —OCH$_2$— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;
R$^1$ and R$^2$ are each, independently, hydrogen, alkyl of 1–6 carbon atoms, or cycloalkyl of 3–8 carbon atoms;
R$^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;
(b) cycloalkyl of 3–8 carbon atoms;
(c) arylalkyl wherein the alkyl moiety contains 1–10 carbon atoms;
(d) heterocycle or heterocyclealkyl, wherein the alkyl moiety contains 1–6 carbon atoms, and the heterocycle is
 i) a 5–6 membered heterocyclic ring having 1–4 heteroatoms selected from O, N, and S, optionally substituted with 1–2 Y groups;
 ii) a phenyl fused heterocycle having 1–4 heteroatoms selected from O, N, and S, optionally substituted with 1–2 Y groups; or
 iii) a phenyl fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;
Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;
m=0–2;
n=1–2;

or a pharmaceutically acceptable salt thereof.

6. A method of treating or inhibiting type II diabetes in a mammal in need thereof which comprises providing to said mammal, an effective amount of a compound of Formula I having the structure

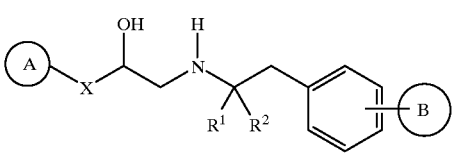

-continued wherein,  is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

 is

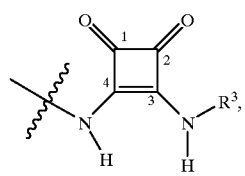
2

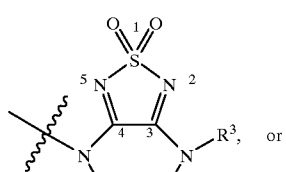 or
3

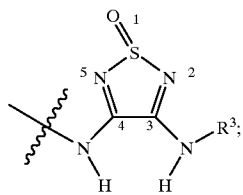
3a

X is —OCH$_2$— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;
R$^1$ and R$^2$ are each, independently, hydrogen, alkyl of 1–6 carbon atoms, or cycloalkyl of 3–8 carbon atoms;
R$^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;
(b) cycloalkyl of 3–8 carbon atoms;
(c) arylalkyl wherein the alkyl moiety contains 1–10 carbon atoms;
(d) heterocycle or heterocyclealkyl, wherein the alkyl moiety contains 1–6 carbon atoms, and the heterocycle is i) a 5–6 membered heterocyclic ring having 1–4 heteroatoms selected from O, N, and S, optionally substituted with 1–2 Y groups;
ii) a phenyl fused heterocycle having 1–4 heteroatoms selected from O, N, and S, optionally substituted with 1–2 Y groups; or
iii) a phenyl fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;
Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;
m=0–2;
n=1–2;

or a pharmaceutically acceptable salt thereof.

7. A method of modulating glucose levels in a mammal in need thereof which comprises providing to said mammal, an effective amount of a compound of formula I having the structure

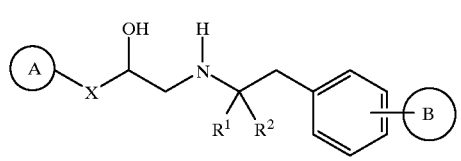
I wherein,  is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

 is

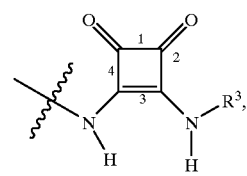
2

-continued

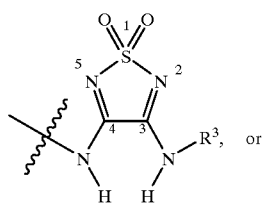

3

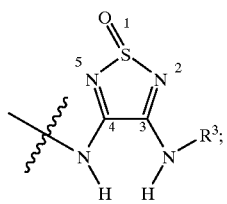

3a

X is —OCH₂— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;
R$^1$ and R$^2$ are each, independently, hydrogen, alkyl of 1–6 carbon atoms, or cycloalkyl of 3–8 carbon atoms;
R$^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;
(b) cycloalkyl of 3–8 carbon atoms;
(c) arylalkyl wherein the alkyl moiety contains 1–10 carbon atoms;
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;
Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;
m=0–2;
n=1–2;

or a pharmaceutically acceptable salt thereof.

8. A method of treating or inhibiting urinary incontinence in a mammal in need thereof which comprises providing to said mammal an effective amount of a compound of formula I having the structure

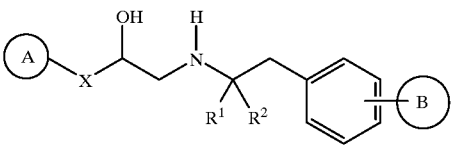

I wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

(B)— is

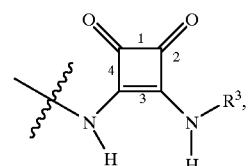

2

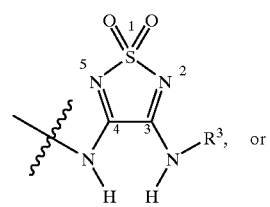

3

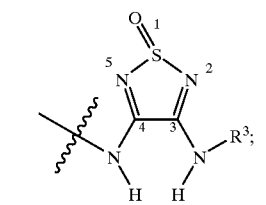

3a

X is —OCH₂— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;
R$^1$ and R$^2$ are each, independently, hydrogen, alkyl of 1–6 carbon atoms, or cycloalkyl of 3–8 carbon atoms;
R$^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;

(b) cycloalkyl of 3–8 carbon atoms;
(c) arylalkyl wherein the alkyl moiety contains 1–10 carbon atoms;
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

$R^4$ and $R^5$ are each, independently, hydrogen, alkyl of 1–10 carbon atoms, or cycloalkyl of 3–8 carbon atoms;
Z is halogen, alkyl of 1–10 carbon atoms, —$CO_2R^4$, benzyloxy, —$NHC(O)NHR^4$, —$NR^4R^5$, —$OR^4$, —$COR^4$, —$S(O)_mR^4$; or —$S(O)_nNR^4R^5$;
m=0–2;
n=1–2;

or a pharmaceutically acceptable salt thereof.

9. A method of treating or inhibiting atherosclerosis, gastrointestinal disorders, neurogenetic inflammation, glaucoma, or ocular hypertension in a mammal in need thereof, which comprises providing to said mammal an effective amount of a compound of formula I having the structure

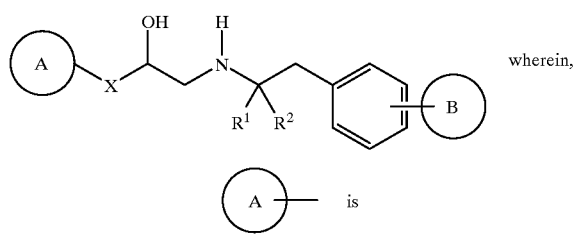

wherein,

A is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

B is

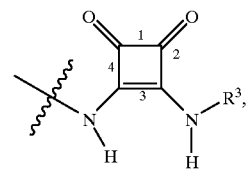

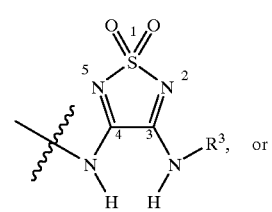

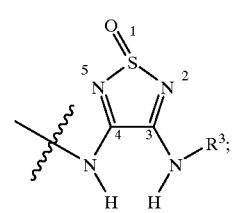

X is —$OCH_2$— or a bond;
Y is hydroxy, halogen, cyano, —$SO_mR^4$, —$SO_nNR^4R^5$, —$NHSO_2R^4$, —$NR^4R^5$, alkyl of the 1–10 carbon atoms, cycloalkyl of 3–8 carbon atoms, alkoxy of 1–10 carbon atoms, arylalkoxy, —$COR^4$, or —$CO_2R^4$;
$R^1$ and $R^2$ are each, independently, hydrogen, alkyl of 1–6 carbon atoms, or cycloalkyl of 3–8 carbon atoms;
$R^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —$CO_2H$; —$CO_2R^4$; amino; —$NR^4R^5$; and —$NHCOR^4$;
(b) cycloalkyl of 3–8 carbon atoms;
(c) arylalkyl wherein the alkyl moiety contains 1–10 carbon atoms;
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

$R^4$ and $R^5$ are each, independently, hydrogen, alkyl of 1–10 carbon atoms, or cycloalkyl of 3–8 carbon atoms;

Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;

m=0–2;
n=1–2;

or a pharmaceutically acceptable salt thereof.

10. A method of increasing the lean meat to fat ratio in a mammal in need thereof, which comprises providing to said mammal an effective amount of a compound of formula I having the structure

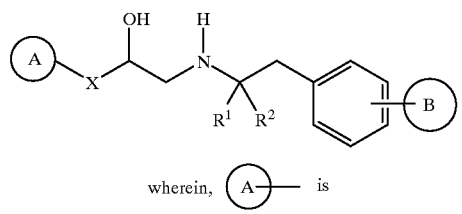

wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

(B)— is

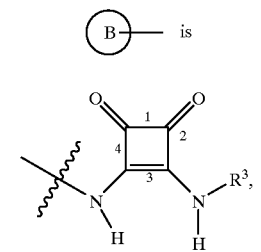

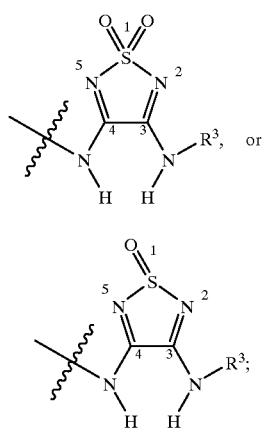

X is —OCH$_2$— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;

R$^1$ and R$^2$ are each, independently, hydrogen, alkyl of 1–6 carbon atoms, or cycloalkyl of 3–8 carbon atoms;
R$^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;
(b) cycloalkyl of 3–8 carbon atoms;
(c) arylalkyl wherein the alkyl moiety contains 1–10 carbon atoms;
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;
Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;
m=0–2;
n=1–2;

or a pharmaceutically acceptable salt thereof.

11. A pharmaceutical composition which comprises a compound of formula I having the structure

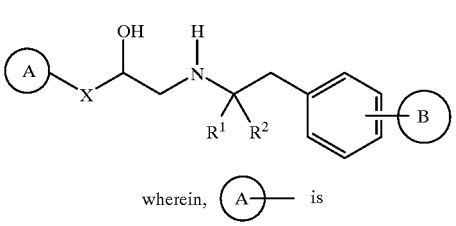

wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or (d) a phenyl fused heterocycle having 1–4 heteroatoms selected from O, N, and S, having a second phenyl ring fused to the heterocyclic ring, optionally substituted with 1–2 Y groups;

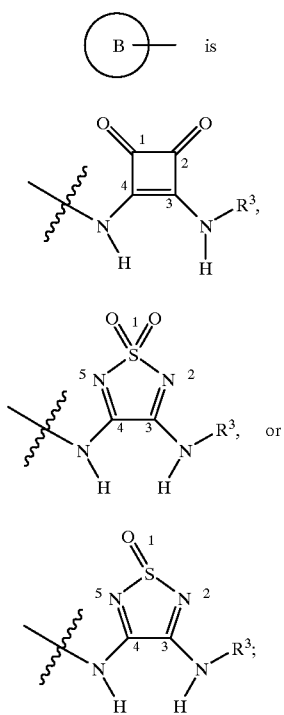

X is —OCH$_2$— or a bond;
Y is hydroxy, halogen, cyano, —SO$_m$R$^4$, —SO$_n$NR$^4$R$^5$, —NHSO$_2$R$^4$, —NR$^4$R$^5$, alkyl of 1–10 carbon atoms, cycloalkyl of 3–8 carbon atoms, alkoxy of 1–10 carbon atoms, arylalkoxy, —COR$^4$, or —CO$_2$R$^4$;

R$^1$ and R$^2$ are each, independently, hydrogen, alkyl of 1–6 carbon atoms, or cycloalkyl of 3–8 carbon atoms;
R$^3$ is (a) alkyl of 1–10 carbon atoms, optionally substituted with 1–5 groups selected from the goup consisting of halogen; hydroxy; spirocycloalkyl of 5–7 carbon atoms, phenyl optionally mono- or di-substituted with Z; oxo; —CO$_2$H; —CO$_2$R$^4$; amino; —NR$^4$R$^5$; and —NHCOR$^4$;
(b) cycloalkyl of 3–8 carbon atoms;
(c) arylalkyl wherein the alkyl moiety contains 1–10 carbon atoms;
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R$^4$ and R$^5$ are each, independently, hydrogen, alkyl of 1–10 carbon atoms, or cycloalkyl of 3–8 carbon atoms;
Z is halogen, alkyl of 1–10 carbon atoms, —CO$_2$R$^4$, benzyloxy, —NHC(O)NHR$^4$, —NR$^4$R$^5$, —OR$^4$, —COR$^4$, —S(O)$_m$R$^4$; or —S(O)$_n$NR$^4$R$^5$;
m=0–2;
n=1–2;

or a pharmaceutically acceptable salt thereof, and a pharmaceutical carrier.

* * * * *